(12) United States Patent
Dann et al.

(10) Patent No.: US 8,182,459 B2
(45) Date of Patent: May 22, 2012

(54) DEVICES AND METHODS FOR ENDOLUMENAL GASTROINTESTINAL BYPASS

(75) Inventors: Mitchell Dann, Wilson, WY (US); Joshua Butters, Chandler, AZ (US); Greg Fluet, Jackson, WY (US); Lee Guterman, Amherst, NY (US); Jonathan Kagan, Hopkins, MN (US); Paul Swain, London (GB); Gerard von Hoffmann, Trabuco Canyon, CA (US); James Wright, Carpinteria, CA (US)

(73) Assignee: ValenTx, Inc., Carpinteria, CA (US)

( * ) Notice: Subject to any disclaimer, the term of this patent is extended or adjusted under 35 U.S.C. 154(b) by 1394 days.

(21) Appl. No.: 11/548,605

(22) Filed: Oct. 11, 2006

(65) Prior Publication Data

US 2007/0198074 A1    Aug. 23, 2007

Related U.S. Application Data

(63) Continuation-in-part of application No. 11/124,634, filed on May 5, 2005, and a continuation-in-part of application No. 10/698,148, filed on Oct. 31, 2003, and a continuation-in-part of application No. 10/998,424, filed on Nov. 29, 2004, and a continuation-in-part of application No. 11/025,364, filed on Dec. 29, 2004.

(60) Provisional application No. 60/569,442, filed on May 7, 2004, provisional application No. 60/613,917, filed on Sep. 27, 2004, provisional application No. 60/480,485, filed on Jun. 21, 2003, provisional application No. 60/448,817, filed on Feb. 21, 2003, provisional application No. 60/437,513, filed on Dec. 30, 2002, provisional application No. 60/430,857, filed on Dec. 3, 2002, provisional application No. 60/428,483, filed on Nov. 22, 2002, provisional application No. 60/422,987, filed on Nov. 1, 2002.

(51) Int. Cl.
*A61M 25/00* (2006.01)

(52) U.S. Cl. ........ 604/500; 604/516; 604/175; 604/525; 604/526; 604/256; 604/909; 604/910; 604/264

(58) Field of Classification Search .................. 604/516, 604/525–526, 256, 238, 167.02, 909–910, 604/175, 500, 264; 600/591, 593, 350; 606/198
See application file for complete search history.

(56) References Cited

U.S. PATENT DOCUMENTS 3,357,432 A    12/1967    Sparks
(Continued)

FOREIGN PATENT DOCUMENTS

EP    0817598    2/1996
(Continued)

OTHER PUBLICATIONS

U.S. Appl. No. 11/431,040, filed May 2006, Kagan et al.
(Continued)

*Primary Examiner* — Bhisma Mehta
*Assistant Examiner* — Edelmira Bosques
(74) *Attorney, Agent, or Firm* — Knobbe, Martens, Olson & Bear LLP

(57) ABSTRACT

The present invention provides devices and methods for attachment of an endolumenal gastrointestinal device, such as an artificial stoma device, a gastrointestinal bypass sleeve or other therapeutic or diagnostic device, within a patient's digestive tract. In one application of the invention, an endolumenal bypass sleeve is removably attached in the vicinity of the gastroesophageal junction to treat obesity and/or its comorbidities, such as diabetes. The bypass sleeve may be at least partially deployed by eversion.

15 Claims, 56 Drawing Sheets

U.S. PATENT DOCUMENTS

| | | |
|---|---|---|
| 3,589,356 A | 6/1971 | Silverman |
| 3,982,544 A | 9/1976 | Dyck |
| 4,006,747 A | 2/1977 | Kronenthal et al. |
| 4,043,345 A | 8/1977 | Kramann et al. |
| 4,109,659 A | 8/1978 | Sheridan |
| 4,134,405 A * | 1/1979 | Smit ........................ 606/108 |
| 4,217,664 A | 8/1980 | Faso |
| 4,235,238 A | 11/1980 | Ogiu et al. |
| 4,252,131 A | 2/1981 | Hon et al. |
| 4,271,839 A | 6/1981 | Fogarty et al. |
| 4,315,509 A | 2/1982 | Smit |
| 4,329,995 A | 5/1982 | Anthracite |
| 4,501,264 A | 2/1985 | Rockey |
| 4,532,926 A | 8/1985 | O'Holla |
| 4,606,347 A | 8/1986 | Fogarty et al. |
| 4,630,609 A | 12/1986 | Chin |
| 4,641,653 A | 2/1987 | Rockey |
| 4,763,653 A | 8/1988 | Rockey |
| 4,846,836 A | 7/1989 | Reich |
| 4,863,440 A | 9/1989 | Chin |
| 4,946,440 A | 8/1990 | Hall |
| 5,085,661 A | 2/1992 | Moss |
| RE34,021 E | 8/1992 | Mueller et al. |
| 5,171,305 A | 12/1992 | Schickling et al. |
| 5,236,423 A | 8/1993 | Mix et al. |
| 5,306,300 A | 4/1994 | Berry |
| 5,314,473 A | 5/1994 | Godin |
| 5,411,508 A | 5/1995 | Bessler et al. |
| 5,431,666 A | 7/1995 | Sauer et al. |
| 5,458,573 A | 10/1995 | Summers |
| 5,470,337 A | 11/1995 | Moss |
| 5,582,616 A | 12/1996 | Bolduc et al. |
| 5,645,568 A | 7/1997 | Chervitz et al. |
| 5,785,684 A | 7/1998 | Zimmon |
| 5,820,584 A | 10/1998 | Crabb |
| 5,824,008 A | 10/1998 | Bolduc et al. |
| 5,843,164 A | 12/1998 | Frantzen |
| 5,861,036 A | 1/1999 | Godin |
| 5,887,594 A | 3/1999 | LoCicero, III |
| 5,957,940 A | 9/1999 | Tanner et al. |
| 5,972,023 A | 10/1999 | Tanner et al. |
| 5,997,556 A | 12/1999 | Tanner |
| 6,113,609 A | 9/2000 | Adams |
| 6,193,733 B1 | 2/2001 | Adams |
| 6,254,642 B1 * | 7/2001 | Taylor ........................ 623/23.64 |
| 6,264,700 B1 | 7/2001 | Kilcoyne et al. |
| 6,285,897 B1 | 9/2001 | Kilcoyne et al. |
| 6,302,917 B1 * | 10/2001 | Dua et al. ................... 623/23.68 |
| 6,312,437 B1 | 11/2001 | Kortenbach |
| 6,338,345 B1 | 1/2002 | Johnson et al. |
| 6,387,104 B1 | 5/2002 | Pugsley, Jr. et al. |
| 6,409,656 B1 | 6/2002 | Sangouard et al. |
| 6,447,533 B1 | 9/2002 | Adams |
| 6,494,888 B1 | 12/2002 | Laufer et al. |
| 6,520,974 B2 | 2/2003 | Tanner et al. |
| 6,535,764 B2 | 3/2003 | Imran et al. |
| 6,544,291 B2 | 4/2003 | Taylor |
| 6,558,400 B2 | 5/2003 | Deem et al. |
| 6,558,429 B2 | 5/2003 | Taylor |
| 6,592,596 B1 | 7/2003 | Geitz |
| 6,595,911 B2 | 7/2003 | LoVuolo |
| 6,626,916 B1 | 9/2003 | Yeung et al. |
| 6,626,919 B1 | 9/2003 | Swanstorm |
| 6,675,809 B2 | 1/2004 | Stack et al. |
| 6,699,263 B2 | 3/2004 | Cope |
| 6,702,735 B2 | 3/2004 | Kelly |
| 6,736,828 B1 | 5/2004 | Adams et al. |
| 6,740,121 B2 | 5/2004 | Geitz |
| 6,746,489 B2 | 6/2004 | Dua et al. |
| 6,764,518 B2 | 7/2004 | Godin |
| 6,790,237 B2 | 9/2004 | Stinson |
| 6,845,776 B2 | 1/2005 | Stack et al. |
| 7,037,344 B2 | 5/2006 | Kagan et al. |
| 7,120,498 B2 | 10/2006 | Imran et al. |
| 7,121,283 B2 | 10/2006 | Stack et al. |
| 7,152,607 B2 | 12/2006 | Stack et al. |
| 7,175,669 B2 | 2/2007 | Geitz |
| RE39,533 E | 3/2007 | Ranoux |
| 7,220,284 B2 | 5/2007 | Kagan et al. |
| 7,244,270 B2 | 7/2007 | Lesh |
| 7,267,694 B2 | 9/2007 | Levine et al. |
| 7,288,099 B2 | 10/2007 | Deem et al. |
| 7,306,614 B2 | 12/2007 | Weller et al. |
| 7,309,341 B2 | 12/2007 | Ortiz et al. |
| 7,314,489 B2 | 1/2008 | McKenna et al. |
| 7,329,285 B2 | 2/2008 | Levine et al. |
| 7,347,875 B2 | 3/2008 | Levine et al. |
| 7,354,454 B2 | 4/2008 | Stack et al. |
| 7,371,215 B2 | 5/2008 | Colliou et al. |
| 7,483,754 B2 | 1/2009 | Imran et al. |
| 7,509,175 B2 | 3/2009 | Sparks et al. |
| 7,520,884 B2 | 4/2009 | Swanstrom et al. |
| 7,666,180 B2 | 2/2010 | Holsten et al. |
| 7,753,870 B2 | 7/2010 | Demerais et al. |
| 7,780,592 B2 | 8/2010 | Tronnes |
| 7,794,447 B2 | 9/2010 | Dann et al. |
| 7,837,669 B2 | 11/2010 | Dann et al. |
| 7,846,138 B2 | 12/2010 | Dann et al. |
| 7,881,797 B2 | 2/2011 | Griffin et al. |
| 7,892,214 B2 | 2/2011 | Kagan et al. |
| 2001/0016748 A1 | 8/2001 | Tanner et al. |
| 2001/0020189 A1 | 9/2001 | Taylor |
| 2001/0020190 A1 | 9/2001 | Taylor |
| 2001/0044595 A1 | 11/2001 | Reydel et al. |
| 2001/0056282 A1 | 12/2001 | Sonnenschein et al. |
| 2002/0016607 A1 | 2/2002 | Bonadio et al. |
| 2002/0026214 A1 | 2/2002 | Tanner et al. |
| 2002/0035370 A1 | 3/2002 | Kortenbach |
| 2002/0040226 A1 | 4/2002 | Laufer et al. |
| 2002/0058960 A1 | 5/2002 | Hudson et al. |
| 2002/0082621 A1 | 6/2002 | Schurr et al. |
| 2002/0165589 A1 | 11/2002 | Imran et al. |
| 2002/0183768 A1 | 12/2002 | Deem et al. |
| 2002/0188354 A1 | 12/2002 | Peghini |
| 2003/0014064 A1 | 1/2003 | Blatter |
| 2003/0018358 A1 | 1/2003 | Saadat |
| 2003/0040804 A1 | 2/2003 | Stack et al. |
| 2003/0040808 A1 | 2/2003 | Stack et al. |
| 2003/0055313 A1 | 3/2003 | Anderson et al. |
| 2003/0055442 A1 | 3/2003 | Laufer et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0109931 A1 | 6/2003 | Geitz |
| 2003/0120285 A1 | 6/2003 | Kortenbach |
| 2003/0130560 A1 | 7/2003 | Suzuki et al. |
| 2003/0130561 A1 | 7/2003 | Suzuki et al. |
| 2003/0139752 A1 | 7/2003 | Pasricha et al. |
| 2003/0171775 A1 | 9/2003 | Belson |
| 2003/0181929 A1 | 9/2003 | Geitz |
| 2003/0191497 A1 | 10/2003 | Cope |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2004/0002734 A1 | 1/2004 | Fallin et al. |
| 2004/0024427 A1 | 2/2004 | Imran et al. |
| 2004/0039452 A1 | 2/2004 | Bessler |
| 2004/0044364 A1 | 3/2004 | DeVries et al. |
| 2004/0059349 A1 | 3/2004 | Sixto, Jr. et al. |
| 2004/0059354 A1 | 3/2004 | Smith |
| 2004/0082963 A1 | 4/2004 | Gannoe et al. |
| 2004/0087976 A1 | 5/2004 | DeVries et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0097986 A1 | 5/2004 | Adams |
| 2004/0097987 A1 | 5/2004 | Pugsley et al. |
| 2004/0102855 A1 | 5/2004 | Shank |
| 2004/0107004 A1 | 6/2004 | Levine et al. |
| 2004/0116949 A1 | 6/2004 | Ewers et al. |
| 2004/0117031 A1 | 6/2004 | Stack et al. |
| 2004/0122453 A1 | 6/2004 | Deem et al. |
| 2004/0122456 A1 | 6/2004 | Saadat et al. |

| | | | | | | |
|---|---|---|---|---|---|---|
| 2004/0122473 A1 | 6/2004 | Ewers et al. | | 2006/0217762 A1 | 9/2006 | Maahs et al. |
| 2004/0133089 A1 | 7/2004 | Kilcoyne et al. | | 2006/0235446 A1 | 10/2006 | Godin |
| 2004/0133147 A1 | 7/2004 | Woo | | 2006/0253126 A1 | 11/2006 | Bjerken et al. |
| 2004/0133219 A1 | 7/2004 | Forsell | | 2006/0264982 A1 | 11/2006 | Viola et al. |
| 2004/0133238 A1 | 7/2004 | Cerier | | 2006/0265082 A1 | 11/2006 | Meade et al. |
| 2004/0138525 A1 | 7/2004 | Saadat et al. | | 2006/0287734 A1 | 12/2006 | Stack et al. |
| 2004/0138529 A1 | 7/2004 | Wiltshire et al. | | 2006/0293742 A1 | 12/2006 | Dann et al. |
| 2004/0138761 A1 | 7/2004 | Stack et al. | | 2007/0005147 A1 | 1/2007 | Levine et al. |
| 2004/0143342 A1 | 7/2004 | Stack et al. | | 2007/0010794 A1 | 1/2007 | Dann et al. |
| 2004/0147958 A1 | 7/2004 | Lam et al. | | 2007/0010864 A1 | 1/2007 | Dann et al. |
| 2004/0148034 A1 | 7/2004 | Kagan et al. | | 2007/0010865 A1 | 1/2007 | Dann et al. |
| 2004/0153167 A1 | 8/2004 | Stack et al. | | 2007/0010866 A1 | 1/2007 | Dann et al. |
| 2004/0158331 A1 | 8/2004 | Stack et al. | | 2007/0016244 A1 | 1/2007 | Behl et al. |
| 2004/0162567 A9 | 8/2004 | Adams | | 2007/0027548 A1 | 2/2007 | Levine et al. |
| 2004/0162568 A1 | 8/2004 | Saadat et al. | | 2007/0027549 A1 | 2/2007 | Godin |
| 2004/0167546 A1 | 8/2004 | Saadat et al. | | 2007/0032879 A1 | 2/2007 | Levine et al. |
| 2004/0181242 A1 | 9/2004 | Stack et al. | | 2007/0083271 A1 | 4/2007 | Levine et al. |
| 2004/0186514 A1 | 9/2004 | Swain et al. | | 2007/0100367 A1 | 5/2007 | Quijano et al. |
| 2004/0193190 A1 | 9/2004 | Luddicoat et al. | | 2007/0100368 A1 | 5/2007 | Quijano et al. |
| 2004/0199189 A1 | 10/2004 | Gifford et al. | | 2007/0106233 A1 | 5/2007 | Huang et al. |
| 2004/0204768 A1 | 10/2004 | Geitz | | 2007/0106313 A1 | 5/2007 | Golden et al. |
| 2004/0220682 A1 | 11/2004 | Levine et al. | | 2007/0129719 A1 | 6/2007 | Kendale et al. |
| 2004/0225183 A1 | 11/2004 | Michlitsch et al. | | 2007/0156248 A1 | 7/2007 | Marco et al. |
| 2004/0225305 A1 | 11/2004 | Ewers et al. | | 2007/0208360 A1 | 9/2007 | Demarais et al. |
| 2004/0243152 A1 | 12/2004 | Taylor et al. | | 2007/0219571 A1 | 9/2007 | Balbierz et al. |
| 2004/0243195 A1 | 12/2004 | Imran et al. | | 2007/0225555 A1 | 9/2007 | Stefanchik |
| 2004/0249362 A1 | 12/2004 | Levine et al. | | 2007/0233162 A1 | 10/2007 | Gannoe et al. |
| 2004/0249367 A1 | 12/2004 | Saadat et al. | | 2007/0293885 A1 | 12/2007 | Binmoeller |
| 2005/0033240 A1 | 2/2005 | Oishi et al. | | 2008/0004606 A1 | 1/2008 | Swain et al. |
| 2005/0033331 A1 | 2/2005 | Burnett et al. | | 2008/0009888 A1 | 1/2008 | Ewers et al. |
| 2005/0033332 A1 | 2/2005 | Burnett et al. | | 2008/0033574 A1 | 2/2008 | Bessler et al. |
| 2005/0049718 A1 | 3/2005 | Dann | | 2008/0058840 A1 | 3/2008 | Albrecht et al. |
| 2005/0065401 A1 | 3/2005 | Saadat et al. | | 2008/0058887 A1 | 3/2008 | Griffin et al. |
| 2005/0075653 A1 | 4/2005 | Saadat et al. | | 2008/0103604 A1 | 5/2008 | Levine et al. |
| 2005/0075654 A1 | 4/2005 | Kelleher | | 2008/0167606 A1 | 7/2008 | Dann et al. |
| 2005/0080431 A1 | 4/2005 | Levine et al. | | 2008/0167610 A1 | 7/2008 | Dann et al. |
| 2005/0080444 A1 | 4/2005 | Kraemer et al. | | 2008/0167629 A1 | 7/2008 | Dann et al. |
| 2005/0085787 A1 | 4/2005 | Laufer | | 2008/0195226 A1 | 8/2008 | Williams et al. |
| 2005/0085900 A1 | 4/2005 | Case et al. | | 2008/0208355 A1 | 8/2008 | Stack et al. |
| 2005/0085923 A1 | 4/2005 | Levine et al. | | 2008/0208356 A1 | 8/2008 | Stack et al. |
| 2005/0096673 A1 | 5/2005 | Stack et al. | | 2008/0221597 A1 | 9/2008 | Wallace et al. |
| 2005/0096750 A1 | 5/2005 | Kagan et al. | | 2008/0228030 A1 | 9/2008 | Godin |
| 2005/0101977 A1 | 5/2005 | Gannoe | | 2008/0243071 A1 | 10/2008 | Quijano et al. |
| 2005/0125020 A1 | 6/2005 | Meade et al. | | 2008/0249533 A1 | 10/2008 | Godin |
| 2005/0125075 A1 | 6/2005 | Meade et al. | | 2008/0269797 A1 | 10/2008 | Stack et al. |
| 2005/0143784 A1 | 6/2005 | Imran | | 2009/0012541 A1 | 1/2009 | Dahl et al. |
| 2005/0177181 A1 | 8/2005 | Kagan et al. | | 2009/0012544 A1 | 1/2009 | Thompson et al. |
| 2005/0187567 A1 | 8/2005 | Baker et al. | | 2009/0012553 A1 | 1/2009 | Swain et al. |
| 2005/0192629 A1 | 9/2005 | Saadat et al. | | 2009/0024143 A1 | 1/2009 | Crews et al. |
| 2005/0197714 A1 | 9/2005 | Sayet | | | | |
| 2005/0197715 A1 | 9/2005 | Kugler et al. | | FOREIGN PATENT DOCUMENTS | | |
| 2005/0203547 A1 | 9/2005 | Weller et al. | | EP | 1237501 | 9/2000 |
| 2005/0222592 A1 | 10/2005 | Gannoe et al. | | WO | WO 80/00007 A1 | 1/1980 |
| 2005/0228413 A1 | 10/2005 | Binmoeller et al. | | WO | WO 91/01117 A1 | 2/1991 |
| 2005/0228504 A1 | 10/2005 | Demerais | | WO | WO 96/29954 A1 | 10/1996 |
| 2005/0247320 A1 | 11/2005 | Stack et al. | | WO | WO 98/56440 A1 | 12/1998 |
| 2005/0256587 A1 | 11/2005 | Egan | | WO | WO 99/60931 A1 | 12/1999 |
| 2005/0261549 A1 | 11/2005 | Hewit et al. | | WO | WO 00/12027 A1 | 3/2000 |
| 2005/0261712 A1 | 11/2005 | Balbierz et al. | | WO | WO 01/35834 A1 | 5/2001 |
| 2005/0267499 A1 | 12/2005 | Stack et al. | | WO | WO 01/43663 A1 | 6/2001 |
| 2005/0267595 A1 | 12/2005 | Chen et al. | | WO | WO 01/85034 A1 | 11/2001 |
| 2006/0009858 A1 | 1/2006 | Levine et al. | | WO | WO 2002/094132 A1 | 11/2002 |
| 2006/0015125 A1 | 1/2006 | Swain | | WO | WO 02/102227 A2 | 12/2002 |
| 2006/0020164 A1 | 1/2006 | Butler et al. | | WO | WO 03/017882 A2 | 3/2003 |
| 2006/0020247 A1 | 1/2006 | Kagan et al. | | WO | WO 03/086246 A1 | 10/2003 |
| 2006/0020277 A1 | 1/2006 | Gostout et al. | | WO | WO 03/086247 A1 | 10/2003 |
| 2006/0020278 A1 | 1/2006 | Burnett et al. | | WO | WO 03/094785 A1 | 11/2003 |
| 2006/0025819 A1 | 2/2006 | Nobis et al. | | WO | WO 2004/017863 A2 | 3/2004 |
| 2006/0047289 A1 | 3/2006 | Fogel | | WO | WO 2004/021894 A1 | 3/2004 |
| 2006/0064120 A1 | 3/2006 | Levine et al. | | WO | WO 2004/041119 A2 | 5/2004 |
| 2006/0074458 A1 | 4/2006 | Imran | | WO | WO 2004/047686 A1 | 6/2004 |
| 2006/0155312 A1 | 7/2006 | Levine et al. | | WO | WO 2004/049982 A2 | 6/2004 |
| 2006/0161139 A1 | 7/2006 | Levine et al. | | WO | WO 2004/064680 A1 | 8/2004 |
| 2006/0161172 A1 | 7/2006 | Levine et al. | | WO | WO 2004/064685 A1 | 8/2004 |
| 2006/0161187 A1 | 7/2006 | Levine et al. | | WO | WO 2004/080336 A2 | 9/2004 |
| 2006/0161265 A1 | 7/2006 | Levine et al. | | WO | WO 2004/087014 A2 | 10/2004 |
| 2006/0173422 A1 | 8/2006 | Reydel et al. | | WO | WO 2004/087233 A2 | 10/2004 |
| 2006/0206063 A1 | 9/2006 | Kagan et al. | | WO | WO 2004/086984 A1 | 11/2004 |
| 2006/0206064 A1 | 9/2006 | Kagan et al. | | WO | WO 2004/103214 A2 | 12/2004 |

| WO | WO 2004/103430 A2 | 12/2004 |
| WO | WO 2004/105643 A1 | 12/2004 |
| WO | WO 2005/011463 A2 | 2/2005 |
| WO | WO 2005/011519 | 2/2005 |
| WO | WO 2005/011519 A2 | 2/2005 |
| WO | WO 2005/032422 | 4/2005 |
| WO | WO 2005/037152 A1 | 4/2005 |
| WO | WO 2005/060869 A1 | 7/2005 |
| WO | WO 2005/060882 A1 | 7/2005 |
| WO | WO 2006/044640 A1 | 4/2006 |

OTHER PUBLICATIONS

U.S. Appl. No. 11/548,605, filed Oct. 2006, Dann et al.
*Antireflux operations at flexible study endoscopy using endoluminal stitching techniques: an experimental study*, Sritharan S. Kadirkamanathan et al., *Gastrointestinal Endoscopy*, vol. 44, No. 2, 1995 pp. 133-143.
*Endoscopic suturing*, C. Paul Swain MD, *Balliere's Clinical Gastroenterology*, vol. 13, No. 1. pp. 97-108, 1999.
*Progression rate of self-propelled feeding tubes in critically ill patients*, Mette M. Berger et al., *Intensive Care Med* Oct. 29, 2002, pp. 1768-1774.
*Iatrogenic Intussusception: a Complication of Long Intestinal Tubes*, Patricia Redmond, M.D., et al., *American Jounal of Gastroenterology*, vol. 77, No. 1, 1982, pp. 39-42.
*Design and Testing of a New, Small Diameter, Single Stitch Endoscopic Sewing Machine*, C.P. Swain et al., *Abstracts Submitted to A/S/G/E/ 1990*, Vo. 36, No. 2, 1990, pp. 213, 214.
*Endoscopic Suturing of a Novel Gastroesophageal Antireflux Device (GARD) A Preliminary Report*, N.J. Godin et al., *Gastrointestinal Endoscopy*, vol. 43, No. 4, 1996.
*An endoscopic stapling device: the development of new flexible endoscopically controlled device for placing multiple transmural staples in gastrointestinal tissue*, C. Paul Swain, MD et al., *Gastrointestinal Endoscopy*, vol. 35, No. 4, 1989 pp. 338-339.
*An endoscopically deliverable tissue-transfixing device for securing biosensors in the gastrointestinal tract*, C. Paul Swain, MD et al. *Gastrointestinal Endoscopy*, 1994 vol. 40 No. 6 pp. 730-734.
*Development of a gastroplasty with variable diameter. Experimental study using artificial sphincters*, M. Merlini et al., 1992 Abstract.
*Synthetic Biodegradable Polymers as Medical Devices*, John C. Middleton et al., *Medical Plastics and Biomaterials Magazine MPS Article Index*, Mar. 1998.
*Experimental study on in situ tissue engineering of the stomach by an acellular collagen sponge scaffold graft*, Hori Y. Nakamura et al., Abstract, May 2001.
*Repair of Full-Thickness Defects in Alimentary Tract Wall with Patches of Expanded Polytetrafluoroethylene*, Daniel S. Oh, MD et al., Annals of Surgery 2002; 235:708-712.
*Stents in the small intestine*, Singh S, Gagneja HK, Abstract, Oct. 2002.
*Endoscopic vertical band gastroplasty with an endoscopic sewing machine*, Amjad N. Awan MD et al., *Gastrointestinal Endoscopy*, vol. 55, No. 2, 2002, pp. 254-256.
*A through-the-scope device of suturing and tissue approximation under EUS control*, Annette Fritscher-Ravens, MD, et al., *Gastrointestinal Endoscopy*, vol. 56, No. 5, 2002, pp. 737-742.
*Evaluation of porcine-derived small intestine submucosa as a biodegradable graft for gastrointestinal healing*, SG del la Fuente et al., Abstract, J. Gastrointest Surg Jan. 2003, pp. 1.
*Bard EndoCinch: the device, the technique and pre-clinical studies*, Paul Swain, M.D. et al., *Gastrointestinal Endoscopy Clinics of North America*, 13, 2003 pp. 75-88.
*Endoscopic suturing for gastroesophageal reflux disease: clinical outcome with the Bard Endocinch*, Richard I. Rothstein, MD et al., *Gastrointestinal Endoscopy Clinics of North America*, 13 (2003) pp. 89-101.
*Wilson-Cook sewing device: the device, technique, and preclinical studies*, Michael Rosen MD, et al., *Gastrointestinal Endoscopy Clinics of North America*, 13 (2003) pp. 103-108.
*Endoscopic full-thickness plication: the device, technique, pre-clinical and early clinical experience*, Ram Chuttani, MD, *Gastrointestinal Endoscopy Clinics of North America*, 13 (2003) pp. 109-116.

*Microvasive gastric stapler: the device, technique, and preclinical results*, Tom R. De Meester MD, *Gastrointestinal Endoscopy Clinics of North America*, 13 (2003) pp. 117-133.
*Endoscopic Gastropexy and Crural Repair for Gastro-Esophageal Reflux: Transgastric Surgery Under Endoscopic Ultrasound Control II*, Anette Fritscher-Ravens et al. *Digestive Disease Week* 2003 Abstract, pp. 1.
*Endoscopic suturing for treatment of GERD*, m. Brian Fennerty, MD, *Gastrointestinal Endoscopy*, vol. 57, No. 3, 2003 pp. 390-395.
*Transgastric gastropexy and hiatal hernia repair for GERD under EUS control: a porcine model*, Annette Fritscher-Ravens, MD et al., *Gastrointestinal Endoscopy*, vol. 59, No. 1, 2004, pp. 89-95.
*Effect of Duodenal-Jejunal Exclusion of a Non-obese Animal Model of Type 2 Diabetes*, Francesco Rubino, MD et al., *Annals of Surgery*, vol. 239, No. 1, Jan. 2004, pp. 1-11.
*Successful Uses in Approximation Ligation & Fixation using the QUIK-STITCH, Endoscopic Suturing System*, PARé Surgical, Inc. Brochure 2001.
*Microvasive WALLSTENT® Colonic and Duodenal Endoprosthesis*, Boston Scientific website, www.bostonscientific.com, Sep. 20, 2002, pp. 1.
*COOK® Wilson-Cook Medical GI Endoscopy*, Wilson Cook: Biliary/Pancreatic Stents, www.cookgroup.com, Sep. 20, 2002, pp. 1-2.
*Bioabsorable Polymers*, William B. Gleason, *University of Minnesota*, 1998, pp. 1-7.
*Cope Gastrointestinal Suture Anchor Set*, www.cookgroup.com, Cook Diagnostic and Interventional Products Advertisement 2000, pp. 1-2.
*LSI Solutions®*, SEW-RIGHT® SR 5, Advertisement received at ASBS Conference 2002, pp. 1.
SEW-RIGHT® SR 5™ & SR 10™, Ti-KNOT® TK 5™ Advertisement received at ASBS Conference 2002.
*Three-dimensional manometric imaging of the lower esophageal sphincter*, Hubert J. Stein, Md. *Surgery*, 1995 vol. 117 No. 6 pp. 692-698.
*A new method of enteroscopy—The double-balloon method*, Yamamoto et al., *Can J. Gastroenterol*, vol. 17, No. 4 Apr. 2003, pp. 273-274.
*Radiocontrolled Movement of a Robot Endoscope in the Human Gastrointestinal Tract*, Paul Swain et al., Abstract—*Gastrointestinal Endoscopy*, vol. 61, No. 5 DDW Abstract Issue: Apr. 2005.
*Techniques for Advancing Guide Wires and Devices in the Lumen of the Gastrointestinal Tract*, Long et al., *Gastrointestinal Endoscopy*, vol. 57, No. 5 Apr. 2003 Abstract, 2003 ASGE Meeting, May 18-21, Orlando Florida.
PCT International Search Report, PCT/US2004/44049 mailed May 30, 2007, pp. 1-9.
Notice of Allowance, U.S. Appl. No. 11/400,724 mailed Sep. 20, 2010 in 7 pages, pp. 1-8.
Notice of Allowance, U.S. Appl. No. 11/430,677 mailed Sep. 23, 2010 in 7 pages, pp. 1-8.
Notice of Allowance, U.S. Appl. No. 11/430,274 mailed Sep. 30, 2010 in 8 pages, pp. 1-7.
Fobi, M.D., Mathais A.L. et al., "Gastric Bypass Operation for Obesity", World J. Surg., Sep. 1998, vol. 22, pp. 925-935.
Pories, M.D., Walter J. et al., "Who Would Have Thought It? An Operation Proves to Be the Most Effective Therapy for Adult-Onset Diabetes Mellitus", Annals of Surgery, Sep. 1995, vol. 222, No. 3, pp. 339-352.
Sugerman, M.D., Harvey J. et al., "Weight Loss With Vertical Banded Gastroplasty and Roux-Y Gastric Bypass for Morbid Obesity With Selective Versus Random Assignment", The American Journal of Surgery, Jan. 1989, vol. 157, pp. 93-102.
Keyser, M.D., Eric J. et al., "Double Closed Loop Obstruction and Perforation in a Previous Roux-en-Y Gastric Bypass", Obesity Surgery, 1998, vol. 8, pp. 475-479.
Oh, M.D., Chung H. et al., "Weight Loss Following Transected Gastric Bypass with Proximal Roux-en-Y", Obesity Surgery, 1997, vol. 7, pp. 142-147.
Crampton, MBBS, Nicholas A., et al., "Silastic Ring Gastric Bypass: Results in 64 Patients", Obesity Surgery, 1997, vol. 7, pp. 489-493.

Office Action, U.S. Appl. No. 10/698,148, mailed Jul. 9, 2009 in 12 pages.
Office Action, U.S. Appl. No. 11/025,364, mailed Aug. 6, 2010 in 8 pages.
Office Action, U.S. Appl. No. 11/124,634, mailed May 13, 2010 in 7 pages.
Office Action, U.S. Appl. No. 11/400,724, mailed Jul. 9, 2009 in 8 pages.
Office Action, U.S. Appl. No. 11,400,724, mailed Dec. 15, 2008 in 8 pages.
Office Action, U.S. Appl. No. 11/861,156, mailed Sep. 22, 2010 in 7 pages.
Office Action, U.S. Appl. No. 11/861,172, mailed Jul. 14, 2009 in 15 pages.
*The LAP-BAND Solution*, BioEnterics Corporation, Brochure http://www.bioenterics.com/ in 2 pages.
*Obesity Treatment*, Medical Innovation Development, Brochure in 4 pages.
*The Remote Controlled Swedish Band, The method of choice in modern treatment of morbid obesity*, Obtech Medical AG, Brochure in 6 pages.
*The Bard EndoCinch Procedure*, Introducing Endoscopic Technology for the Treatment of GERD in 1 page.
ROSS.COM, *Abbott Laboratories Online*, Product Handbook, T-Fastener Set in 1 page.
*T=Anchor Introducer Gun™ Details*, Moss™ Tubes Brochure in 3 pages.
PCT International Search Report for PCT/US2003/34822, mailed Feb. 4, 2004 in 8 pages.
PCT International Search Report for PCT/US07/08882, mailed Dec. 26, 2007 in 14 pages.
PCT International Search Report for PCT/US2005/15795 mailed Nov. 14, 2005.

* cited by examiner

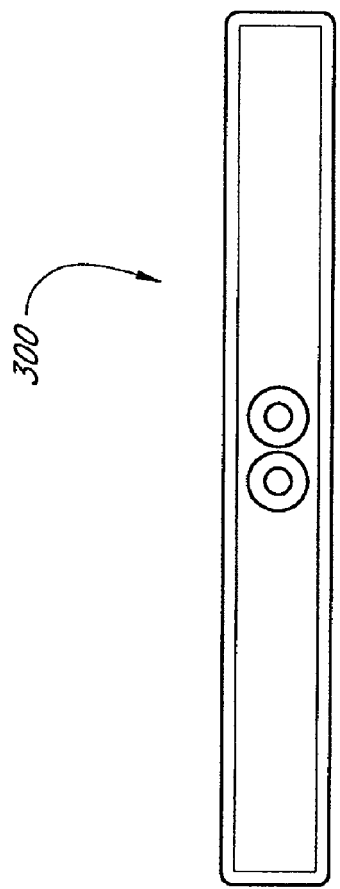
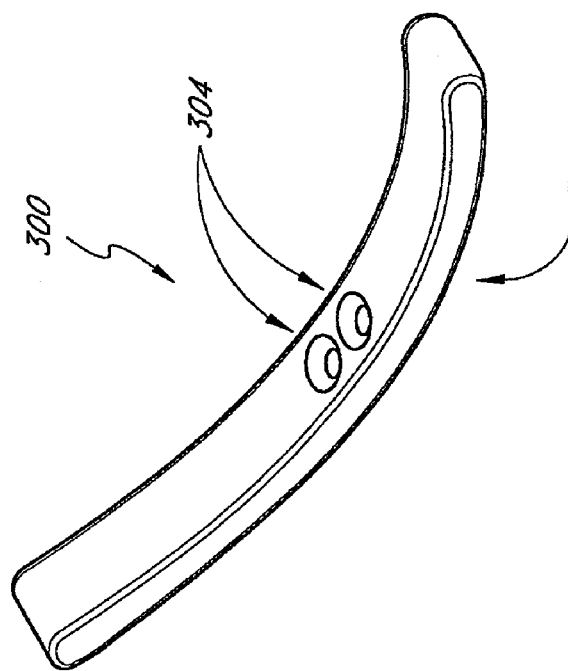

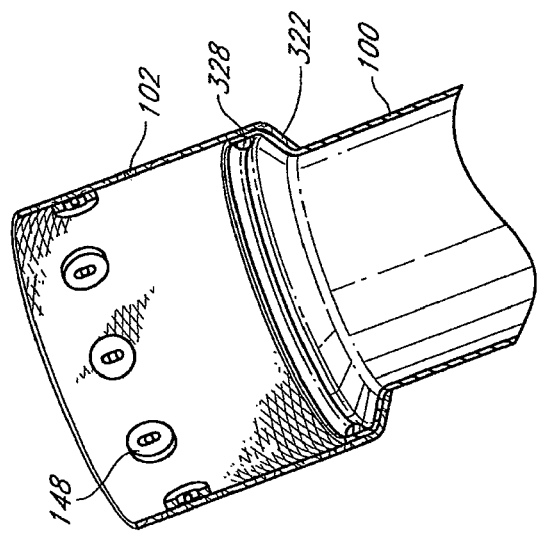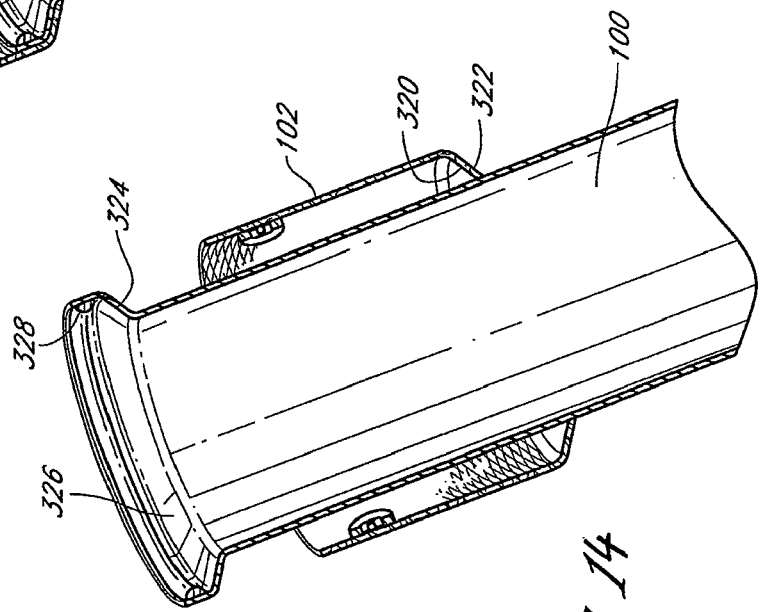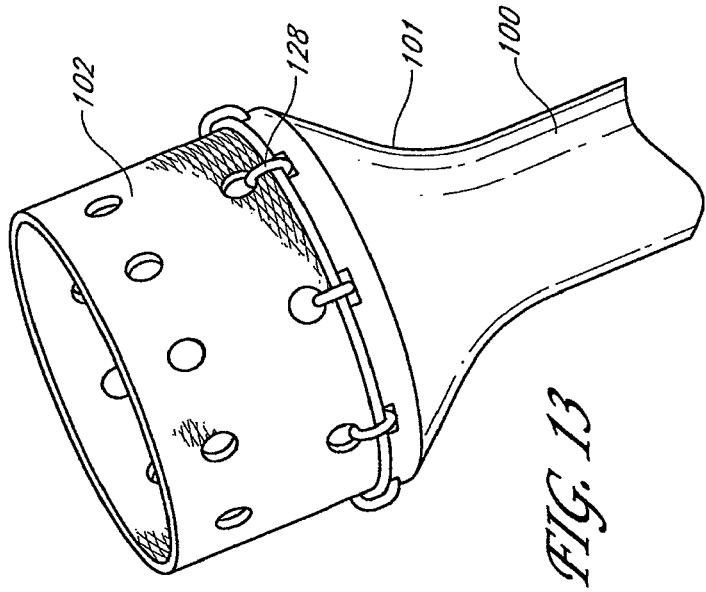

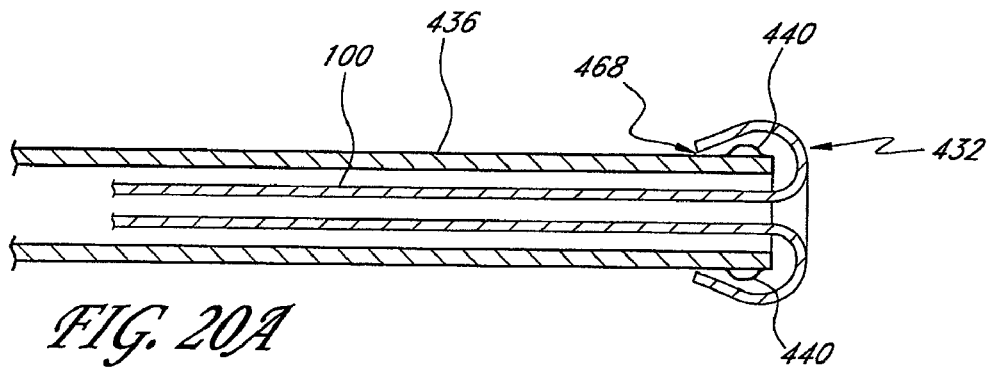
FIG. 20A
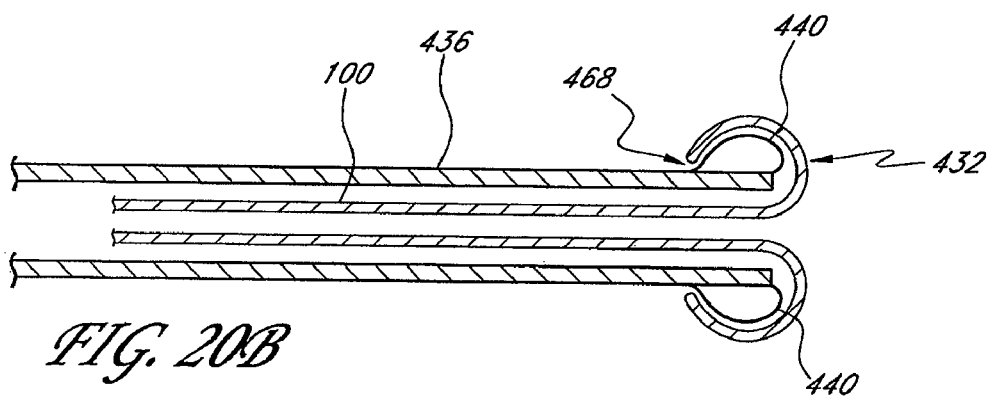
FIG. 20B
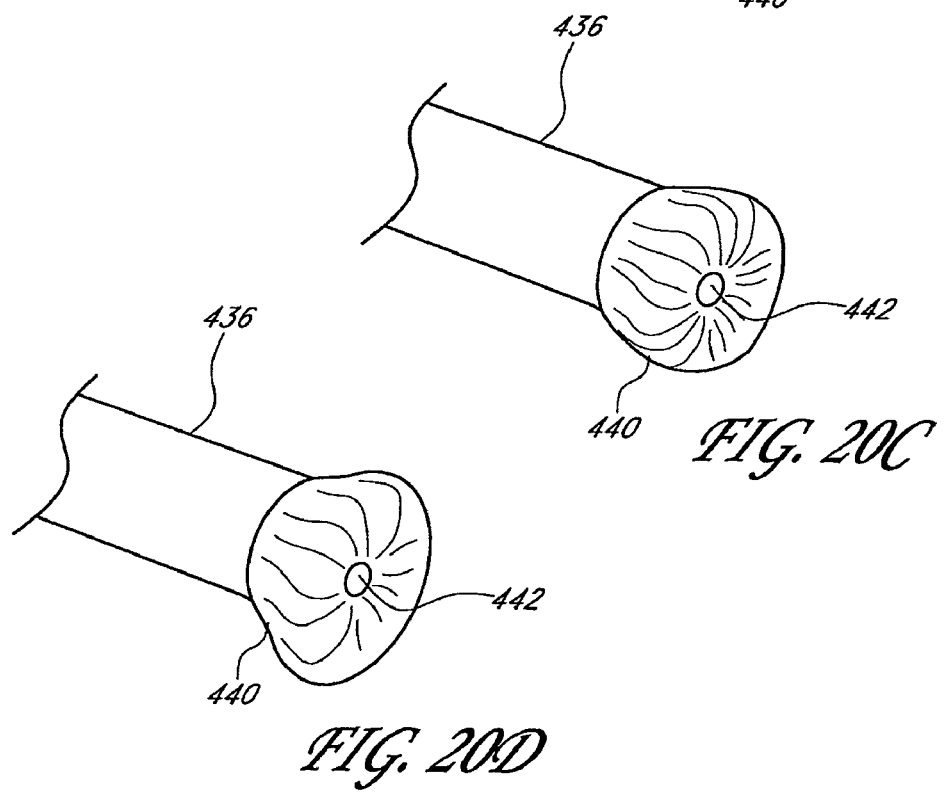
FIG. 20C
FIG. 20D

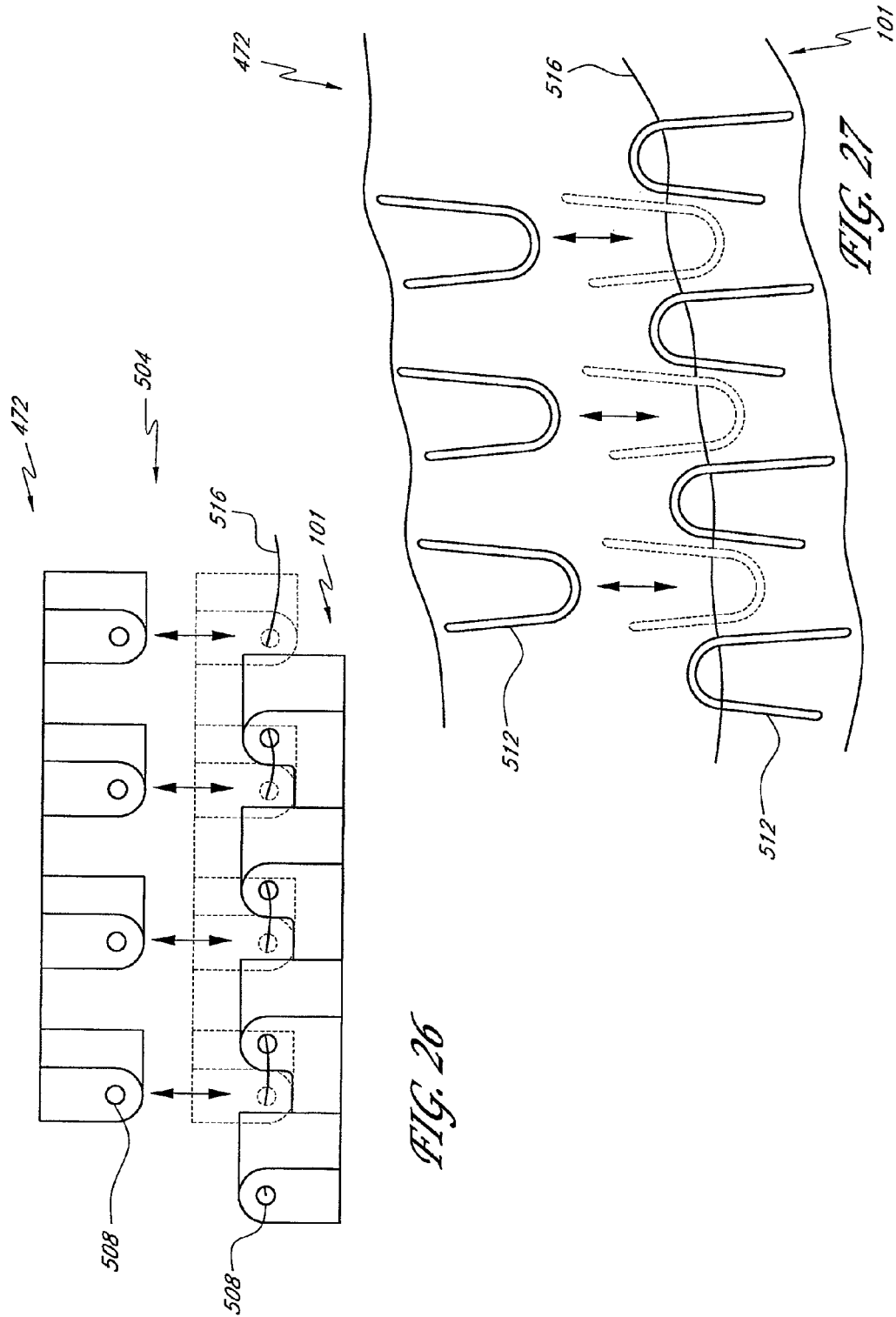

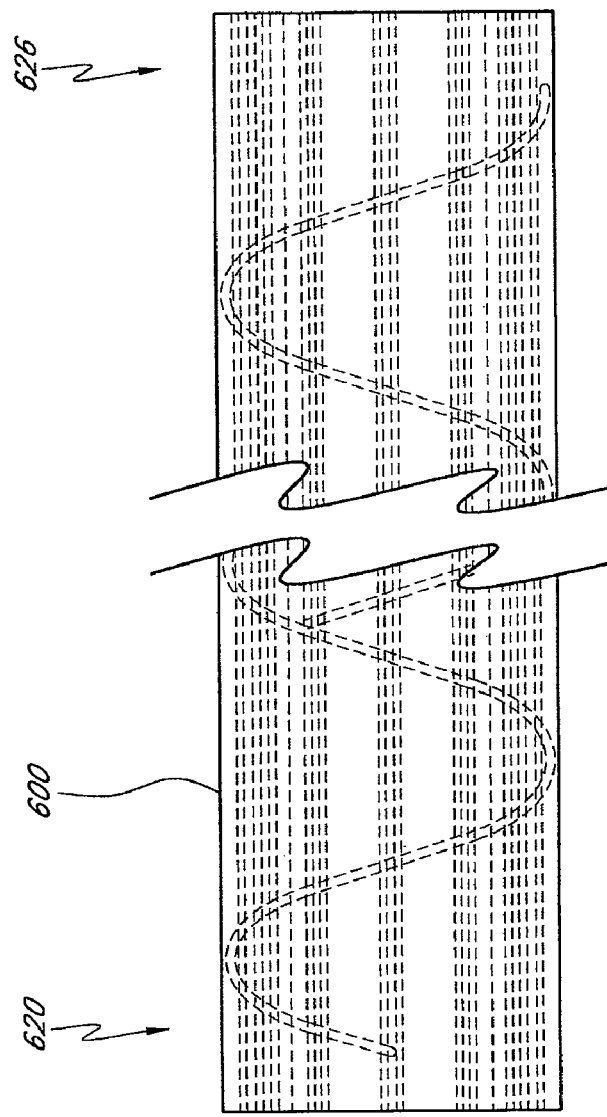
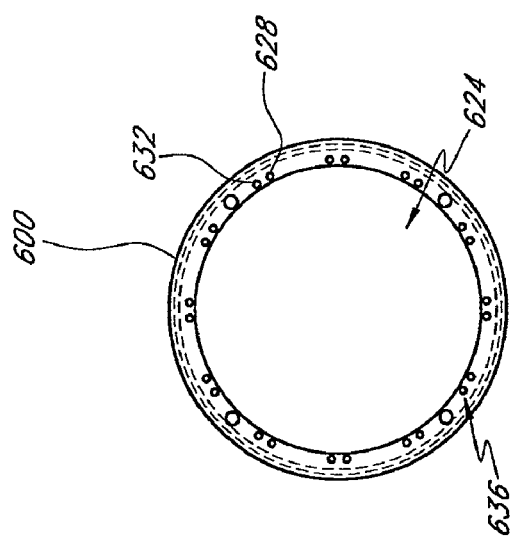
FIG. 29B
FIG. 29A

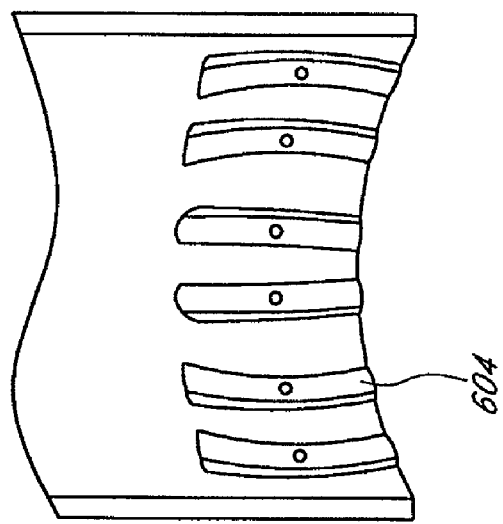
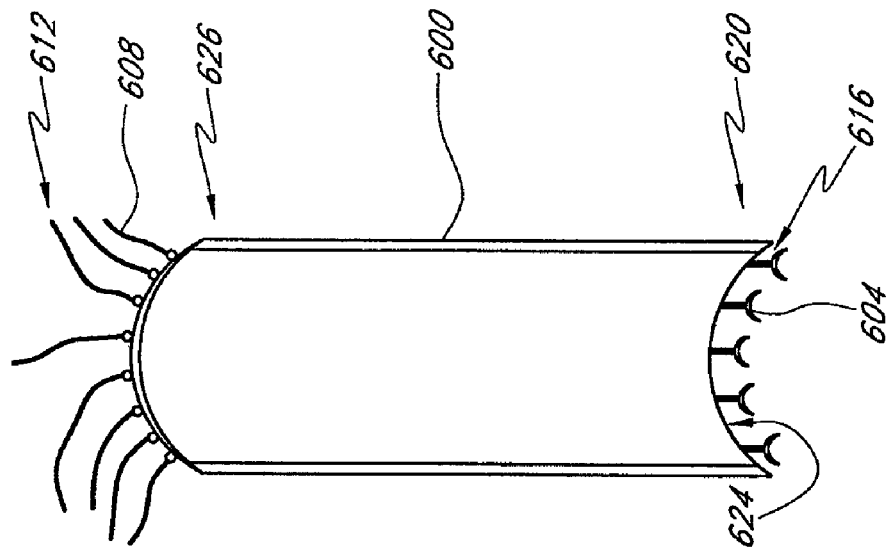
FIG. 30B
FIG. 30A

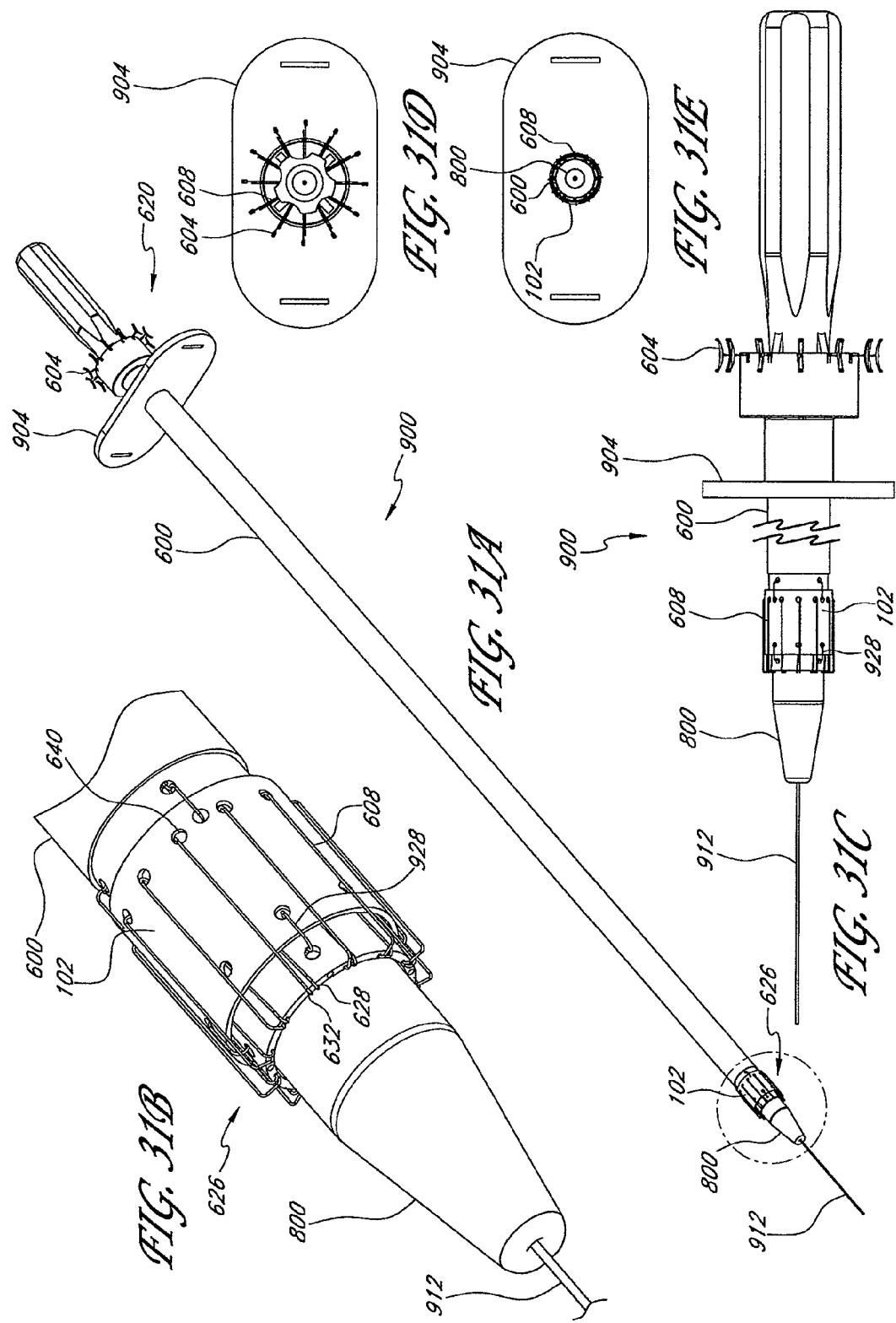

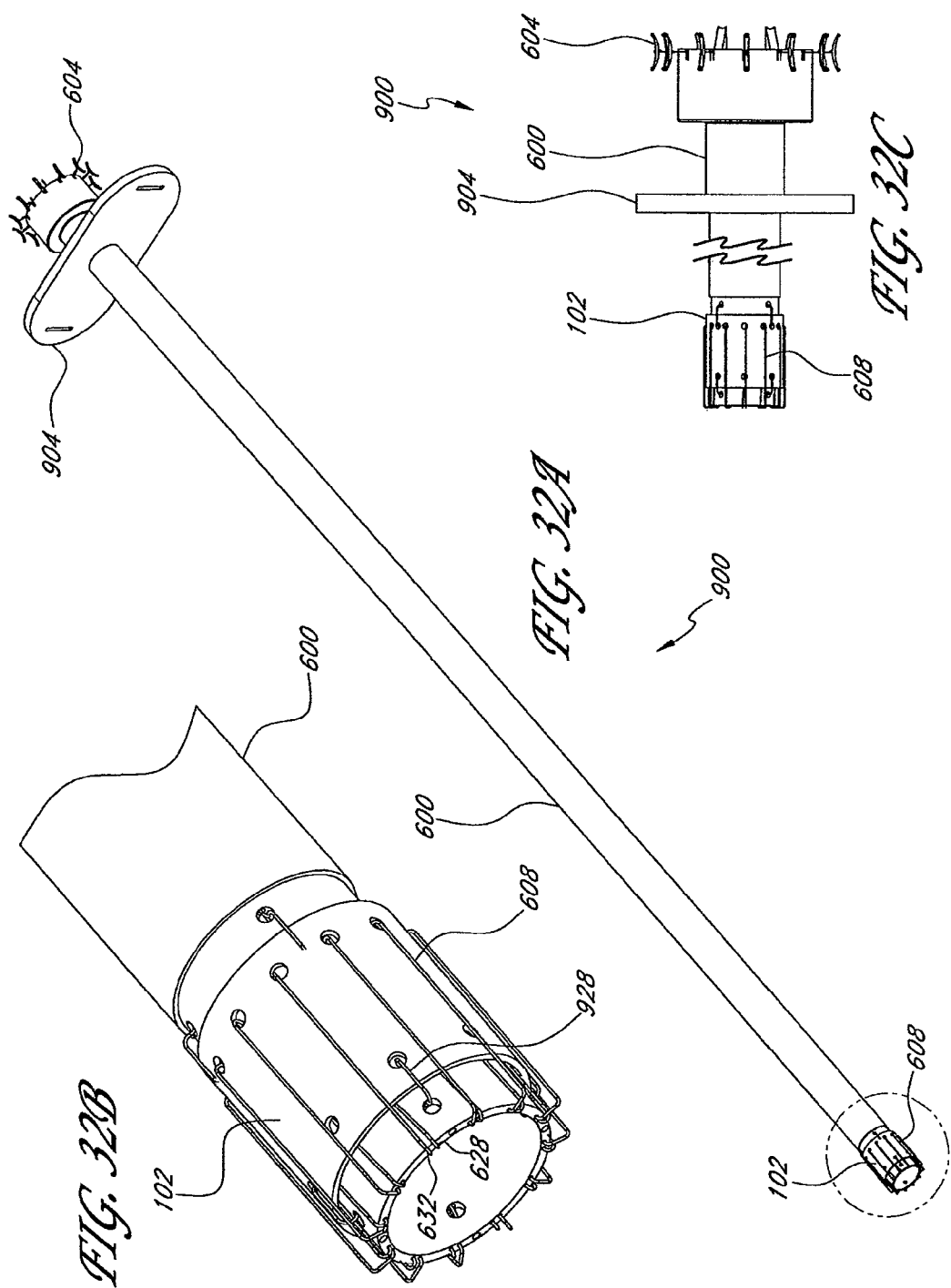

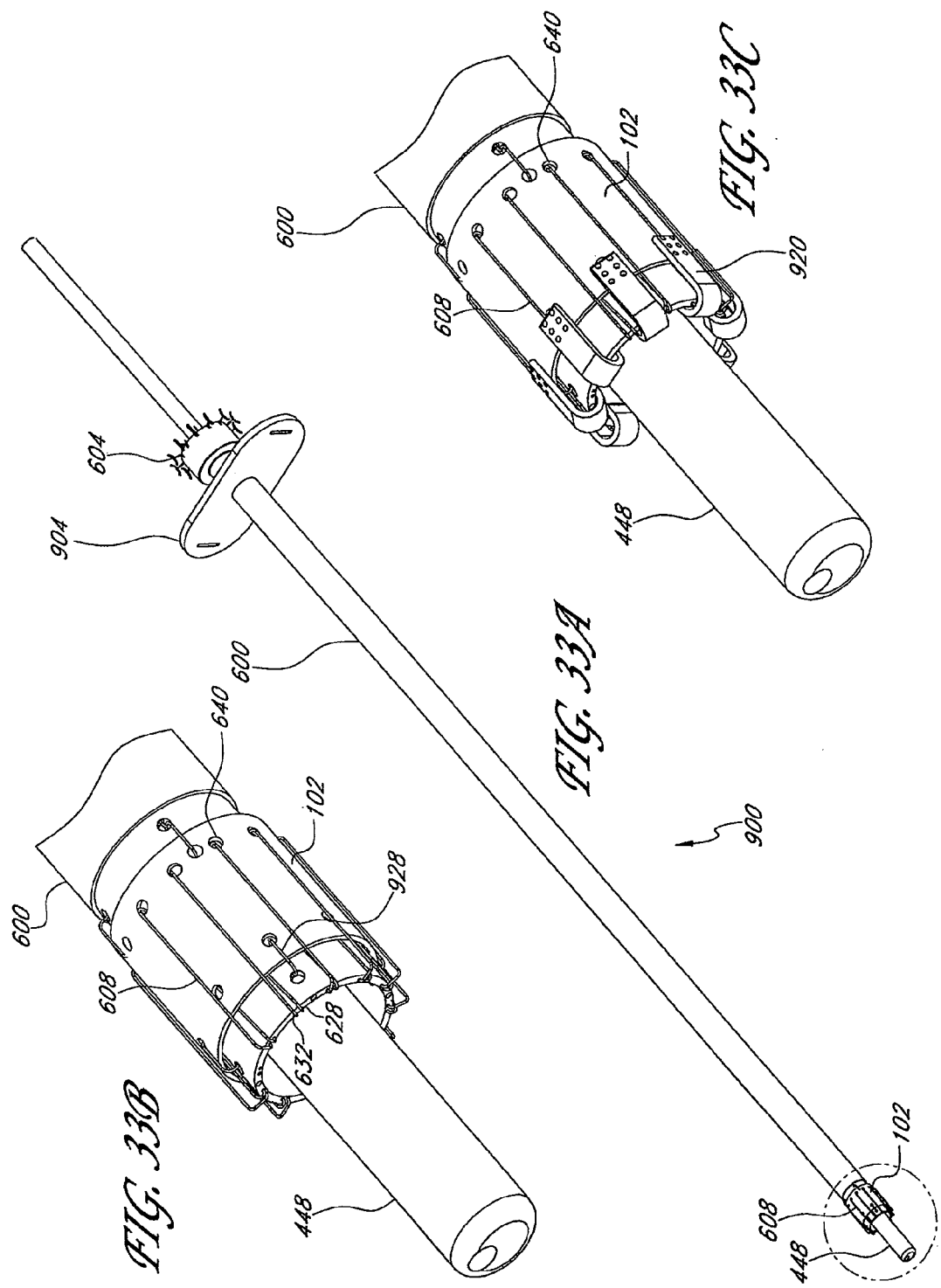

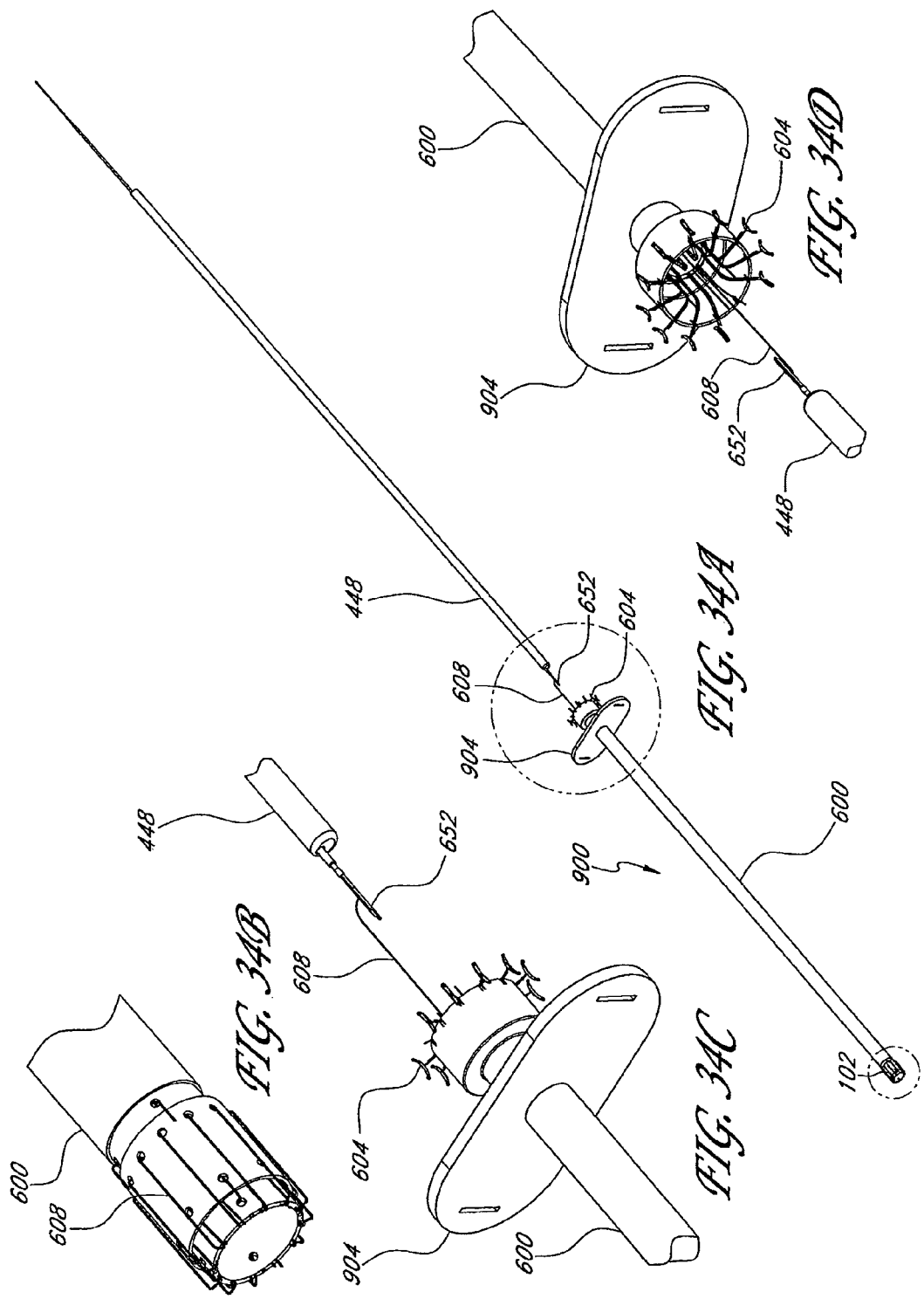

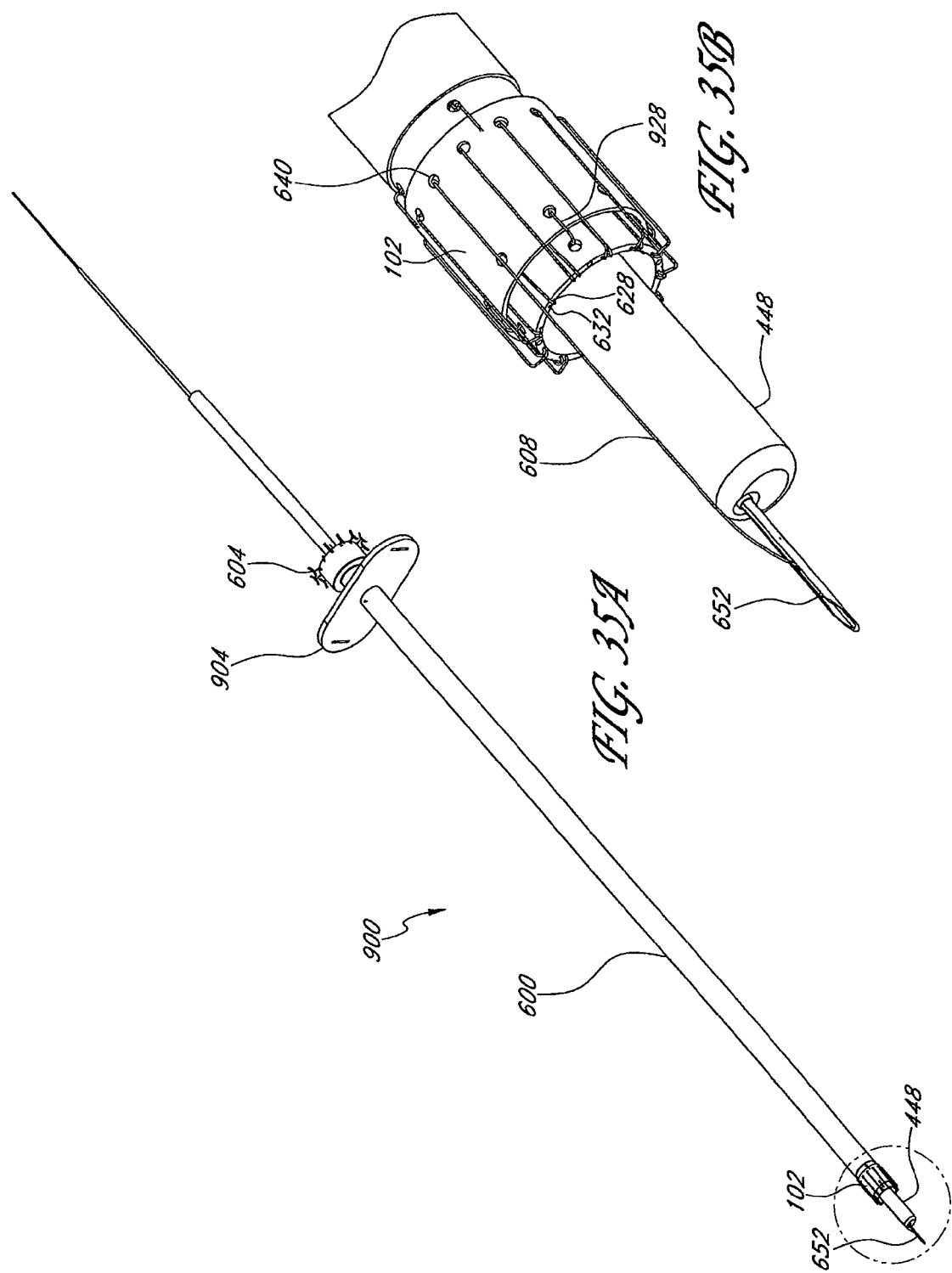

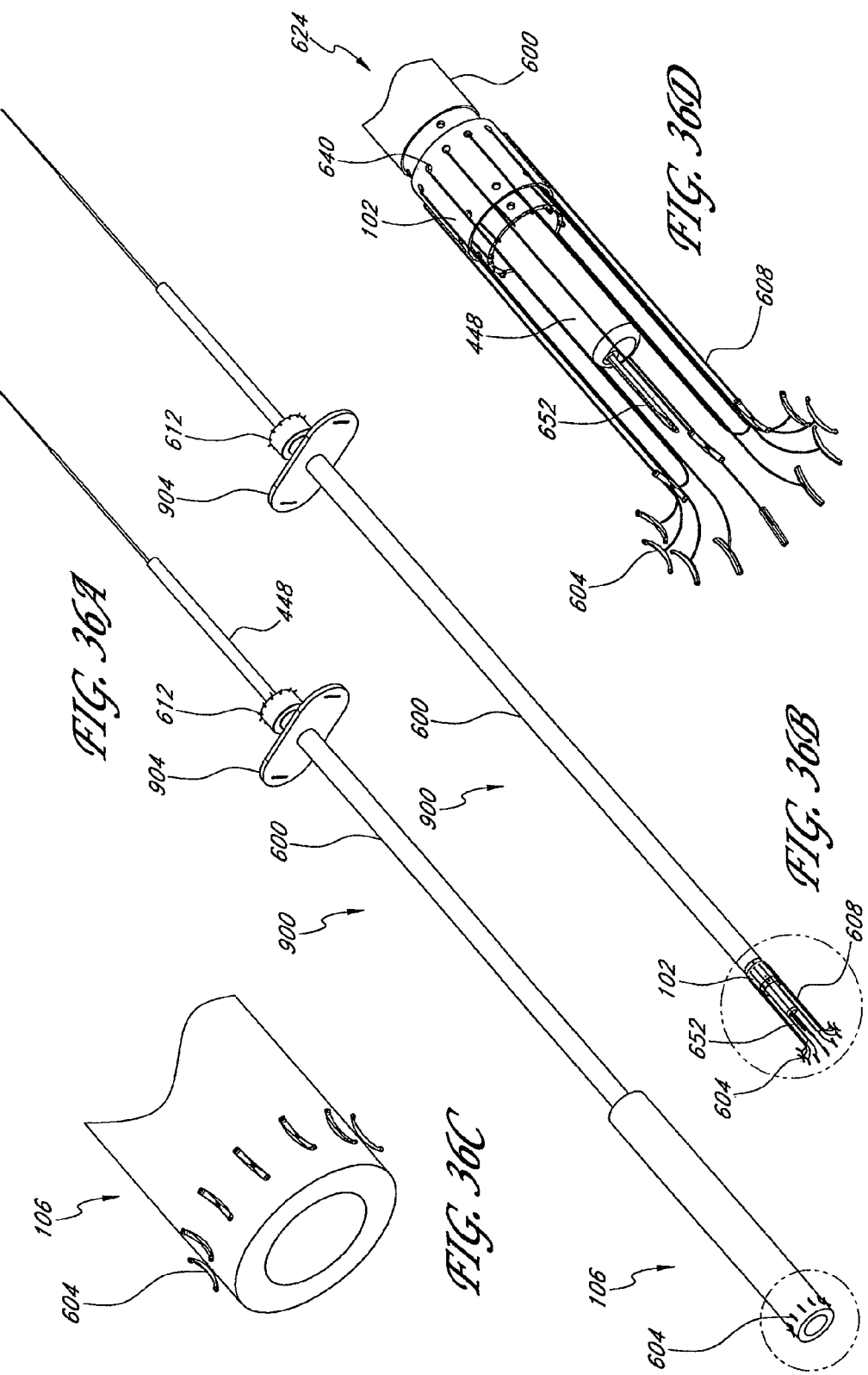

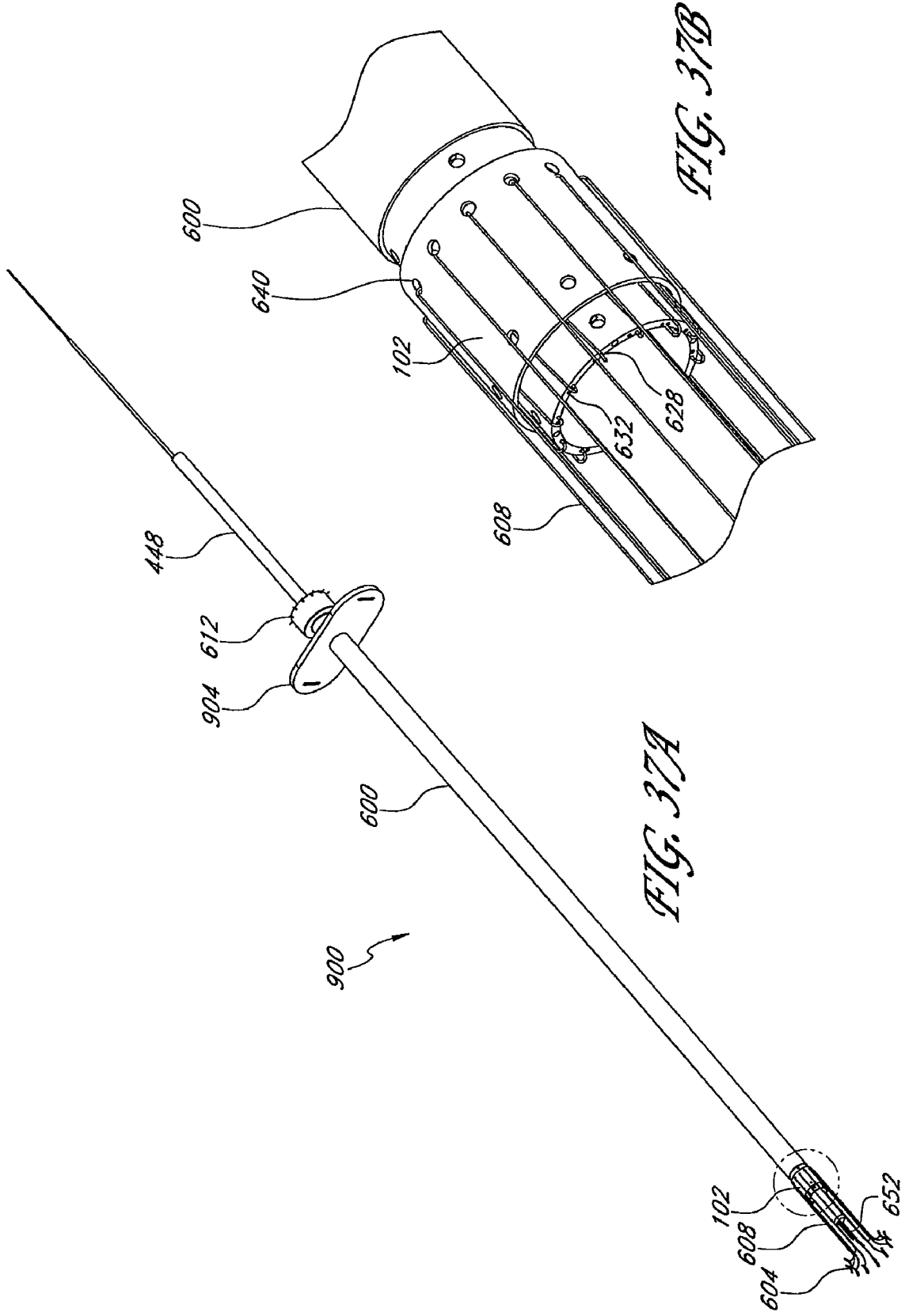

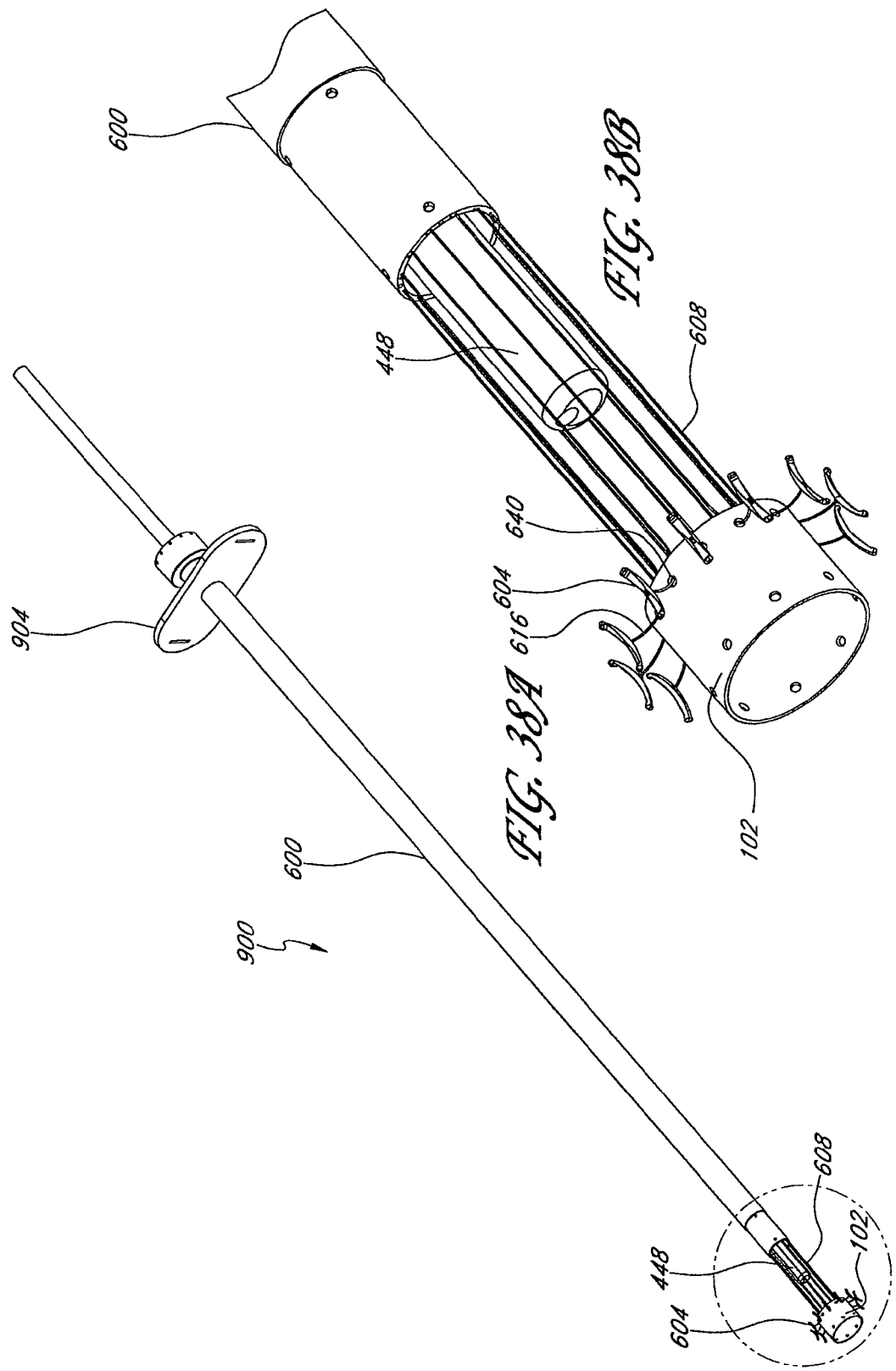

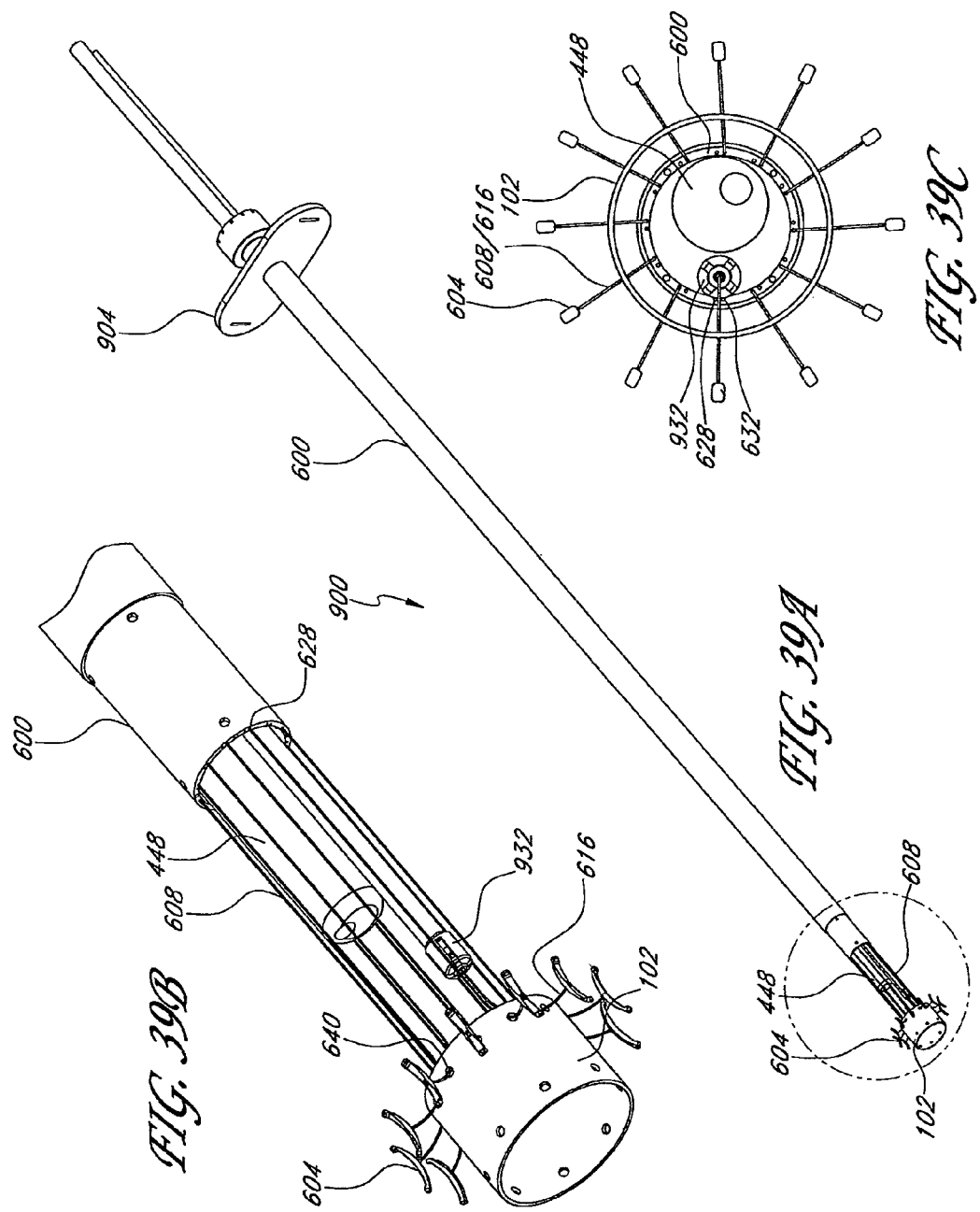

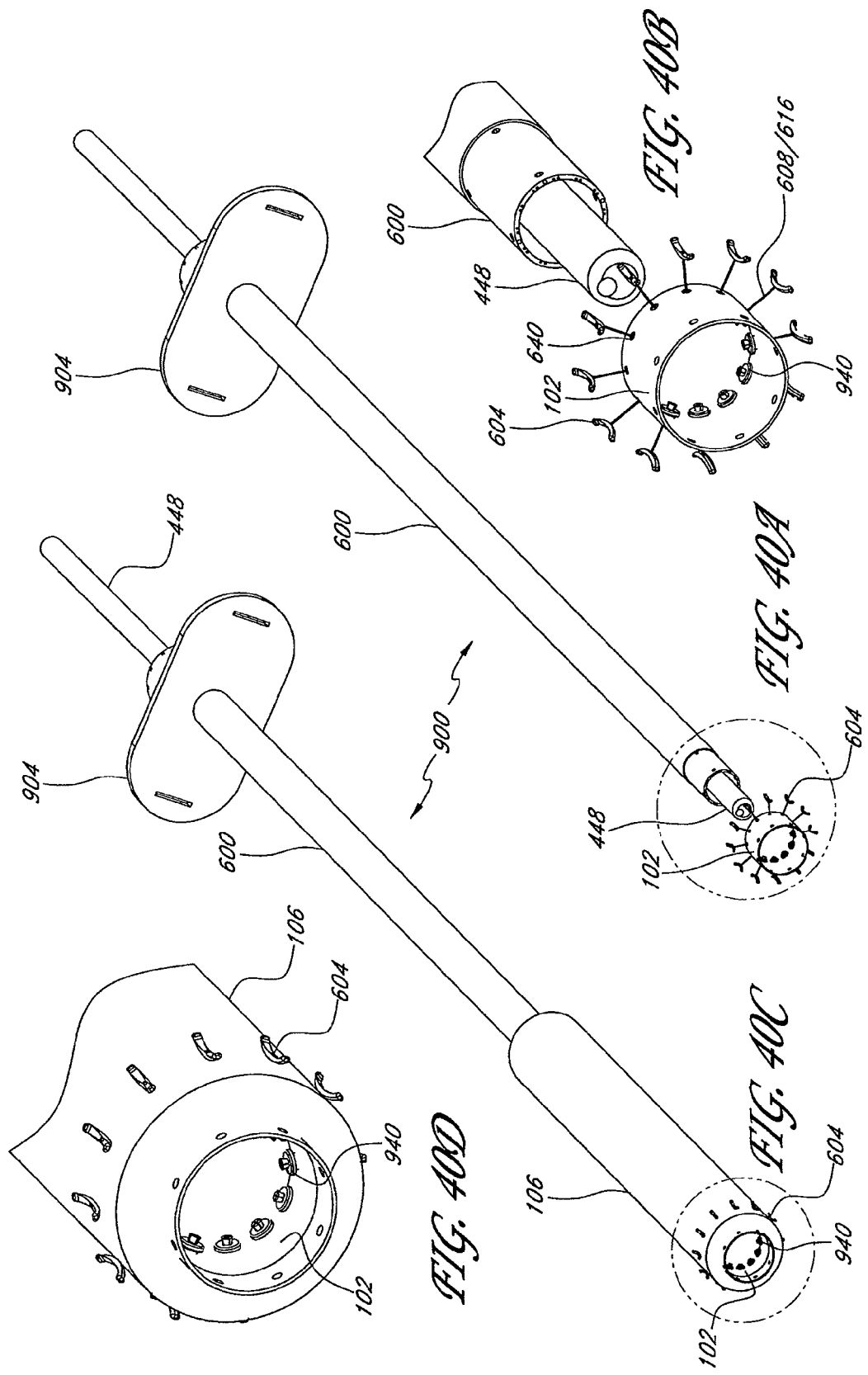

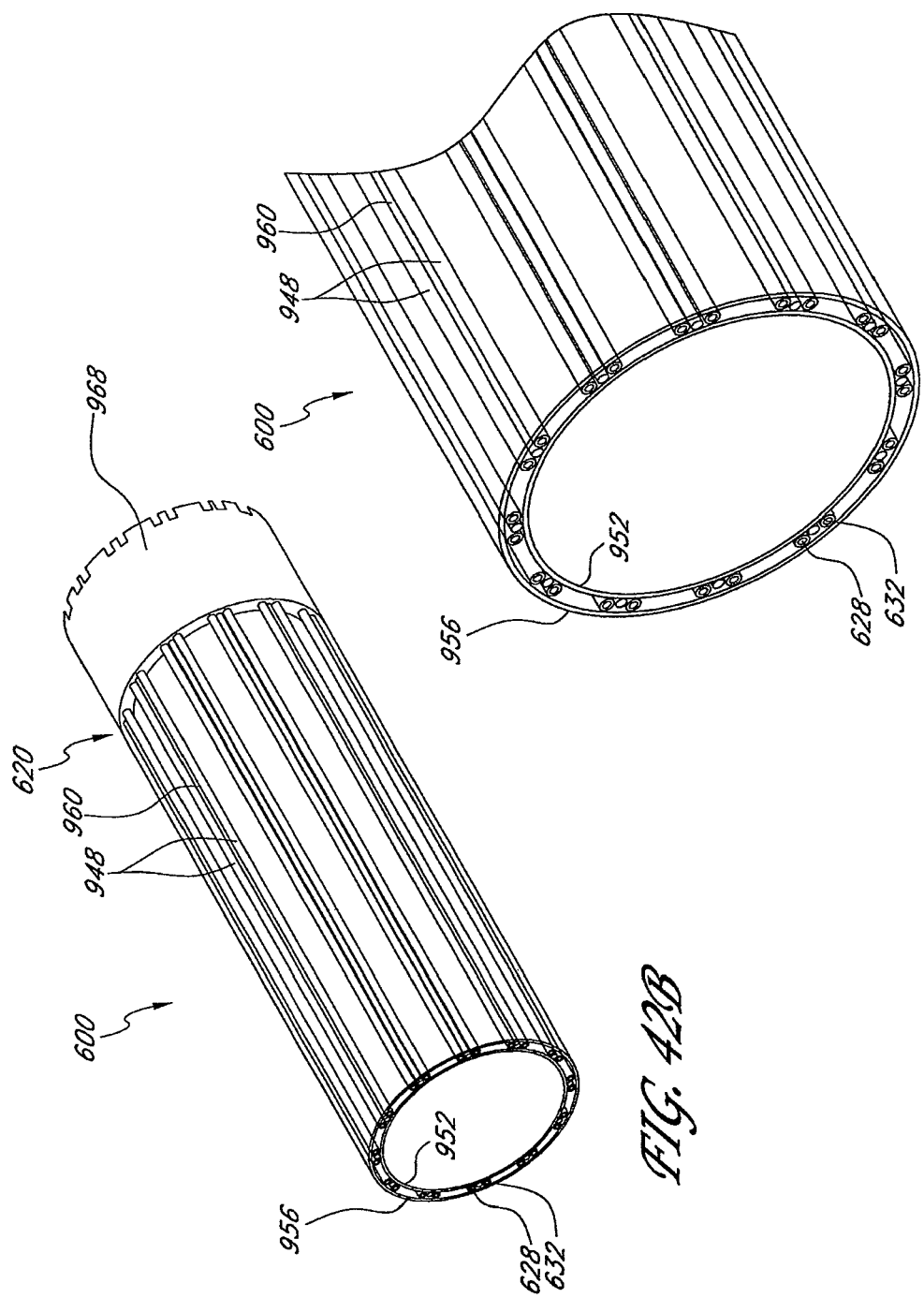

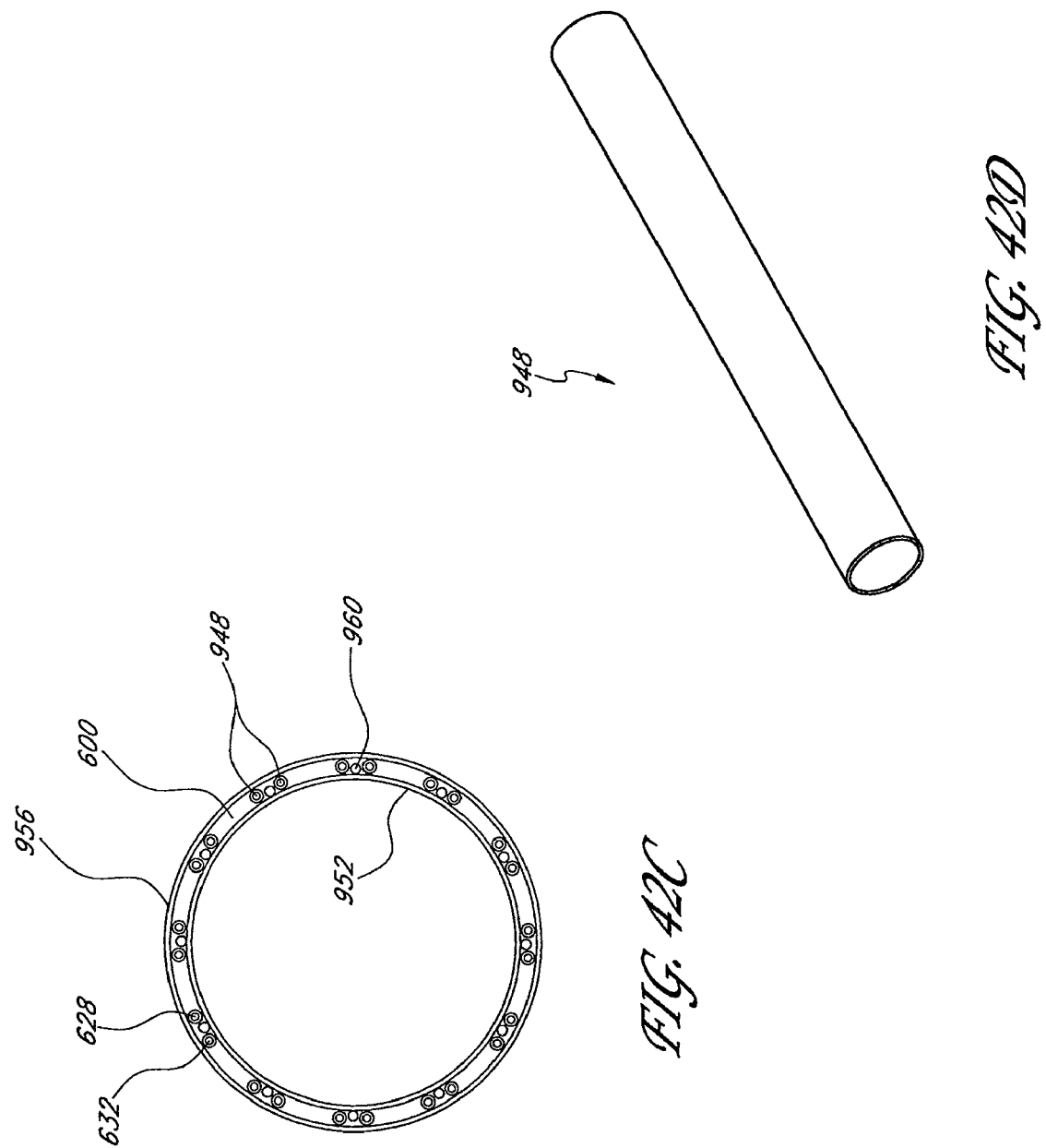

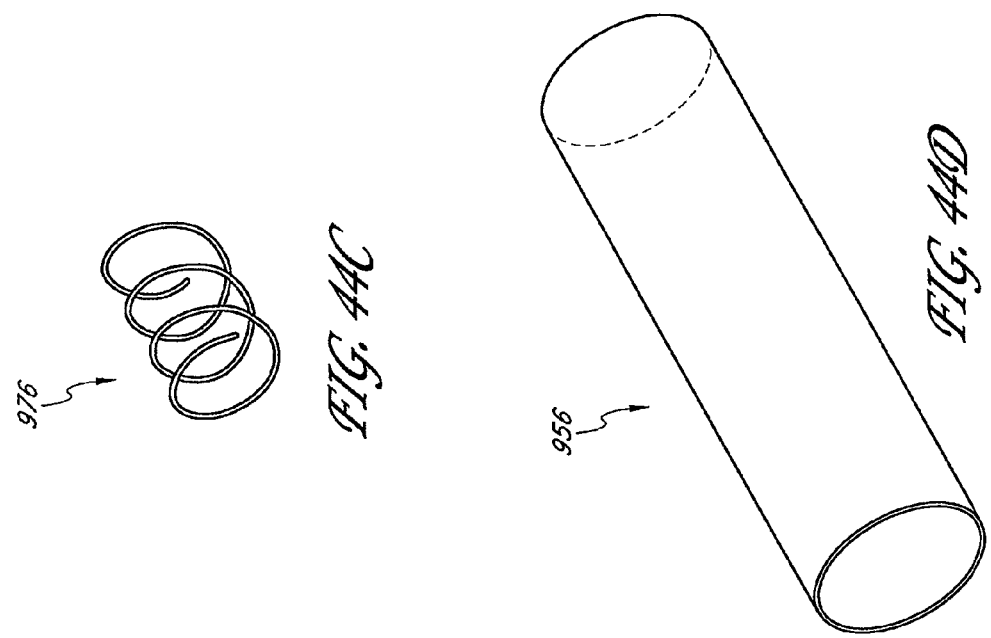
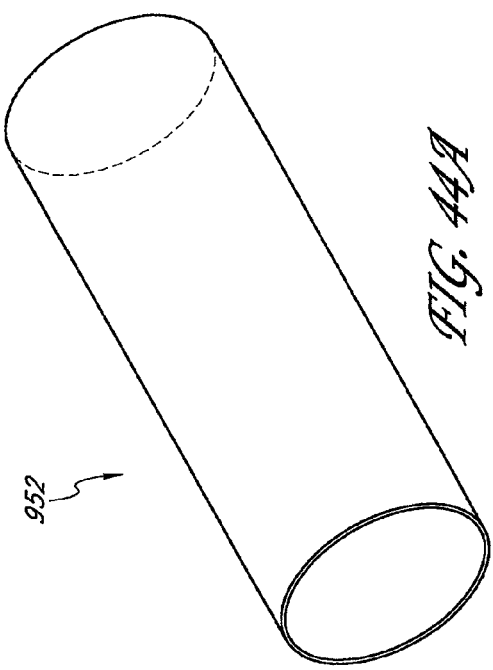
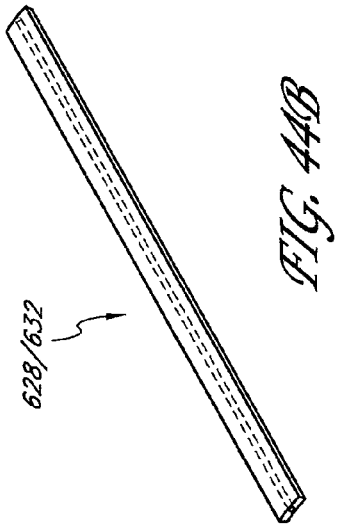

628/632

628/632

628/632

628/632

628/632

628/632

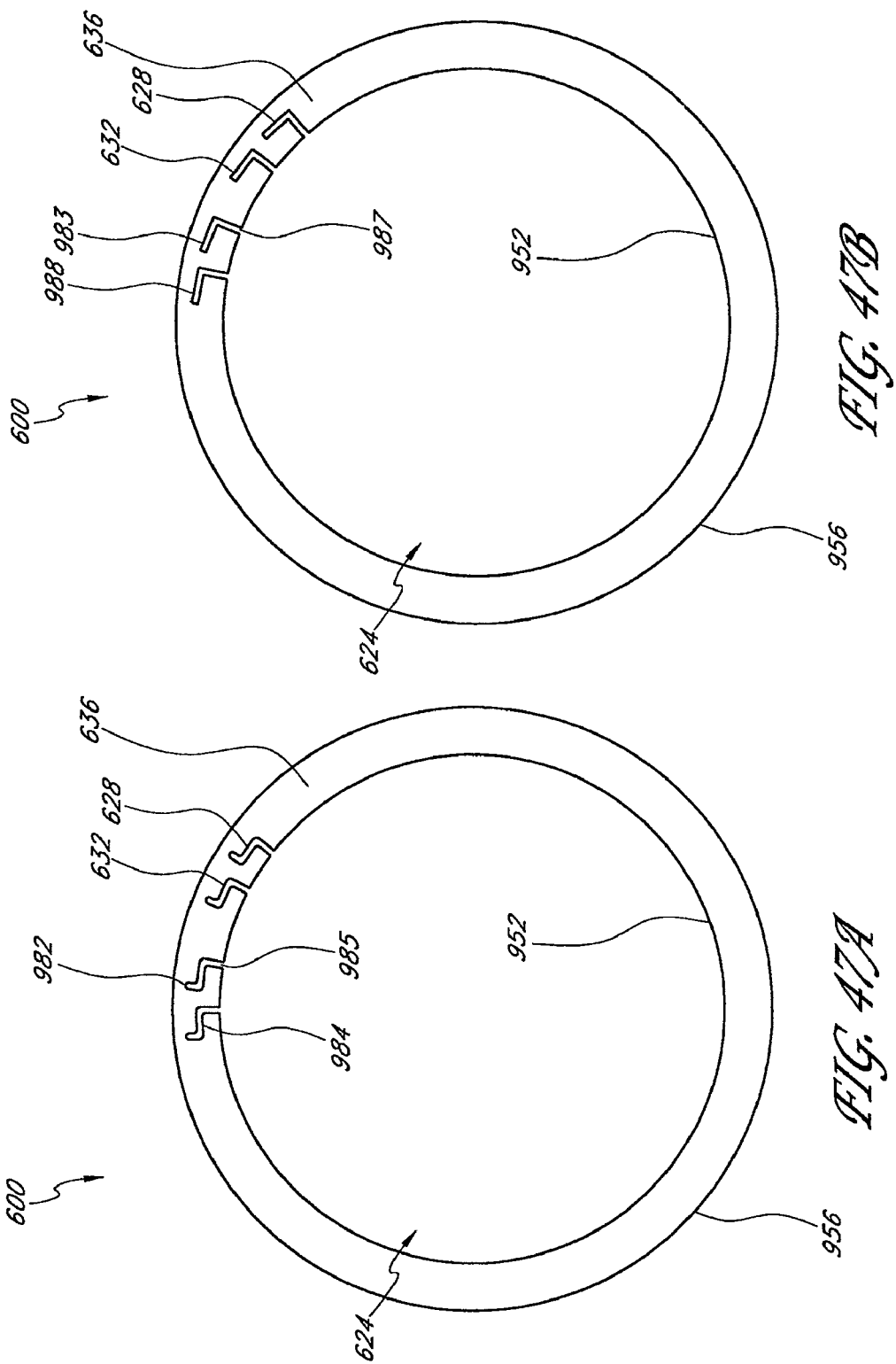

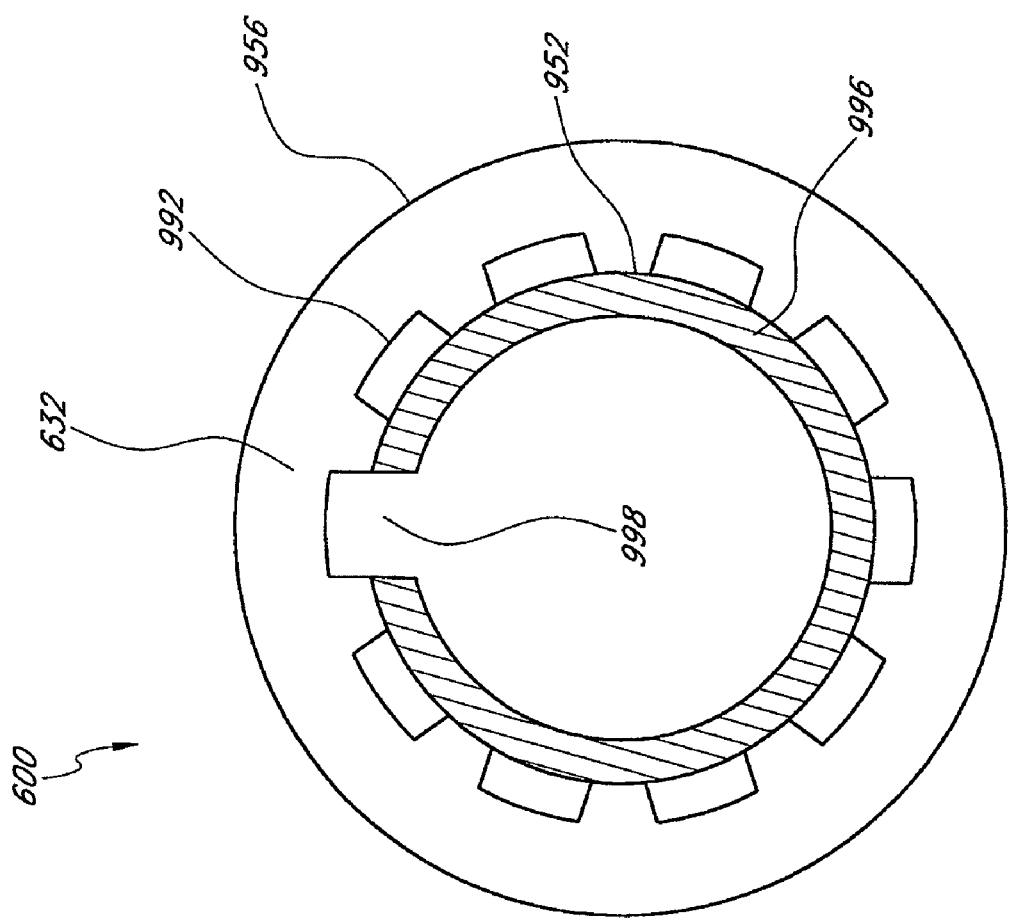

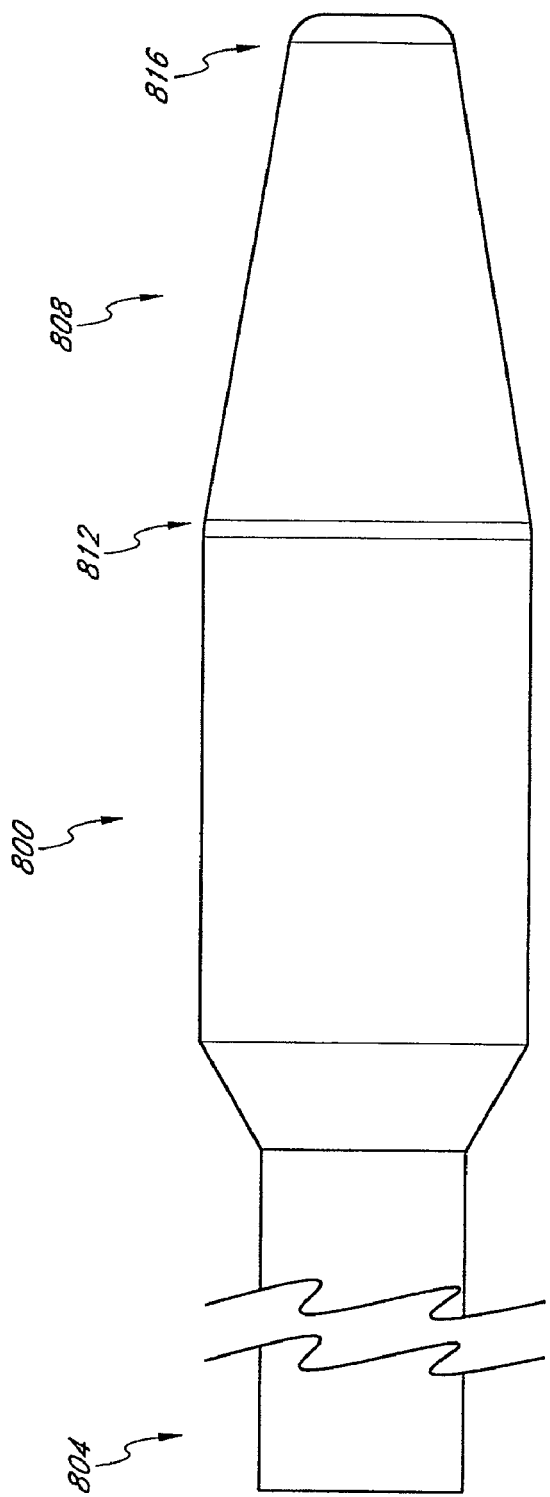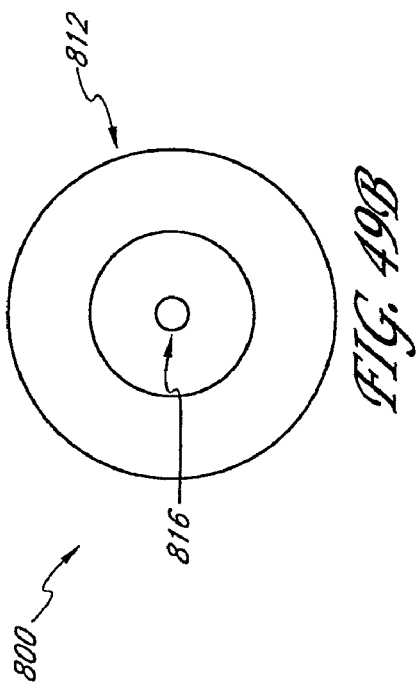

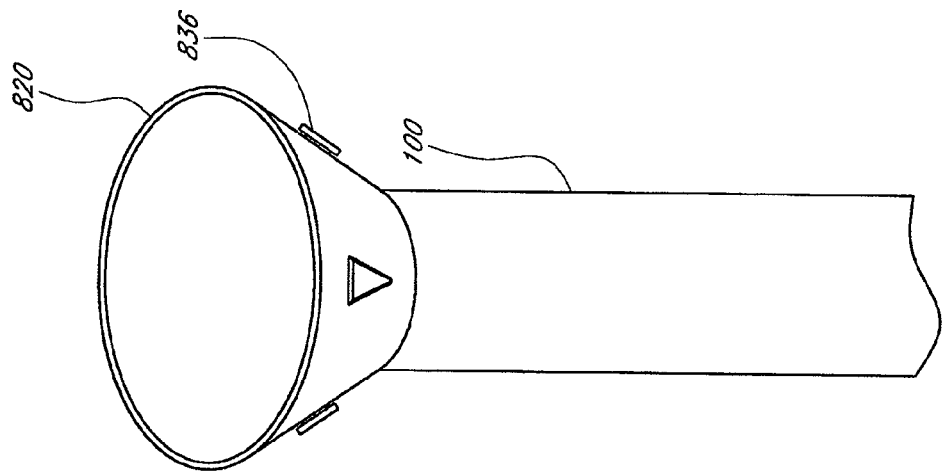
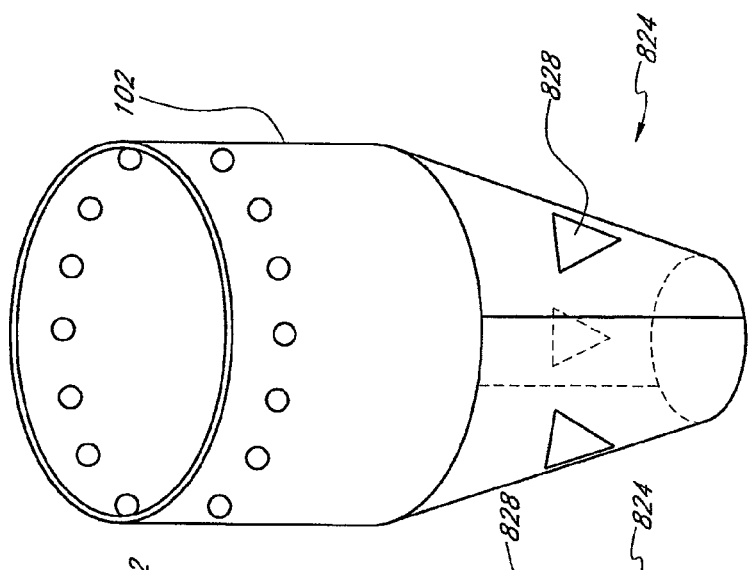
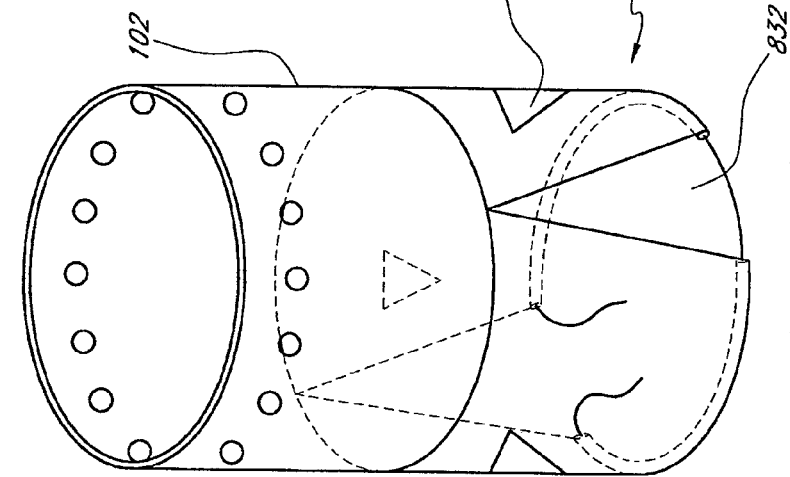

DEVICES AND METHODS FOR ENDOLUMENAL GASTROINTESTINAL BYPASS

CROSS REFERENCE TO RELATED APPLICATIONS

This patent application is a continuation-in-part of U.S. patent application Ser. No. 11/124,634 filed May 5, 2005 which claims the benefit of U.S. provisional patent application 60/569,442, filed on May 7, 2004, by Kagan et al. for Devices and Methods for Treating Morbid Obesity and U.S. provisional patent application 60/613,917, filed on Sep. 27, 2004, by Kagan et al. for Devices and Methods for Attachment of a Gastrointestinal Sleeve. This patent application is also a continuation-in-part of U.S. utility patent application Ser. No. 10/698,148, filed on Oct. 31, 2003 by Kagan et al. for Apparatus and Methods for Treatment of Morbid Obesity which claims priority to U.S. provisional patent filed applications 60/480,485 filed Jun. 21, 2003, 60/448,817 filed Feb. 21, 2003, 60/437,513 filed Dec. 30, 2002, 60/430,857 filed Dec. 3, 2002, 60/428,483 filed Nov. 22, 2002, and 60/422,987 filed Nov. 1, 2002. This patent application is also a continuation-in-part of U.S. utility patent application Ser. No. 10/998,424, filed on Nov. 29, 2004 by Kagan et al. for Apparatus and Methods for Treatment of Morbid Obesity and U.S. utility patent application Ser. No. 11/025,364, filed on Dec. 29, 2004, by Kagan et al. for Devices and Methods for Treating Morbid Obesity. The devices and methods described herein can be combined with and/or used in conjunction with the apparatus and methods described in these prior applications. These and all patents and patent applications referred to herein are hereby expressly incorporated by reference in their entireties herein.

BACKGROUND OF THE INVENTION

1. Field of the Invention

The present invention relates to devices and methods for attachment of a device within a patient's digestive tract. In particular, the present invention relates to devices and methods for treatment of obesity and/or its comorbidities, such as diabetes.

2. Description of the Related Art

Bariatrics is the field of medicine encompassing the study of overweight, its causes, prevention and treatment. Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found in U.S. Provisional Patent Application No. 60/422,987 Apparatus and Methods for Treatment of Morbid Obesity and also on the website of the American Society for Bariatric Surgery.

Medical sleeve devices for placement in a patient's stomach are described by Rockey in U.S. Pat. Nos. 4,501,264, 4,641,653 and 4,763,653. The medical sleeve described in these patents are said to reduce the surface area available for absorption in the stomach, however it is not configured to effectively reduce the volume of the stomach nor will the device described isolate ingested food from stomach secretions. Other sleeve devices for placement in a patient's intestines are described in U.S. Pat. No. 4,134,405 (Smit), U.S. Pat. No. 4,315,509 (Smit), U.S. Pat. No. 5,306,300 (Berry), and U.S. Pat. No. 5,820,584 (Crabb). The sleeve devices described in these patents are said to be placed at the lower end of the stomach and therefore do not serve to isolate ingested food from the digestive secretions of the stomach.

In U.S. Patent Application US 2003/0040804, Stack et al. describe a satiation device to aid in weight loss by controlling feelings of hunger. The patent application describes an antral tube that expands into the antrum of the stomach to create a feeling of satiation. In U.S. Patent Application US 2003/0040808, Stack et al. describe a satiation device for inducing weight loss in a patient includes a tubular prosthesis positionable such that an opening at its proximal end receives masticated food from the esophagus, and such that the masticated food passes through the pouch and into the stomach via an opening in its distal end.

In U.S. Patent Application US 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. Patent Application US 2003/0144708, Starkebaum describes methods and systems for treating patients suffering from eating disorders and obesity using electrical stimulation directly or indirectly to the pylorus of a patient to substantially close the pylorus lumen to inhibit emptying of the stomach.

Notwithstanding the foregoing, there remains a need for a perorally deployable device for the treatment of obesity and/or its comorbidities, as well as a way to attach the device and to position a bypass tube within the intestine.

SUMMARY OF THE INVENTION

There is provided in accordance with one aspect of the present invention, an attachment system for attaching a device to the mucosal side of a wall of the gastrointestinal tract. The wall comprises, among other tissue layers, a muscularis layer and a serosal layer. The system comprises a gastrointestinal attachment cuff having a tubular body, a proximal end and a distal end. At least one attachment structure (sometimes referred to as a tissue anchor) is provided for transmural attachment of the cuff to the mucosal side. The anchor comprises a connecting element (sometimes referred to as a tension element) for extending through the wall and at least one transverse retention surface for positioning in contact with the serosal tissue. The cuff may be a unitary annular component or assembly, or may comprise two or three or more components spaced circumferentially apart about a longitudinal axis.

The tension element may comprise a suture. The tension element comprises a proximal end for extending through the mucosal layer and a distal end for carrying the transverse retention surface. The transverse retention surface comprises a proximal surface of a serosal anchor. The serosal anchor may comprise a T-tag, a disk, or an inflatable structure. The serosal anchor is transformable between a first, reduced profile for distal transmural advancement through the wall, and a second, enlarged profile for resisting proximal retraction through the wall.

The tension element has a length between the cuff and the transverse retention surface, and the length is generally at least about 2 mm and often no more than about 20 mm. In some implementations of the invention, the length is within the range from about 2 mm to about 10 mm and, depending on the patient, potentially within the range from about 3 mm to about 6 mm. Preferably, the connecting element is at least as long as the uncompressed wall thickness of the tissue at the attachment point.

The attachment system may additionally comprise a first engagement surface carried by a first coupler on the attachment cuff for coupling to a second, complementary engagement surface carried by a second coupler on a gastric bypass tube. The first and second couplers may be configured for removable coupling or permanent coupling between the bypass tube and the cuff. The bypass tube may have a length of at least about 50 cm, at least about 75 cm and in certain embodiments at least about 100 cm. The length is generally at least long enough to place the distal end beyond the pylorus, and, preferably, beyond the ligament of Treitz. The system may comprise at least 6 tissue anchors, and, in some applications, at least 12 tissue anchors.

The cuff may be omitted and the proximal end of the bypass tube may be attached directly to the adjacent tissue. The use of a cuff may be preferred, however, if removal or replacement of the bypass tube is contemplated, or if it is desirable to separate the steps of tissue attachment and bypass tube placement.

There is provided in accordance with another aspect of the present invention, a method of attaching a device to the mucosal side of a wall of the gastrointestinal tract, the wall comprising a muscularis layer and a serosal layer. The method comprises the steps of providing a tension element, having a retention element thereon. The retention element is advanced through the wall from the mucosal side and the retention element is placed such that it is spaced apart from the muscularis by serosal tissue, and placed on the serosal surface. The device is directly or indirectly (e.g. through a grommet, with intervening connectors, etc) attached to the tension element, such that the device is positioned adjacent the mucosal surface. As used herein, mucosal surface is a term of directional orientation and refers to the tissue surface facing the interior of the body lumen such as the lower esophagus or stomach, which may be covered by a mucosal layer.

Changes may be caused to the serosal or other tissue following the attaching step. The changes may be caused to the tissue prior to the attaching step. The changes may be caused to the tissue as a biological response to tension on the tension element, biasing the retention element against the serosal surface. Alternatively, the changes may be caused to the serosal tissue in response to the application of an active agent. The active agent may comprise a growth factor, a sclerosing agent, or other agent or process for increasing the tissue density (e.g. initiating a fibrotic response) of the serosal tissue residing between the retention element and the muscularis.

In accordance with a further aspect of the present invention, there is provided a method of treating a patient. The method comprises the steps of providing a gastrointestinal attachment cuff having a tubular body, a proximal end and a distal end. The gastrointestinal cuff is positioned in the patient's digestive tract adjacent a mucosal surface in the vicinity of the gastroesophageal junction, the mucosal surface separated from a serosal surface by a wall thickness. The gastroesophageal cuff is secured adjacent the mucosal surface by advancing at least three tissue anchors through the mucosal surface, across the wall thickness and through the serosal surface to position a transverse retention surface of each tissue anchor in contact with the serosal surface. Preferably, the foregoing steps are accomplished endoscopically.

The securing step may comprise advancing at least 6 tissue anchors through the mucosal surface, and, in certain applications, at least 12 tissue anchors.

The tissue anchor comprises a tension element such as a suture for connecting the transverse retention surface to the cuff. The transverse retention surface may be a surface on a T-tag, a disk, or other retention structure. The length of the tension element may be at least about 75% of the wall thickness between the mucosal surface and the serosal surface. Preferably, the length of the tension element is at least about 95% of the wall thickness, and, optimally, the length of the tension element is at least about equal or greater than the wall thickness. In one embodiment the length of the tension element is at least about 120% of the wall thickness.

The method may additionally comprise the step of providing an elongate flexible gastric bypass tube having a proximal end and a distal end, and attaching the proximal end to the cuff. The proximal end of the bypass tube may be attached to the cuff endoscopically. The attaching the proximal end of the bypass tube to the cuff step may comprise removably attaching the proximal end of the bypass tube to the cuff. The distal end of the bypass tube may be positioned in the patient's jejunum, in the patient's ileum, or in the patient's duodenum.

The flexible gastric bypass tube may additionally be provided with an optional restrictive opening. The restrictive opening may be positioned anywhere along the length of the sleeve, preferably between the GEJ and the pylorus. The restrictive opening may be provided in any of a variety of ways, such as by including an additional annular component within the tubular sleeve, providing a restrictive band or component on the exterior of the tubular sleeve, or by molding or otherwise forming the restrictive opening as an integral part of the sleeve.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIGS. 7A-7B show two views of a T-tag embodiment of a tissue anchor.

FIG. 13 is a perspective, fragmentary view of a gastrointestinal bypass sleeve connected to an attachment cuff using sutures or clips.

FIG. 14 is a perspective, cross sectional view of a gastrointestinal bypass sleeve being advanced distally through a previously attached cuff.

FIG. 15 is a perspective, cross sectional view as in FIG. 14, after the gastrointestinal bypass sleeve has been fully distally advanced into a sealing relationship with the attachment cuff.

FIGS. 20A-20D illustrate an inflatable balloon connection between a filling catheter and a toposcopic sleeve.

FIGS. 26 and 27 are schematic illustrations of releasable connection configurations between the deployment device and the toposcopic sleeve.

FIG. 29A is an end elevational view of an overtube.

FIG. 29B is a side elevational view of the overtube of FIG. 29A.

FIG. 30A is a cross sectional view of an overtube having tissue anchors mounted thereon.

FIG. 30B is a detail view of the distal end of the overtube in FIG. 30A.

FIG. 31A is a perspective view of a deployment system including an overtube configured for suture tail management, having a cuff carried thereon.

FIG. 31B is a detail view of the distal end of the system illustrated in FIG. 31A.

FIG. 31C is a side elevational view of the system illustrated in FIG. 31A.

FIG. 31D is a proximal end elevational view of the system illustrated in FIG. 31A.

FIG. 31E is a distal end elevational view of the system illustrated in FIG. 31A.

FIG. 32A is a perspective view as in FIG. 31A, with a dilator removed.

FIG. 32B is a detail view of the distal end of the overtube illustrated in FIG. 32A.

FIG. 32C is a side elevational view of the overtube assembly illustrated in FIG. 32A.

FIG. 33A is a perspective view of the overtube having an endoscope extending therethrough.

FIG. 33B is a detail view of the distal end of the system illustrated in FIG. 33A.

FIG. 33C illustrates an alternate cuff attachment configuration.

FIG. 34A is a perspective illustration of an anchor inserter tool positioned to advance through the overtube.

FIG. 34B is a detail view of the distal end of the overtube having a cuff attached.

FIG. 34C is a detail view of a connection between the anchor inserter tool and an anchor suture.

FIG. 34D is a proximal end perspective view of the illustration in FIG. 34C.

FIGS. 35A and 35B illustrate the anchor inserter tool extending through an endoscope positioned within the overtube.

FIGS. 36A-36D show the deployment and final spatial relationship of 12 suture anchors.

FIGS. 37A and 37B illustrate the release of the cuff from the overtube.

FIGS. 38A and 38B illustrate the cuff parachuted down the sutures towards the GEJ.

FIGS. 39A-39C illustrate a suture lock being advanced down a suture to lock the cuff in its final implantation position.

FIGS. 40A-40D illustrate deployment of the implanted cuff from the overtube.

FIGS. 42A-42D illustrate suture management details of an overtube.

FIG. 44A-44D illustrate components of an overtube.

FIGS. 47A and 47B illustrate an end view having locking slots for releasably retaining sutures.

FIG. 48 is an end view of an alternate configuration for retaining sutures in a plurality of suture channels.

FIGS. 49A and 49B illustrate a blunt obturator tip.

FIGS. 50A and 50B illustrate a cuff having a reduceable distal diameter for receiving a sleeve.

FIG. 50C illustrates the proximal end of a sleeve having complementary interfit structures or locking with the cuff of FIGS. 50A and 50B.

DETAILED DESCRIPTION OF THE PREFERRED EMBODIMENT

The present invention provides devices and methods for attaching an implant within the gastrointestinal system. Although described primarily in the context of supporting an endolumenal bypass sleeve, the attachment technology of the present invention can be utilized to support any of a variety of devices which may be desirably positioned within the stomach or elsewhere in the gastrointestinal system. For example, the attachment cuff and/or serosal anchors disclosed herein may be utilized to support any of a variety of valves or constricted openings designed to treat gastroesophageal reflux disease (GERD), by augmenting natural function of the lower esophageal sphincter or replacing that function. Any of a variety of obesity devices may also be attached to the attachment cuff and/or using the serosal anchors disclosed herein, such as electrical stimulation and/or pacing devices, or volume occupying devices which hang from or are otherwise attached to the vicinity of the lower esophageal sphincter into the stomach. Any of a variety of drug delivery reservoirs may also be stabilized within the gastrointestinal system using the cuff and/or anchoring systems disclosed herein. Diagnostic devices, such as pH detectors, analyte detectors, pressure sensors may also be temporarily or permanently secured within the gastrointestinal system using the technologies disclosed herein. The attachment cuff and/or associated serosal anchors may further be utilized to accomplish endolumenal anastomosis, or to span a defect or disease condition, such as an ulceration or other gastrointestinal anomaly.

Notwithstanding the foregoing, the present invention will be described primarily in the context of gastrointestinal sleeve devices that can mimic a Roux-en-Y gastric bypass by effectively reducing stomach volume, bypassing a portion of the stomach and/or small intestines, reducing nutrient absorption in the stomach and/or small intestines and depositing minimally or undigested food farther than normal into the intestines, thereby stimulating intestinal responses.

Figure 1:
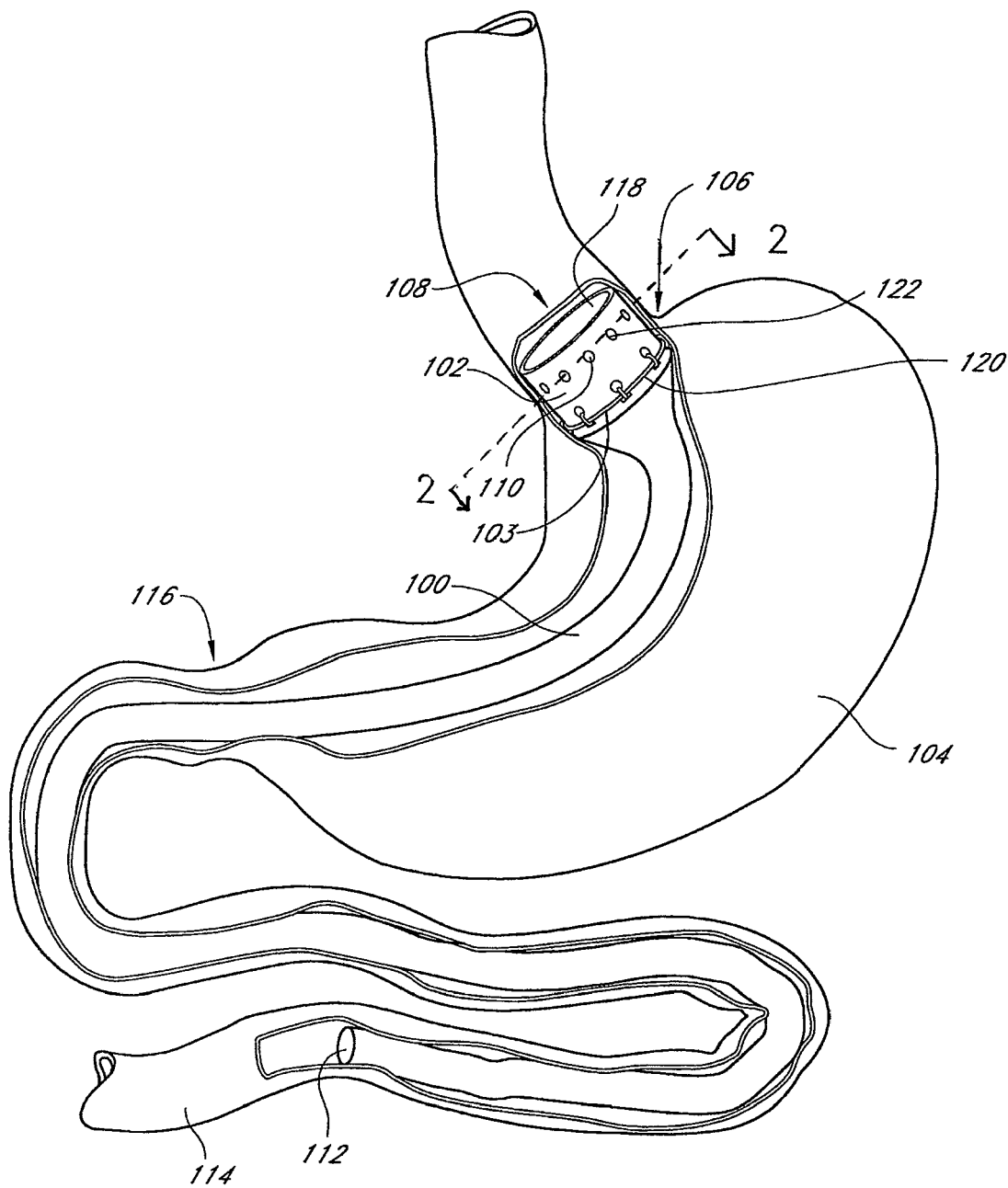
FIG. 1 shows a gastrointestinal sleeve device attached to a cuff positioned in the vicinity of the gastroesophageal junction.

FIG. 1 shows a gastrointestinal sleeve device 100 attached to an artificial attachment cuff or stoma device 102 implanted within a patient's stomach 104. The attachment cuff 102 can be implanted in the vicinity of the gastroesophageal junction 106, or at the outlet of a surgically created gastric pouch (not illustrated). The attachment cuff 102 preferably does not restrict the flow of food, although it may be provided with a restrictive opening if desired. The cuff 102 can have a fixed diameter opening 108 equal to, larger or smaller than the fully open diameter at the native GEJ. Alternatively, the cuff 102 can have an adjustable stoma opening or it can be a "smart" stoma that adjusts the size of the stoma opening in response to various conditions.

The attachment cuff 102 is preferably configured for per-oral delivery and attachment using endoscopic techniques. Alternatively, the cuff 102 can be implanted using laparoscopic or open surgical techniques. Additional details of the cuff, stoma and attachment are found below, and in the related applications previously incorporated by reference herein.

The gastrointestinal sleeve device 100 is an elongated flexible tubular structure that is permanently or removably attached to the attachment cuff 102 such that food and liquids pass through the cuff 102 and enter the internal lumen of the sleeve device 100. The attachment cuff 102 and the gastrointestinal sleeve device 100 can be implanted simultaneously, or the attachment cuff 102 can be implanted by itself and then the gastrointestinal sleeve device 100 can be attached to the attachment cuff 102 in the same or a subsequent procedure. Implantation and attachment of the sleeve can be accomplished perorally, or using laparoscopic or open surgical techniques. In a hybrid technique, the sleeve and cuff can be positioned perorally (transesophageally) and the tissue anchors (discussed below) advanced laparascopically or by surgical incision from the serosal surface through the wall of the esophagus or stomach to attach to the cuff on the mucosal side of the tissue. Optionally, a line of staples or other fasteners may be used with any of the devices disclosed herein to create a gastroplasty to reduce the volume of the stomach.

In conjunction with the cuff and/or gastric sleeve, the volume of the stomach can be reduced by suturing, stapling, adhesives or other technique using open, transesophageal or laparoscopic techniques. Alternatively or in addition, a gastric balloon or other volume displacement device may be used in conjunction with the gastric sleeve to provide a feeling of satiety. These adjunctive techniques may have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve).

Returning to FIG. 1, a gastrointestinal sleeve device 100 is attached at the GEJ with an attachment cuff 102. Tissue anchors, described below, have been omitted from FIG. 1 for simplicity. The cuff 102 may include a plurality of preformed attachment structures 110 for attachment of tissue anchors as is discussed below.

The implantable cuff and/or attachment system is preferably configured to avoid causing excessive force or pressure within the tissue by having compliance that is compatible with the gastrointestinal tissues where it is attached. Device compliance can also be important for providing a leak free seal between an implanted device and the tissue at the attachment point. Compliance can be provided in the radial or circumferential direction and/or in the vertical, axial or longitudinal direction. The device may have different compliance in different regions to be compatible with the tissue at the attachment point and at other portions of the gastrointestinal tract through which it runs. The device may have different compliance in different directions to be compatible with the tissue at the attachment point while simultaneously achieving other goals of the device. Compliance can be provided in a number of different ways. One way is by elastic or plastic deformation of the device and/or the attachment means. Another way is by a mechanical decoupling that allows relative movement between the device and the attachment points, and/or between the attachment points themselves, without transmitting excessive force or pressure to the tissue.

In some clinical situations, it will be desirable to match compliance between the device and the tissue to which it is attached. In other situations, based upon the clinical situations, it may be desirable to provide a device with higher or lower compliance than the adjacent tissue to achieve certain objectives.

Preferably, the attachment cuff 102 is highly flexible or compliant in the radial direction so that expansion and contraction of the stomach and esophagus due to contents and/or muscular action will not place additional, or actually reduce, stress on the attachment points. An elastomeric material, such as silicone or polyurethane that provides approximately 150% or more stretch in the radial direction may be used. At the same time, an attachment ring or other structure for attaching the sleeve, where utilized, may have enough lateral rigidity to act as a mounting platform for the gastrointestinal sleeve device and to resist downward movement due to the weight of the gastrointestinal sleeve device and its contents and peristaltic traction on the sleeve. The lateral rigidity of any sleeve attachment structure can be enhanced with radially oriented bending reinforcements, such as ribs or embedded reinforcement members. Alternatively, the attachment cuff can be flexible and compliant and other means such as hooks, sutures staples, etc., can be used for sleeve attachment.

Referring to FIG. 1, the attachment cuff 102 comprises a highly flexible tubular wall extending between a proximal (superior) end 118 and a distal (interior) end 120. The wall may be permeable or substantially impermeable to body fluids, and may comprise any of a variety of weave densities and/or aperture patterns either to effect flexibility, fluid transport, or to accommodate attachment as is discussed further below.

The axial length of the cuff 102 between the proximal end 118 and distal end 120 can be varied considerably, depending upon the desired attachment configuration. In general, axial lengths within the range of from about 0.25 inches to about 6 inches will be used. Axial lengths within the range of from about 0.5 inches to about 2.0 inches may be sufficient to support a detachable endolumenal bypass sleeve as contemplated herein. In general, the axial length of the attachment cuff 102 may be influenced by the desired location of the seam 103 between the attachment cuff 102 and the sleeve 100, or other device which is to be attached to the cuff 102.

The attachment cuff 102 may be constructed from any of a variety of materials which are sufficiently flexible and stable in the environment of the stomach. Suitable materials may include woven or nonwoven fibers, fabrics or extrusions using materials such as polyester velour (Dacron), polyurethane, polyamide, ePTFE, various densities of polyethylene, polyethylene terephthalate, silicone, or other materials which in the form presented exhibit sufficient compliance, stretch, strength, and stability in the gastric environment.

The inside diameter of the cuff 102 can also be varied, depending upon the desired clinical performance. For example, the cuff may be provided with a stoma or inside diameter which is less than the inside diameter of the adjacent esophagus. Alternatively, the inside diameter of the cuff 102 may be approximately equal to or even greater than the native esophagus. In general, inside diameters within the range of from about 15 mm to about 40 mm are contemplated, and often within the range of from about 20 mm to about 35 mm for use in human adults.

In the illustrated embodiment, the cuff 102 is provided with a plurality of attachment structures 110 in the form of apertures 122. These apertures 122 are provided to facilitate anchoring of the cuff 102 to the adjacent tissue. In either an endoscopic or surgical implantation, a plurality of tissue anchors will be pre-attached to, or advanced through the wall of the cuff 102 and transmurally through the adjacent tissue as is discussed elsewhere herein. Provision of a plurality of anchoring points such as apertures or other structures which facilitate positioning and/or attachment of tissue anchors may desirably help with anchor location as well as reduce the amount of force necessary to advance t-tags or other anchoring structures through the wall of the cuff 102.

In an embodiment which utilizes apertures 122 to facilitate tissue anchoring, the number of apertures 122 may correspond to or be greater than the total anticipated number of tissue anchors. In general, at least about four apertures 122 and as many as eighteen or twenty are presently contemplated, with from about eight apertures to about sixteen apertures presently preferred. In one embodiment, twelve tissue anchors are used.

Preferably, the apertures 122 in an embodiment of the cuff 102 made from a thin walled woven or non-woven material will be provided with a reinforcement ring (one reinforcing ring per aperture, or one reinforcing ring for the implant, superior to the apertures 122) to prevent pull-out of the associated anchoring structures, as will be appreciated by those of skill in the art in view of the disclosure herein. The reinforcement ring, where used, may be a separate component such as a grommet attached at each aperture to the cuff 102 such as by thermal bonding, adhesives, mechanical interference or other technique. Alternatively, particularly in the case of a fabric cuff 102, the reinforcement may be provided by stitching around the perimeter of the aperture 122 in the manner of a buttonhole as is understood in the art.

In the illustrated embodiment, each of the plurality of apertures 122 resides in a common transverse plane, positioned in the patient at or slightly above the gastroesophageal junction. Alternatively, the apertures 122 may be provided in two or three or more transverse planes, such as to permit attachment points in a zig-zag orientation around the circumference of the attachment cuff 102. For example, a first set of apertures 122 (such as every other aperture) may be axially displaced from a second set of apertures 122 by a distance within the range of from about 1 mm to about 10 mm, to provide a first and a second transverse attachment plane. Axially staggering the location of the attachment apertures 122 may be desirable depending upon the number and configuration of tissue anchors and tissue anchor reinforcement structures as may be apparent to those of skill in the art in view of the disclosure herein.

Figure 3:
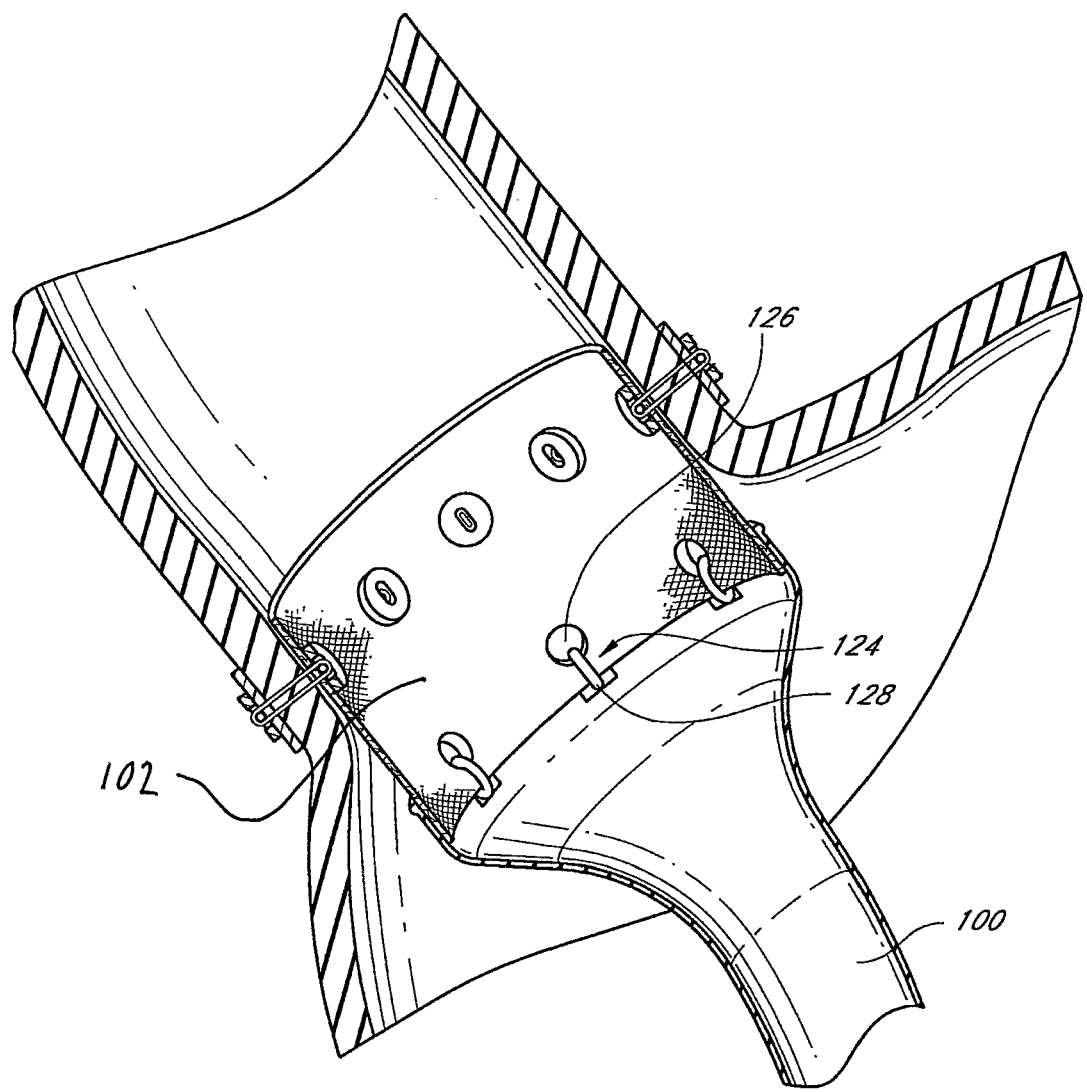
FIG. 3 is an enlarged cross sectional view of the cuff of FIG. 1.

Referring to FIG. 3, a plurality of attachment points 124 may also be provided on the cuff 102, for permanently or removably attaching the bypass sleeve 100. In the illustrated embodiment, the attachment points 124 each comprise an aperture 126 for receiving a suture hook, clip or other interference coupling, magnet assisted coupling or other link 128 to couple the bypass sleeve 100 to the cuff 102. The bypass sleeve 100 may be attached to the cuff 102 in any of a variety of ways, such as is discussed elsewhere herein. In general, the present inventors contemplate a releasable attachment between the sleeve 100 and cuff 102, to permit removal and/or exchange of the sleeve 100 as has been discussed elsewhere herein.

Figure 2:
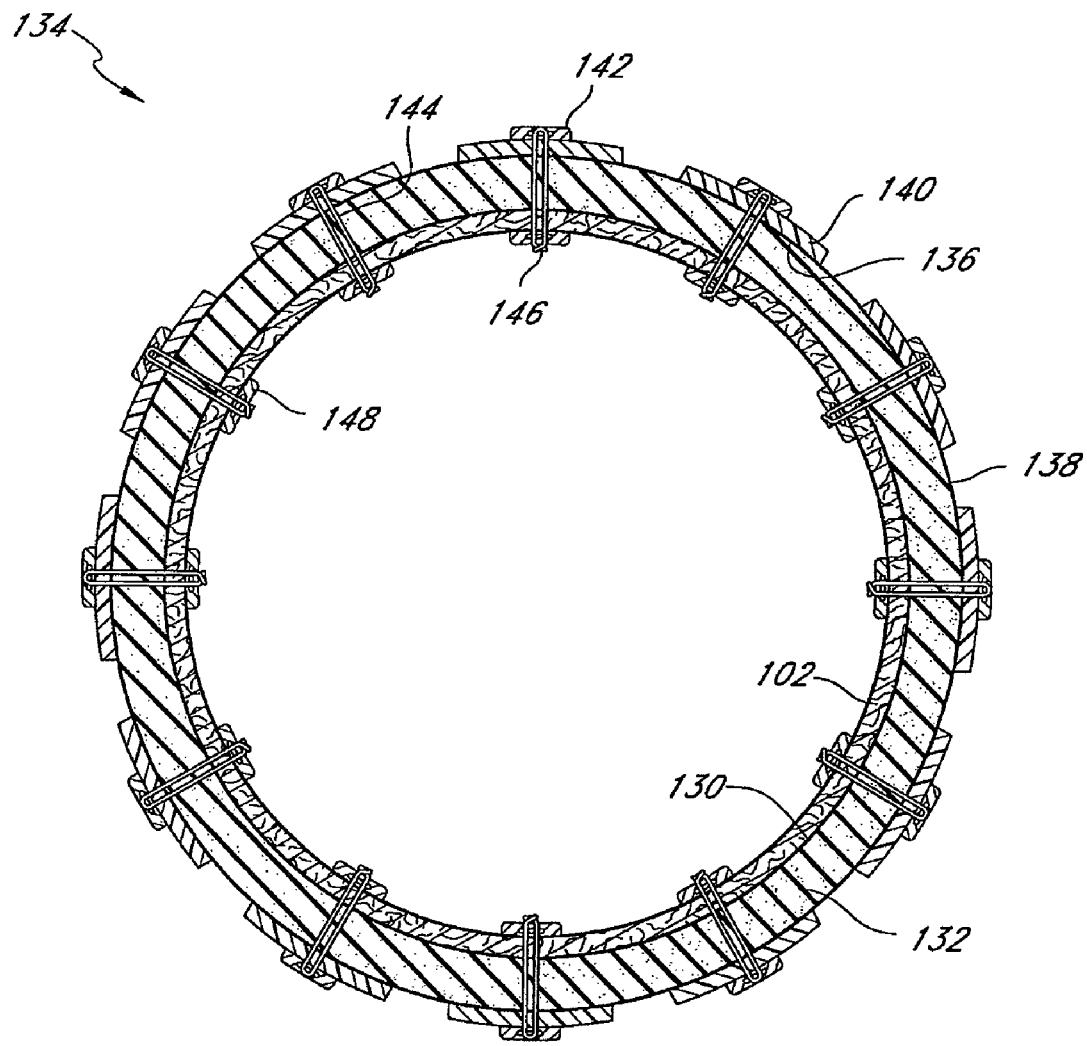
FIG. 2 is a cross sectional view taken along the line 2-2 in FIG. 1.

Referring to FIG. 2, there is illustrated a cross sectional view transverse to the longitudinal axis of the esophagus through the tissue attachment plane. Although the cuff 102 and tissue anchors appear rigidly geometric in the illustration, it is to be appreciated that the configuration will be subject to constant motion and random configuration, as the wall of the esophagus and stomach collapse and expand, with as little resistance as possible from the cuff 102 and associated attachment structures.

In FIG. 2, the cuff 102 is illustrated as snugly fitted against the mucosal surface 130 of the esophageal or stomach wall 132. A plurality of anchor assemblies 134 are shown for illustration purposes. The particular anchor assemblies 134 illustrated in FIGS. 2 and 3 may be best suited for surgical implantation, while some of the t-tag embodiments disclosed elsewhere herein may be more readily adapted for endoscopic implantation. The anchor assemblies 134 are therefore provided for illustration purposes, but should be understood as only a single example of the broader transmural, serosal surface anchoring of the present invention.

Referring to FIG. 2, the anchor assembly 134 comprises a transverse retention surface 136 for positioning against the serosal surface 138 of the esophagus or stomach wall (illustrated as a single, homogenous layer for simplicity). The transverse retention surface 136 may be a surface on a t-tag, disc, or other structure. In the illustrated embodiment, the surface 136 is carried by a small circular or oval button 140, although T-tags and other structures disclosed herein may be used, all of which are adapted to distribute force over a predetermined surface area. The button 140 may comprise any of a variety of materials, and, in one embodiment, comprises a silicone disc.

Due to the physical characteristics of silicone, a reinforcement element 142 in the form of a smaller disc or transverse structure may be embedded within, or provided on the radially outwardly facing surface of the disc 140. This reinforcement element 142 allows distribution of force from the tension element 144 across a greater surface area on the disc 140, to avoid "cheese cutter" effects or other pull through under tension exerted on the tension element 144. The desirability of including a separate reinforcing element 142 will go down, as the durometer or other rigidity characteristic of the disc 140 increases. Element 142 may comprise any of a variety of materials which will be biocompatible and generally stiffer than the disc 140, such as any of a variety of polyethylenes, PEEK, PEBAX or other materials well known in the art.

In the illustrated embodiment, the tension element 144 comprises a suture which extends from the inside of the esophagus transmurally to the reinforcing element 142 and loops back through the wall of the esophagus where it is clipped, tied, locked or otherwise secured at a connection point 146. The tension element may comprise either a single filament, or two or more filaments as illustrated, depending upon the desired installation technique and physical properties of the final construct.

A second reinforcing element 148 may also be provided, to serve the analogous function as the first reinforcing element 142, and resist pull through of the tension element 144 under the influence exerted on the implant by peristalsis and other gastrointestinal movement. The second reinforcing element 148 may be in the form of a disc, T-tag or other structure having a force distributing surface thereon. Alternatively, reinforcing element 148 may be a thickened, treated or reinforced zone on or within the wall of the sleeve. Additional details of t-tag attachment and related structures will be provided below.

Figure 4:
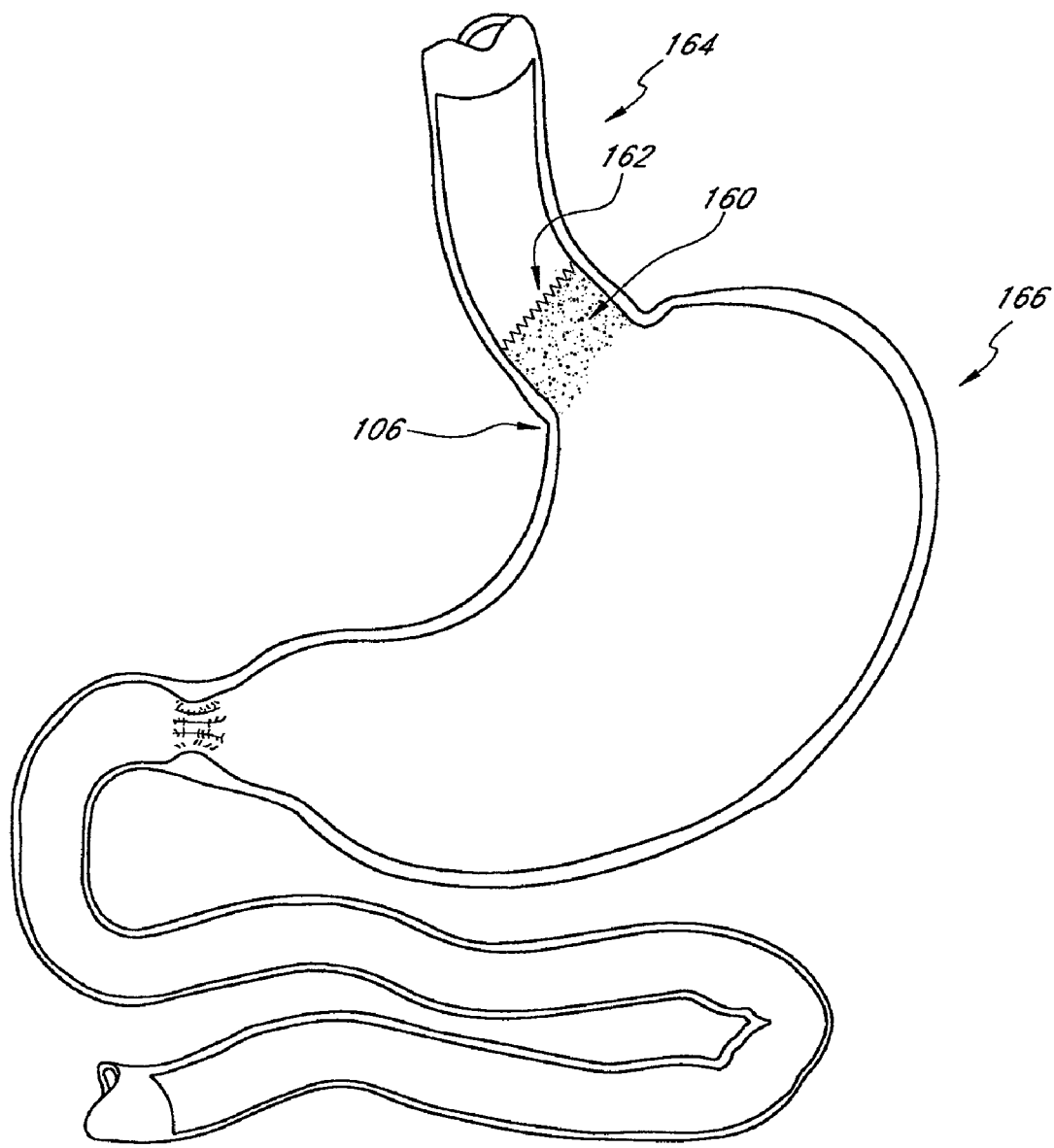
FIG. 4 shows a schematic illustration of the GEJ and the SCJ or Z-line and the target tissue zone identified by the present inventors.

The present inventors believe that some areas of the esophageal or gastric wall exhibit physical properties more conducive to retaining attachment structures than other areas. For example, an attachment zone 160, shown in FIG. 4, directly below the squamocolumnar junction (SCJ) 162, also known as the Z-line, ora serrata, and mucosal gastroesophageal junction (GEJ) 106, may be such an area. The SCJ marks the junction of the squamous mucosa of the esophagus and the columnar or glandular mucosa of the stomach. The SCJ is typically located at or above the GEJ.

The device may, in one preferred embodiment, be attached in an attachment zone 160 no more than about 2 cm and preferably no more than about 1 cm below the SCJ 162 and below the esophagus 164 where the tissue wall thickness is thicker than the tissue wall thickness of the esophagus 164 and where there exists a serosal outer surface not exhibited at the esophagus 164. The device is also preferably attached at a location in the attachment zone 160 so as to minimize the risk of reflux. The SCJ 162 can be located relative to other anatomical regions. It normally may be found at the GEJ 106. The GEJ 106 is the region at which the tubular esophagus joins the saccular stomach. The GEJ 106 can be considered the first part of the stomach 166 or the cardia and is located at the proximal margin of the longitudinal gastric mucosal folds or in the distal 2 cm of the esophagus 164 and proximal stomach 166. Endoscopically, the location of the GEJ 106 can be approximated by identifying the proximal margin of the gastric folds.

Due to patient to patient variability, as well as a variety of medical conditions, the anatomical relationships described above are not always found in all patients. For example, the location of the SCJ relative to the GEJ varies naturally patient to patient as well as due to certain medical conditions such as Barrett's esophagus.

Thus, a first aspect to the location of attachment of the devices disclosed herein relates to the position of the attachment structures along the axis of the hollow lumen or organ. As described above, the attachment location in the axial direction is preferably in the vicinity of the gastroesophageal junction, and particularly just below the SCJ. This attachment site can be located endoscopically by observing the color change which occurs at the SCJ, and advancing or positioning the attachment structures of the endoscope slightly below that line.

In some clinical situations the gastroesophageal junction, or GEJ 106, is a preferred attachment point for a gastroesophageal sleeve device or attachment device as discussed above. Attachment at the GEJ 106 excludes all gastric secretions from the interior of the gastrointestinal sleeve device to separate ingested food and liquids in the sleeve device from all digestive secretions. The gastroesophageal junction is one of the preferred attachment sites because the tissue wall is relatively thick at this location and it is relatively easy to access via a peroral route. More specifically, the area directly below the squamo-columnar junction (a zone of tissue that is considered to be at or slightly above the beginning of the GEJ 106) is currently thought to be the best place to attach a device, for example using T-tags, sutures or other fasteners.

A second aspect to the location of the attachment structure relates to the depth within the adjacent tissue wall (i.e., in a transverse direction to the longitudinal axis of the esophagus described above) within which the various anchors or retention structures disclosed herein reside. Applicants believe that the location in the transverse direction is subject to migration or other change post-implantation, as described in connection with FIGS. 5A through 5C.

Figure 5A:
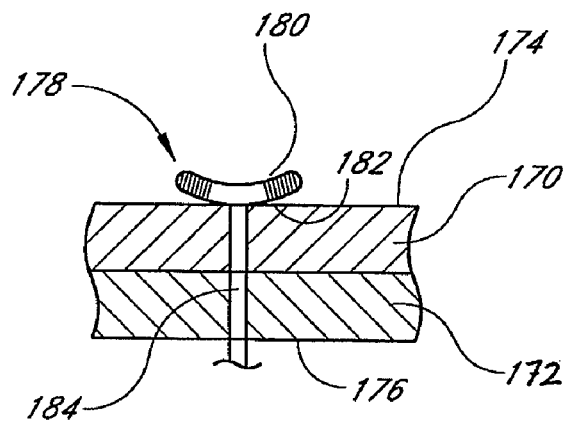
FIG. 5A shows a schematic illustration of a tissue anchor placed adjacent the serosa at the time of implantation.

Referring to FIG. 5A, there is disclosed a highly simplified schematic cross sectional view of a tissue wall such as the wall of a hollow organ or lumen in the body, including the wall at the vicinity of the gastroesophageal junction. The tissue wall comprises a serosa 170 and a muscularis 172. Additional tissue layers have been omitted for simplicity. In general, as is appreciated by those of skill in the art, the serosa 170 is on the outside of or faces away from the stomach, and the muscularis is on the inside, or faces towards the interior of the stomach. The serosa 170 thus includes a serosal surface 174 which faces away from the interior of the stomach, and the muscularis 12 includes a muscularis surface 176 which faces towards the interior of the stomach.

Figure 5B:
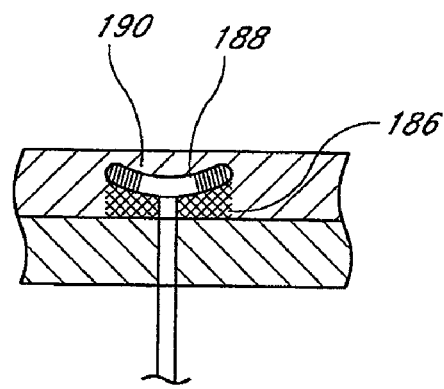
FIG. 5B shows a schematic illustration as in FIG. 5A, at a post implantation stage when the anchor has relocated into the serosa, and a layer of increased tissue density has formed on a proximal side of the tissue anchor.
Figure 5C:
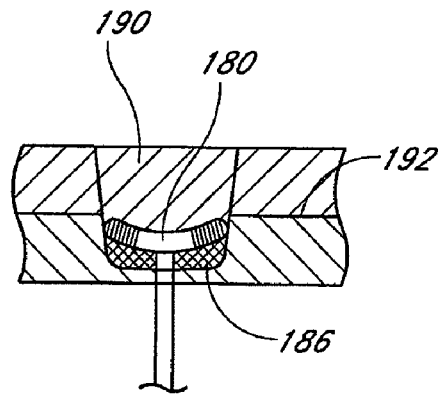
FIG. 5C is a schematic illustration as in FIG. 5B, with the anchor relocated proximally into the plane of the muscularis.

An attachment device or anchor 178 is illustrated in part in FIGS. 5A through 5C. The attachment device 178 can take any of a variety of forms, described elsewhere herein. In general, the attachment device 178 includes a retention element 180 having at least one retention surface 182 thereon. The retention element 180 may be integrally formed with or attached to a tension element 184, which extends through the tissue wall and is secured to the device implanted within the gastrointestinal tract. Although the attachment mechanisms disclosed herein will be defined primarily in the context of an obesity device, which is attached in the vicinity of the GEJ 106, those of skill in the art will appreciate that the attachment system disclosed herein may be utilized in any of a wide variety of other anatomical locations, such as in the bronchial tubes, urethra, ureters, fallopian tubes, throughout the GI tract, and others which share a serosa or serosa like layer, such as in the kidney, bladder, and other organs, as would be recognized by those skilled in the art.

Referring to FIG. 5A, the retention element 180 is illustrated with the retention surface 182 residing against the serosal surface 174. Retention surface 182 may comprise any of a variety of forms, such as a proximal surface on a T-tag, proximal surface on a washer or disc, or any other surface which extends in a generally lateral direction with respect to a longitudinal axis of the tension element 184. The transverse retention surface 182 may be radially enlargeable or expandable from a first, reduced cross-sectional configuration to provide a low crossing profile such as for deployment through a deployment cannula, and a second, radially expanded or enlarged cross-sectional profile as illustrated in FIG. 5A, to provide a retention surface 182 which will engage or interfere with tissue of the serosa 170 or muscularis 172 to resist proximal retraction of the attachment device 178 through the tissue. Transformation between the first configuration and second configuration can be accomplished in any of a variety of ways as is discussed further herein, such as by pivoting the retention element 180 about the attachment point to tension element 184, by radial expansion, by inflation, or other technique.

Tension element 184 may comprise any of a variety of connectors or elements adapted to extend through the tissue wall, such as a suture, or other single stand or multi-strand filament or material. In some embodiments the tension element 184 is formed of a polymer such as PEEK or silicone. The tension element 184 may also, in some embodiments, have elastic properties. In other embodiments the tension element 184 does not have elastic properties. By use of the term tension element, no specific mechanism is suggested, and the element is not required to be under mechanical tension.

The attachment device, otherwise sometimes referred to herein as a tissue anchor, T-tag or other label, it is illustrated in FIG. 5A in a schematic fashion as it may appear at the time of implantation. Since in certain implementations of the invention the length of the tension element 184 will exceed the uncompressed thickness of the adjacent tissue wall, the retention surface 182 may even be spaced slightly apart from the serosal surface 174 depending upon the transient motion or configuration of the stomach at any given time.

Without being limited to any particular structure or mechanism, Applicants believe that the presence of the attachment device may cause or accelerate the formation of a layer 186 of serosal tissue having increased tissue density relative to unaffected or normal serosal tissue. The layer of increased density 186 may result from a process in which the transverse retention surface 182 places pressure against the serosa 170, causing a localized necrosis due to the restriction of capillary blood flow. The necrosed tissue thereafter fibroses, as a part of a normal healing response. The layer of increased density 186 or fibrosis may also result from a foreign body reaction triggered by the presence of the transverse retention surface 182. Applicants have observed a greater degree of fibrosis or denser tissue on the side of the T-tag facing the lumen of the stomach, for example on the retention surface 182.

In certain animal trials conducted by Applicants in which the animals were sacrificed five weeks following implantation of the attachment device 178, successful anchors appeared similar to the simplified schematic illustration of FIG. 5C. In this illustration, the location of the retention element 180 has changed relative to the serosa 170 and muscularis 172, and the distal surface 188 of the retention element 180 has been covered with an overgrowth of serosal tissue 190. A fibrotic layer 186 is positioned in between the retention surface 182 and the muscularis 172. Although illustrated only on the proximal side of the retention element 180 where the greatest degree of fibrosis has been found to occur, the fibrotic response appears to some extent to surround and wall off the entire retention element 180.

It appears to the present inventors that formation of a sufficient fibrotic response on the proximal side of the retention surface 182 decreases the likelihood that the attachment device 178 will relocate to the inside of the stomach under normal agitation of the stomach, changes in the thickness of the stomach wall, and other conditions normally occurring in the stomach. A similar response is schematically illustrated in FIG. 5C, in which the layer 186 of high density serosal tissue remains on the proximal side of the retention element 180, however one or both of the layer 186 and retention element 180 have relocated to below the normal plane 192 separating the serosa 170 from the muscularis 172 and will remain there.

It appears to the present inventors that if the device design and/or retention element 180 design are such that in normal use the retention element 180 relocates to a position in the muscularis 172 and past the serosa 170 before a sufficient fibrotic response, the retention element 180 may relatively easily pass through the muscularis 172 and failure will result. Thus, it may be desirable in certain implementations of the invention to facilitate or accelerate the formation of the fibrotic layer 186. This may be accomplished in any of a variety of ways which will be appreciated by those of skill in the art in view of the present disclosure, such as by the introduction of an active agent which will trigger a fibrotic response. Suitable active agents may include any of a variety of growth factors, and/or chemical sclerosing agents which are well known for other medical applications. The surfaces of the retention element and tension element may also be provided with an anti-bacterial characteristic, such as by eluting an antibiotic agent, or having a bacteriostatic or bacteria inhibiting coating. Drug eluting coatings are well understood in the coronary stenting arts, and can be adapted for use in the present context by those of skill in the art.

Active agents may be applied as a coating to the retention surface 182 or retention element 180, or may be impregnated into the material of retention element 180 and/or tension element 184, such as to permit a timed release into adjacent tissue. Incorporation may be accomplished by loading the active agent into tortuous pathways or pores exposed to the surface of the retention element 180, or by inclusion in a bioabsorbable or bioerodable carrier attached to or positioned in the vicinity of the retention surface 182. Energy sources may also be utilized, such as to generate heat or otherwise stimulate formation of a fibrotic response, as is discussed further below. Formation of the fibrotic layer 186 may also be facilitated by mechanical means, for example, in one embodiment, by roughening the retention surface 182 with the addition of fibrotic layer enhancement structures such as a plurality of bumps or etched lines.

Figure 6B:
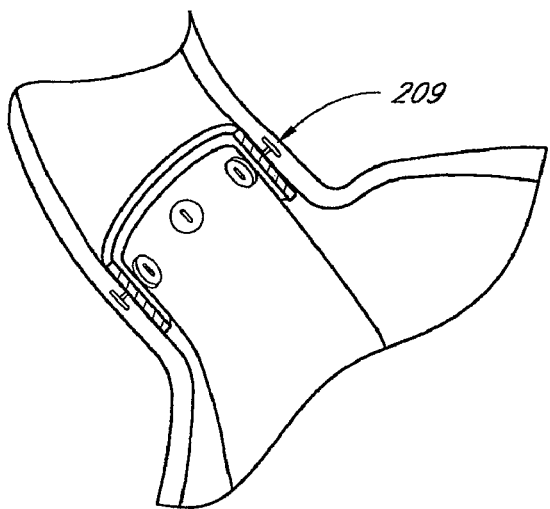
FIGS. 6A-6B show an attachment cuff attaching a gastrointestinal sleeve device using T-tags secured with a button.
Figure 6A:
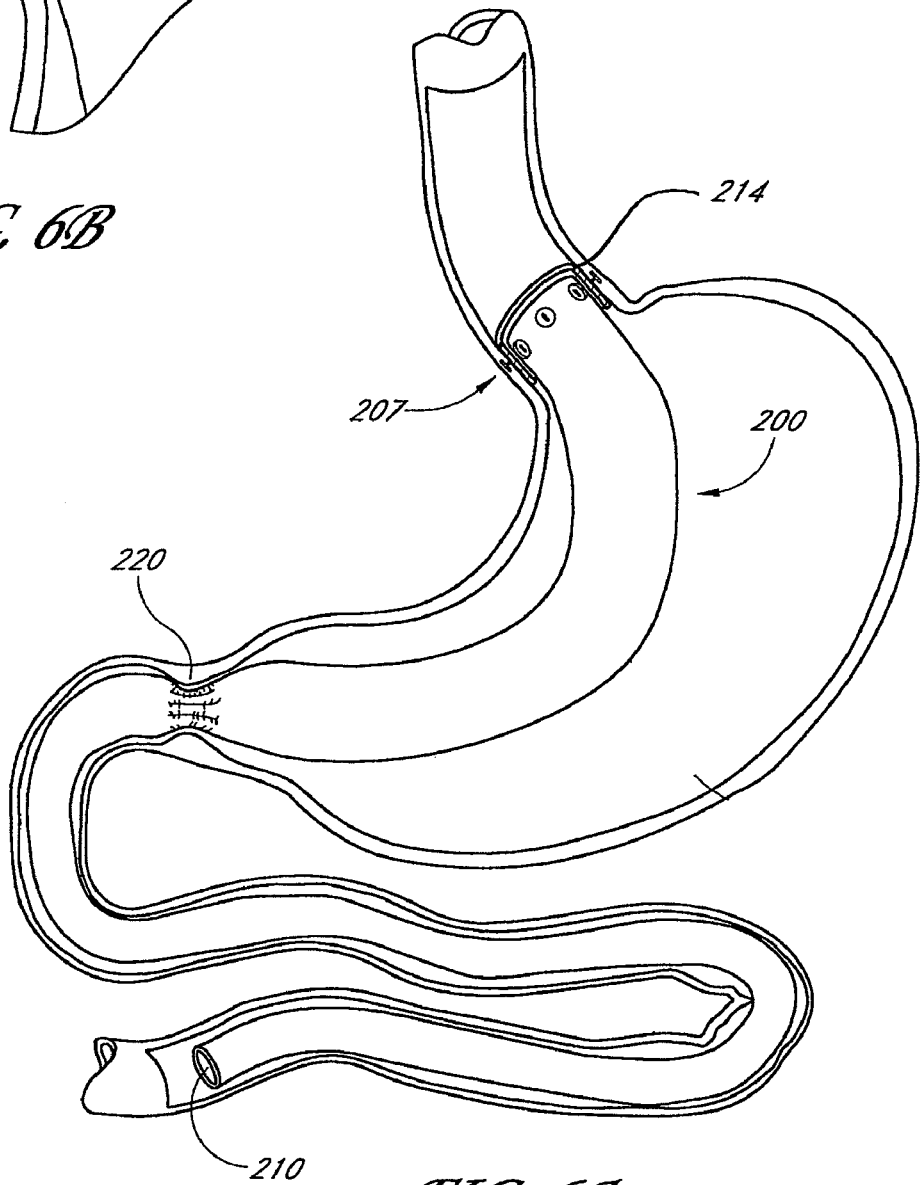

FIG. 6A shows an implanted gastrointestinal sleeve device 200 attached by an attachment cuff 214 with the use of T-tags 207. FIG. 6B is an enlarged view of the attachment cuff 214 attached with T-tags 207 showing the transverse retention elements 209 of the T-tags 207 embedded in the stomach wall, as may be observed several weeks post implantation.

T-tag type fasteners can be used endoscopically to attach many of the structures described herein. A T-tag is basically a retention element 180 in the form of a cross member or "T" that is attached to a tension element 184 in the form of an elongated member or tail at or near the mid-point of the T. A "stem" may be a structure at the joining point of the T and tail. From the perspective of a peroral attachment technique, in which the attachment devices are preferably advanced through muscularis 172 in the direction of the serosa 170, the stem or tension element will be referred to herein as relatively proximal to the cross member on the T-tag. The T-tag is a member of a more general family of tissue anchors, in which a proximally facing surface 182 (such as the proximal surface of the cross member) is adapted to be bent, folded, or otherwise reduced in crossing profile to a first configuration in which it can be advanced distally through a relatively small tissue opening, to a second configuration in which it presents a proximal serosal surface contacting area for resisting proximal retraction through the access pathway. Thus, although described primarily in the context of a T-tag and variations thereof, the present invention relates more broadly to tissue anchors of the type for presenting a retention surface which may have any of a wide variety of configurations. Some are described in additional detail below. The stem may also be referred to herein as a tension member, and may comprise a suture, or other single strand or multi-strand element for drawing the tissue anchor against the serosal tissue and/or connecting the tissue anchor to the implantable cuff or other endolumenal implant.

T-tag fasteners are generally configured to flex or pivot at the juncture of the T and tail to allow delivery along the axis of the T through a minimal puncture diameter. T-tag fasteners can be configured with an extended tail that may extend out the mouth and optionally be used to parachute devices for attachment into position in vivo. Other T-tag configurations can include, crimp, snap, screw or other means of securing the T-tag tail when appropriate. One embodiment of a T-tag fastener could include a dual tail. Such a dual tail could be combined with extended tails that could then be tied out side the body with the ensuing knots then tightened within the body. Such a dual tail could be constructed of one of a number of non-biodegradable suture materials known in the art including polypropylene, nylon, braided Dacron or silk. In some clinical situations biodegradable tails could be indicated and could be constructed using materials described herein. In a preferred embodiment the tails could be constructed of a monofilament material.

In certain implementations of the present invention, it may be desirable to increase the effective surface area of the retention surface 182. This may be accomplished using any of a variety of disc or button shaped attachment devices 178 disclosed herein, or by introducing a buttressing component or element in the nature of a washer or other structure for enlarging the effective surface area. This buttressing structure may sometimes be referred to herein as a pledget. The buttressing material is generally configured perpendicular to the axis of the tension element 184 (e.g. suture, rivet or staple) and therefore best distributes forces along the axis of the attachment means.

T-tags or other serosal anchors can be delivered through a hollow needle type delivery system (e.g. T-ANCHOR INTRODUCER GUN (Moss, Moss Tubes)) that has been redesigned/modified so it can be passed through the working channel of an endoscope. A T-tag can be provided with an elongated tail that can extent out through the mouth and be used to parachute structures into place in-vivo.

In one embodiment the T-tags are placed such that the sutures of the T-tags could be knotted outside of the body and the knots could be pushed down the working channel or outside of the working channel of the scope until positioned to retain the cuff. The suture tails could subsequently be removed. To facilitate management of all the suture tails, two T-tags could first be placed to secure the cuff followed by placement of the rest of the T-tags. In a preferred embodiment the T-tag tension elements, such as tails, sutures, or other structures as described herein, would terminate in the stomach, such as by tied knots, sliding buttons, or preexisting terminated ends, such that they would not need to be brought outside of the body.

As an alternative to tying sutures outside of the body, any of a variety of suture locks may be utilized to secure the suture with respect to the cuff. In general, a suture lock is provided with a central aperture for moveably receiving the suture therethrough. The lock may be configured for one way advance along the suture, having a spring biased engaging element for resisting movement of the lock in the opposite direction. Alternatively, a central plug may be advanced into the central lumen, to compress the suture within the suture lock and retain the suture lock at a selected position. Any of a variety of clips may also be axially or radially moved into position, to engage the lock with the suture. The suture lock may be advanced down the suture and positioned with the desired tension against the interior surface of the cuff, and activated as necessary to lock the suture lock in place. The remaining suture tail may be severed, using conventional endoscopic techniques.

Alternatively, the suture lock may be secured to the cuff 102 such as at each aperture 122, prior to implantation of the cuff 102 in the patient.

Many of the serosal anchors described herein can be formed using a single piece of Polypropylene, Nylon, PEEK, silicone, or other polymeric material well known in the art for use in construction sutures, which forms the "T" and tail as a single unit. Alternately two different materials can be combined, for example by insert molding, to achieve different properties of the "T" and tail. In another embodiment this could be combined with a "T" portion that is coated with a material selected for specific clinical properties such as encouraging or discouraging either in-growth or adhesion. The "T" portion may also be surrounded by another material such as ePTFE or Dacron graft material. "T" diameter or serosal surface contacting width can vary for example ranging from 0.5 mm to 3.0 mm in diameter for nylon or polypropylene with the typical "T" having a diameter of 1-2 mm. A tail could be the dimension of a standard suture and could generally vary from 5-0 to 0 (USP standard classification) though smaller or larger sizes may be appropriate in certain clinical situations.

FIGS. 7A & 7B illustrate a curved T-member 300 for a T-tag fastener. The convex curved tissue-contacting surface 302 of the curved T-member 300 serves to distribute the attachment force for an implanted device smoothly across the tissue to minimize any stress concentrations or higher pressure spots that could cause tissue necrosis and/or erosion. The T member 300 has a double eyelet 304 for attachment of a suture or other filament. The T-member is preferably molded of a fairly rigid, high strength biocompatible polymer such as PEEK.

FIGS. 23A-23B of application Ser. No. 11/124,634, previously incorporated by reference, illustrate a T-tag fastener 2200 with a hydrogel disc 2204 that can be placed between the deployed T-member 2208 and the extragastric (serosal) surface. The disc 2204 could be delivered through the T-tag delivery needle, and unroll after passage through the needle. The hydrogel disc 2204 acts as a buttress or pledget to distribute the forces transmitted between the T-member 2208 and the extragastric surface and thereby it strengthens the attachment of the T-tag fastener 2200. The hydrogel used in FIGS. 23A-23B can optionally be replaced with alternate materials described herein for example silicone, NiTi and fluoropolymers. A Hydrogel or other buttress or Teflon pledget for a T-tag could also deploy in some other manner. The disc configuration shown can be replaced with for example, braided or woven wires or filaments that would expand/deploy after passage through the needle (FIGS. 24A-24B), a Malecot-style deployable tubular structure (FIGS. 25A-25B) or other expandable or deployable configuration (e.g. FIGS. 26A-26B). Although FIGS. 23A-23B, 24A-24B, 25A-25B, and 26A-26B illustrate T-tag fasteners, such as 2200 in FIGS. 23A-23B used with T-members 2208, uses of the T-tag fasteners without T-members and just with the hydrogel disc 2204 of FIGS. 23A-23B or the woven filaments, Malecot-style tubular structure, or the expandable structure of FIGS. 24A-24B, 25A-25B, and 26A-26B, respectively, are also contemplated.

In the above examples where it has been suggested that a fixed distance between the T-member and the device it is being used to attach is desirable it has been suggested that in some cases a distance greater than the thickness of the captured gastric wall may be clinically indicated. This is due to the ability/tendency/possibility that the gastric wall could react to the presence of a foreign body (the attachment structures) by thickening. In this event, in some cases, it can be clinically preferable that the preset distance accommodate some or all of this increase in wall thickness.

Attaching Sleeve to Cuff

The cuff 102 and sleeve 100 may be formed as an integral unit, or supplied to the clinical site as a single unit, for installation as one piece. Alternatively, the cuff 102 and sleeve 100 are provided as separate components, with an instruction that the cuff is inserted first as described elsewhere herein, followed by insertion of the sleeve 100 and attachment of the sleeve 100 to the cuff 102. Alternatively, the sleeve 100 could be deployed first in the intestines then the cuff 102 can be inserted into position. Following attachment of the cuff, the sleeve 100 could then be attached to the cuff 102. The sleeve 100 may be attached to the cuff 102 in any of a variety of ways, depending upon the ease with which removal may be desired. For example, stitching or clipping may be accomplished, as described previously. Alternatively, any of a variety of snap fit, interference fit, hooks, loops or other techniques may be utilized.

Referring to FIG. 13, there is illustrated a perspective fragmentary view of a device as seen in FIG. 1. In this implementation, a plurality of connectors 128 are provided, for connecting the sleeve 100 to the cuff 102. Connectors 128 are preferably configured for deployment through an endoscope, and may be conventional sutures, or hooks or clips which may be manipulated endoscopically.

FIGS. 14 and 15 show two steps in an installation sequence. In FIG. 14, a cuff 102 has been previously attached at a treatment site within the body, such as in the vicinity of the GEJ 106. The distal end (not shown) of a sleeve 100 has been advanced through the central lumen of the cuff 102, and manipulated down the intestine as disclosed elsewhere herein. The proximal end of the sleeve 102 is provided with an annular radially outwardly extending stop surface as described below. As seen in FIG. 15, the sleeve 100 may be advanced distally until the stop surface on the sleeve engages a corresponding stop surface supported by the cuff 102.

In general, a first retention surface such as an upwardly facing surface 320 on a radially inwardly facing flange 322 or plurality of tabs on the attachment device (cuff) 102 limits distal movement of the sleeve 100 by contacting a second retention surface on the sleeve. The second retention surface may be a downwardly (distally) facing surface 324 such as the distal surface of a radially outwardly facing or inclined annular flange 326 or plurality of tabs on the proximal end of the sleeve 100. In this configuration, the sleeve may be passed through the cuff and simply "dropped" into place and the first and second retention surfaces limit further distal travel of the sleeve relative to the cuff.

Peristalsis and normal gastrointestinal tract activity will place tension or other forces on the sleeve 100. Thus, the connection between the sleeve 100 and the cuff 102 should be sufficient to resist detachment under normal use conditions. For this purpose, the proximal end of the sleeve 100 may be provided with one or more reinforcing structures such as an annular ring 328. A corresponding annular ring or band (not illustrated) may be provided on the radially inwardly facing flange 322. If the outside diameter of the ring 328 exceeds the inside diameter of the ring or other reinforcing structure carried by flange 322, the sleeve cannot be pulled from the cuff 102 unless the force applied is sufficient to deform one or both of the complementary rings. The structural integrity of this type of interfit structure may be optimized, taking into account the likely tension forces applied by the GI system, in view of the desired flexibility and compressibility of the implant as has been discussed.

In other variations of these embodiments, the tubular wall of the cuff can taper inward in the distal direction for attaching a sleeve with a smaller diameter than the cuff or the wall of the cuff can taper outward in the distal direction for attaching a sleeve with a larger diameter than the cuff.

Each of these embodiments permits the sleeve to be dropped into place or snap fit into place by elastic or other deformation of the interlocking retention surfaces. The attachment can be made more secure by the addition of one or two or more staples, stitches of suture adhesives or t-tags. Removal can be accomplished using a removal tool with a stop surface for placing against a surface on the cuff to prevent proximal movement of the cuff, and a grasper for grasping the proximal end of the sleeve and pulling the sleeve to release it from the cuff without straining the connection between the cuff and the tissue. Any additional sutures can be snipped using conventional endoscopic cutting tools. The cuff may also be removed if desired, or a different sleeve may be introduced and secured to the cuff.

In preferred embodiments, cuff 102 is first deployed near the GEJ 106 and then sleeve 100 is attached in situ to cuff 102 with permanent coupling if no intervention is required or with a releasable connection if intervention is possible, without needing to target a specific attachment point or series of attachment points, and without incurring leaks. For example, sleeve 100 can be attached to cuff 102 using an interference fit as shown in FIGS. 50A-50C where the lip 820 of sleeve 100 is larger in diameter than the colllapsed distal portion 824 of the cuff 102. In this design, the lower portion of the cuff has a variable configuration. As shown in FIG. 50A, the lower portion of the cuff has triangular shaped voids 832 in the cylindrical surface area. This is to facilitate forming a tapered cone out of the lower portion of the cuff when the distal end is drawn together as shown in FIG. 50B. While two voids are shown there could be one or three or more voids as desired. There can be a cord that is tensioned to draw the distal end of the cuff together like a drawstring or a hoop in the distal end that has different diameters depending on temperature or delivered energy or mechanical tensioning.

The benefit of this configuration is that after the cuff is anchored to the GEJ, the distal end of the cuff can have the same size or a larger opening than the proximal end of the cuff. This allows the maximum working channel to place the bypass sleeve in the intestines after cuff placement, then retract the sleeve up into the cuff for attachment. Once the proximal end of the bypass sleeve is retracted into the lumen of the cuff the distal end of the cuff can be cinched down to form the taper to hold the sleeve in place. Sleeve lip 820 can taper from a larger diameter to a smaller diameter distally so as to wedge sleeve 100 in cuff 102 and thus maintain proper alignment. In some embodiments, cuff 102 also comprises a taper matching the taper of sleeve 100. In one example, the Morse taper such as used on lathe chucks, can be used.

In one embodiment, as illustrated in FIGS. 50A-50B, cuff 102 comprises locking voids 828 around the circumference of distal portion 824. One or more wedge-shaped portion(s) of material 832 are removed from distal portion 824, as shown in FIG. 50A. Removal of wedge-shaped portion(s) 832 allows distal portion 824 of cuff 102 to be collapsed to form a taper, as shown in FIG. 50B. Sleeve 100, shown in FIG. 50C, comprises a lip 820 comprising tabs 836. The inner diameter of lip 820 can be smaller than the outer diameter of distal portion 824 to create the interference fit. Sleeve 100 and cuff 102 are attached by fitting tabs 836 into voids 828.

In some embodiments, the inflow sleeve ring can comprise a ring with an outer diameter larger than the inner diameter of cuff 102. The sleeve ring has sufficient radial rigidity to withstand collapse when deployed within cuff 102. Cuff 102 has sufficient radial rigidity to accommodate the sleeve ring without deforming, for example, into an elongated oral orifice. The inflow sleeve ring can also comprise an outward and downward facing radial flange that can fit over the lip of the proximal end of cuff 102 or to a flange formed of some material on the distal end and inner diameter of cuff 102 such as a silicone ring.

Sleeve 100 can also be affixed to cuff 102 using suture, welding, loops and hooks, snap fit attachments, clips, Ziploc gaskets, Velcro, and adhesives, as well as any other means as would be contemplated by those skilled in the art.

In preferred embodiments, the attachment between sleeve 100 and cuff 102 cannot be detached unintentionally, prevents leakage by effectively providing a seal between sleeve 100 and cuff 102, and is compliant so as to fully collapse and expand under the natural motion of the stomach and the GEJ 106. Because it may be difficult to optimize attachment and sealing functions using one attachment mechanism, aspects of the present invention disclose attachment and sealing mechanisms decoupled from one another. In one example, a button and loop or hanger-style attachment mechanism with discrete attachment points may be used to attach cuff 102 and sleeve 100 together, while, further downstream, a continuous, flexible flange-style mechanism provides the sealing function.

In embodiments in which sutures or guide rods are used to place sleeve 100 on cuff 102, multiple thin flexible rods or sutures from cuff 102 can be attached to cuff 102 so that they track up and out of the patient. The rods or sutures trail cuff 102 as it is placed and act as guide rails when sleeve 100 is placed so that sleeve 100 can be aligned with cuff 102 and engage attachment points between sleeve 100 and cuff 102. The attachment points can include any of the means for affixing described above including clips, snap fit attachments, and other means. The sutures and guide rods can comprise barbs or press fit bulges that barely fit through grommets on sleeve 100 such that when sleeve 100 is placed the sleeve ring snaps over the guide suture fixation point and then the guide suture or rod can be severed above the fixation point.

In some embodiments cuff 102 is attached to sleeve 100 outside of the patient's body during the procedure or as a pre-assembled system. Sutures, adhesives, welding, and any other means as described above and as would be contemplated by those skilled in the art can be used to attach sleeve 100 to cuff 102. Sleeve 100 can be detachable from cuff 102 post implantation. For example, a perforation can surround sleeve 100 where sleeve can be torn away from cuff 102. In another example, a rip-suture can be pulled or cut to detach cuff 102 from sleeve 100. The rip-suture can be the same suture primarily attaching sleeve 100 to cuff 102 or it can be a separate suture with no function other than serving as a mechanism to release cuff 102 from sleeve 100.

The gastrointestinal sleeve device 100 preferably has a length such that ingested food and liquids bypass most or all of the stomach and at least a portion of the small intestine. Undigested food and liquids exit the distal end 112 of the sleeve 100 into the small intestine 114 reducing caloric absorption and eliciting physiological responses within the intestines. See FIG. 1. The gastrointestinal sleeve 100 can have a constant diameter throughout its length or the diameter may vary along the length.

For example, the proximal end of the sleeve 100 may be provided with a diameter that corresponds with the diameter of the cuff 102. This may be in the vicinity of about 25 mm to about 35 mm. The sleeve may be provided with the same diameter throughout its entire length, although this would result in folding of the sleeve longitudinally as it passes through the intestine. For example, the duodenum may have an inside diameter on the order of about 15 mm. As a consequence, one implementation of the invention provides a sleeve having a proximal end having a first cross sectional area, adjacent a tapered or stepped zone across which the cross sectional area reduces to a second, smaller cross sectional area. The axial length of the transition zone may be less than about 2 cm, and some embodiments less than about 5 cm, and in some embodiments no greater than about 10 cm. Alternatively, the length of the transition zone may exceed 10 cm or 20 cm, where wrinkling or longitudinal folding of the sleeve is not sought to be avoided.

The sleeve 100 and cuff 102 may be configured to provide a restrictive opening, either within the sleeve 100 or the cuff 102. The restrictive opening may be effectively provided at the distal end of the transition zone 101 illustrated in FIG. 13. The stoma may be positioned to provide a volume proximally of the stoma of no greater than about 100 cc, and in some implementations of the invention no greater than about 50 cc, and in certain applications no greater than about 30 cc, depending upon the desired clinical result.

As has been discussed in the parent applications previously incorporated herein by reference, additional structures and features may be included on the sleeve 100. For example, one or more structures may be provided on the distal end of the sleeve 100 for facilitating transport of the sleeve 100 through the intestinal system. This may include a balloon or other bulking structure to facilitate preferential operation of peristalsis on the distal end of the sleeve. Any such structures may be absorbable, detachable, or permanent, depending upon the desired clinical performance. Alternatively, any of a variety of grasping structures such as a grasping tab or ring may be provided to facilitate grasping the distal end of the sleeve 100 using an installation tool, which is advanced distally through the intestinal system.

The gastrointestinal sleeve 100 can be impermeable along the entire length or some or all of the device may be porous or semipermeable. Preferably, the wall of the gastrointestinal sleeve 100 is thin and flexible so that peristalsis is coupled to the internal lumen of the sleeve 100. A gastric sleeve that extends beyond the pylorus 116, with or without an intestinal sleeve component, can allow use of the pylorus as a natural stoma by configuring the sleeve to close by normal operation of the pylorus 116 and then open to allow passage of food when the muscles of the pylorus relax. The section of the sleeve device 100 that passes through the pylorus 116 will preferably have enough wall flexibility or compliance to allow normal opening and closing of the pylorus to release and retain stomach contents and to allow drainage of stomach secretions around the outside of the sleeve. This can optionally be accomplished by the inclusion of pleats, channels or other structures to facilitate the collapse and sealing of the sleeve as well as passage of gastric secretions along the outside of the sleeve as shown schematically in FIG. 6A.

Dimensions, materials and other specifications described in U.S. patent application Ser. No. 11/124,634 can be selected and adjusted based upon the clinical situation. For example, the gastrointestinal sleeve 100 is preferably approximately 60-180 cm in length whereby partially digested or undigested nutrients exit from the sleeve into the jejunum where they can elicit a hormonal, neural and/or osmotic reaction in the jejunum, ileum and/or duodenum. Increasing the length of the sleeve can reduce the absorption of nutrients in a manner similar to that of a Roux-en-Y or bypass device, as will be understood by those skilled in the art. The sleeve may extend sufficiently far into the intestine, such as past the ligament of Treitz, so that it is retained in the intestine and not pushed back into the stomach. Lengths of at least about 50 cm, at least about 75 cm, at least about 100 cm and at least about 120 cm are contemplated, although different lengths may be appropriate depending upon the requirements of a particular patient. Lengths of no greater than about 5 cm or no greater than about 10 cm or no greater than about 20 cm may be desirable for certain patients, depending upon the desired clinical outcome.

The releasable attachment of the sleeve to the cuff as disclosed herein facilitates removal and replacement of the sleeve 100. Thus, the response of a particular patient to a first sleeve having a first length can be observed. If more or less intestinal absorption is desired, the first sleeve can be endoscopically removed from the cuff, and replaced by a second sleeve having a second shorter or longer length. Therapy is thus adjustable, which may be desirable if either the initial sleeve length was suboptimal or if it becomes suboptional due to post implantation changes such as stomach remodeling or behavioral changes.

Optionally, the sleeve can include coatings on its interior and/or exterior to enhance the surface properties of the sleeve in clinically relevant manners. Coating examples include: 1) parylene coatings to increase the chemical resistance of a sleeve material, 2) coating with an antimicrobial agent to resist infection and/or 3) coating with an anti-inflammatory agent to reduce tissue inflammatory response, as described herein. Similarly, the interior and exterior of the sleeve can optionally be coated with a low friction material (e.g. a hydrogel) to reduce friction of food passage (interior) and reduce gastric irritation (exterior). One example of such a low friction material is a lubricious coating such as the photolink lubricious coating manufactured by Surmodics Inc. and disclosed on pg. 5, paragraph 58, in U.S. utility patent publication 2005-0049718, the disclosure of which is herein incorporated in its entirety by reference.

U.S. patent application Ser. No. 10/698,148 describes the use of biodegradable or bioresorbable materials for construction of a gastrointestinal sleeve device to obviate the need for removal of the sleeve device at the end of the treatment period. The entire gastrointestinal sleeve device or a portion of it may be made of biodegradable material. The gastrointestinal sleeve device may be made of biodegradable materials with different rates of degradation or resorbtion. The gastrointestinal sleeve device may be configured with a series of segments that biodegrade sequentially. For example, a first portion on the distal end of the sleeve may degrade first, followed some time later by a second intermediate portion and a third proximal portion. Next the attachment between the sleeve 100 and cuff 102 would degrade and, finally, the T-tags or other fasteners would degrade. Alternatively, the gastrointestinal sleeve device may be configured with a series of short segments of non-biodegradable material that are attached to one another with biodegradable material. The biodegradable attachment portions may be made of biodegradable materials with different rates of degradation or resorbtion so that they biodegrade sequentially. In either case, the biodegradable material would allow a gradual change of therapy over time, without having to revise or replace the implant. The patient could get used to the gradual change in therapy more readily than a sudden change and may be better able to avoid a rebound in weight gain. It may also allow for a safe mode of degradation and elimination. The device would degrade into pieces small enough that they could be eliminated without any danger of bowel obstruction.

Alternatively, selected portions of the gastrointestinal sleeve device may be made of biodegradable material. For example, openings in the sleeve can be covered with biodegradable material that will gradually degrade over time, eventually allowing food to mix with digestive secretions. The biodegradable material would allow a gradual change of therapy over time, without having to revise or replace the implant. The gastrointestinal sleeve device with the openings in it could be left in place for long-term maintenance of weight loss or it could eventually be removed.

In some embodiments the rate of degradation of the biodegradable material forming the sleeve could be coordinated with the natural pH of the anatomical environment and/or to properties of the material forming the sleeve, to achieve a predetermined sequential degradation of the implant. In accordance with one degradation sequence, a distal (intestinal) portion of the sleeve dissolves before the proximal (gastric) portion. For example, the sleeve could be constructed of a material that degrades at a faster rate in a relatively basic environment than in a relatively acidic environment such that the distal portion of the sleeve in the intestine would dissolve before the proximal portion of the sleeve in the stomach. The pH of the sleeve environment could also be altered by an external source, for example by ingestion of a substance that would change the pH of the stomach and/or intestine and thus hasten degradation of the gastric component. Alternatively, the distal and proximal portions of the sleeve could be constructed of two different materials with the material comprising the distal portion dissolving faster than the material comprising the proximal portion. Alternatively, the material forming the sleeve could be thinner at the distal portion than at the proximal portion such that the distal portion would dissolve in less time than the proximal portion. All or any combination of the above alternatives could be used to set the time frames of degradation of the distal and/or proximal portions of the sleeve depending on the desired performance.

Biodegradable material suitable for construction of a gastrointestinal sleeve device is sold under the name Plastifilm by OsteoBiologics, Inc., located in San Antonio, Tex. This biodegradable polymeric film material is described in U.S. Pat. No. 6,514,286, which is hereby incorporated by reference. Additional information from the supplier about this material is available at: http://www.obi.com/.

Sleeve Delivery

Another aspect of the present invention involves devices and methods for delivery and deployment of a gastrointestinal sleeve device into a patient's gastrointestinal tract. One method to facilitate delivery of the device into and through the patient's small intestine is to place a guidewire and/or catheter into the intestine to the depth desired and then push the gastrointestinal sleeve device over the guidewire. Successful techniques for placing a guidewire into the small intestines have been described by G. Long, T. Mills and C. P. Swain in an article entitled *Techniques for advancing guide wires and devices in the lumen of the gastrointestinal tract*. Another technique that could be adapted for placing a device such as a gastrointestinal sleeve device into the small intestine was described by H. Yamamoto and K. Sugano in an article entitled *A new method of enteroscopy—the double-balloon method*, Can J. Gastroenterol. 2003 April; 17(4):273-4. These techniques can be used in combination with many of the delivery and deployment methods described herein and in the prior application.

In one embodiment, sleeve 100 is delivered using a Leonard tube device or similar pushable device. The pushable device comprises a flexible pushable shaft that can bend as needed to advance sleeve 100. The distal end of the pushable device comprises a pulling device that facilitates the natural peristaltic action of the GI tract in pulling the pushable device down the intestine. The pulling device can have or assume an enlarged configuration and can be shrunk before removal of the pushable device. In its enlarged configuration, the pulling device provides greater surface area of contact between the device and the intestinal walls during deployment thus minimizing the risk of perforation of the walls and improving the pushable device's ability to navigate a tortuous path. In some embodiments, the pushing device comprises an aspiration lumen that enables aspiration of air or fluids out of the GI tract distal to the end of the pulling device to aid in advancing the device. In some embodiments, the pulling device is part of the pusher rod described below. The pulling device is used only for deploying sleeve 100 and after deployment it is, for example, deflated or designed to shrink by osmosis or other means, released from sleeve 100 or the pusher rod and allowed to pass through the remainder of the GI tract or completely dissolved. Some embodiments of the pulling device include a saline filled balloon, a silicone ball, osmotic balloons, an absorbable tether and ball, an absorbable ball, a sleeve plug that is dissolvable when the patient drinks fluids, and a conical sleeve distal end. The conical sleeve distal end embodiment is formed by choking down the inner diameter of a small portion at the distal end of sleeve 100 such that when filled with food or fluid sleeve 100 experiences a predetermined amount of resistive force to flow which tensions sleeve 100 in place. This embodiment is configured so as not to risk any obstruction and can comprise elastic properties at the distal end so that when an excess of resistive force is experienced, the inner diameter will expand to discharge any back flow.

In some embodiments, sleeve 100 can be held at or near its distal end e.g., with a pusher rod and advanced using a combination of force applied by a pusher rod and the natural peristaltic action of the GI tract. The pusher rod can be placed through the lumen of sleeve 100 or along the outside surface of sleeve 100 and held to sleeve 100 using a variety of devices as would be understood by those skilled in the art, including a snare type device, a jaw type device, or any other known capture device or method.

The pushable device used to advance sleeve 100 can have one or more lumens to provide a fluid flush as the device is removed to reduce any friction that might cause sleeve 100 to get pulled out with the device. These lumens can, for example, provide a fluid flush along the length of the device in a sprinkler hose type method.

In a preferred embodiment, the gastrointestinal bypass sleeve may also be deployed within the intestine using a toposcopic, or everting technique, based upon the method of internal pressurization that is well known in the everting catheter art. Pressurization may be accomplished by placing the proximal end of the axially collapsed sleeve in communication with a source of inflation or everting media, such as a liquid or gas. Liquid such as water or saline may be preferred, and may additionally be provided with a radiopaque additive to permit real time fluoroscopic visualization of the progress of the deployment within the GI system. Additional additives may also be provided, such as antibiotics, nutritional supplements or others as may be desired.

Figure 8A:
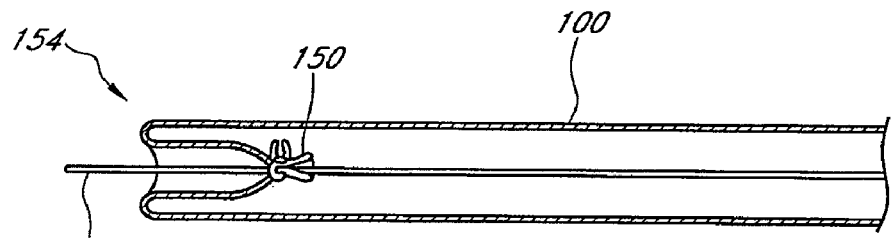
FIG. 8A is a side elevational cross section through a partially inverted sleeve.
Figure 8B:
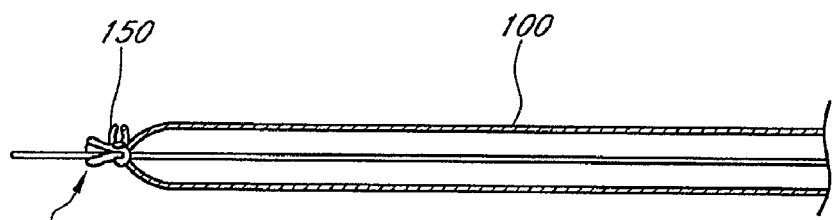
FIG. 8B is a side elevational cross section through a sleeve, showing an absorbable distal closure.

To maintain the internal fluid pressure used to assist in everting the inverted gastrointestinal sleeve, the distal end of the sleeve may be temporarily occluded or sealed during deployment. FIGS. 8A-8B illustrate one of a number of options for sealing the distal end 112 of a gastrointestinal sleeve 100 during delivery and deployment. FIG. 8A shows the inverted distal end 112 of the gastrointestinal sleeve 100 sealed with a suture or tie 150 which may be degradable and formulated to dissolve within approximately 2 or 6 or 24 hours following deployment in the intestines. Dissolution of the biodegradable tie 150 can be aided by introduction of a solvent, or active agent, or inducing a pH change that is ingested or placed in the everting fluid. The distal end 112 may also be releasably secured to a pull line 152 such as a suture or wire, to assist in inverting the sleeve as will be apparent to those of skill in the art. Alternatively, the suture or wire could be delivered by the sleeve and act as a guide wire for the placement of any of a number of other devices in the GI tract. FIG. 8B shows the noninverted distal end 112 of the gastrointestinal sleeve 100 sealed with a biodegradable tie 150 that may be formulated to dissolve within the intestines, prior to proximal retraction of the pull line 152.

The distal end may alternatively be temporarily occluded using adhesives, such as a water soluble adhesive or pressure sensitive adhesive applied to the interior surface of the distal end 112 of the sleeve. Alternatively, the distal end of the sleeve may be collapsed and folded over onto itself with or without the use of adhesives. Solvent bonding, thermal spot welding or other bonding technique may be used to close the distal end 112, in a manner that a slight increase in pressure can be applied to the inflation media following full deployment, to rupture the seal. A tie line may alternatively extend proximally from the distal end 112, either inside of the lumen or outside of the sleeve 100. Proximal retraction of the tie line following sleeve placement will untie a knot or otherwise release the distal end 112. Otherwise the distal end may be simply left open during the deployment process.

Figure 9A:
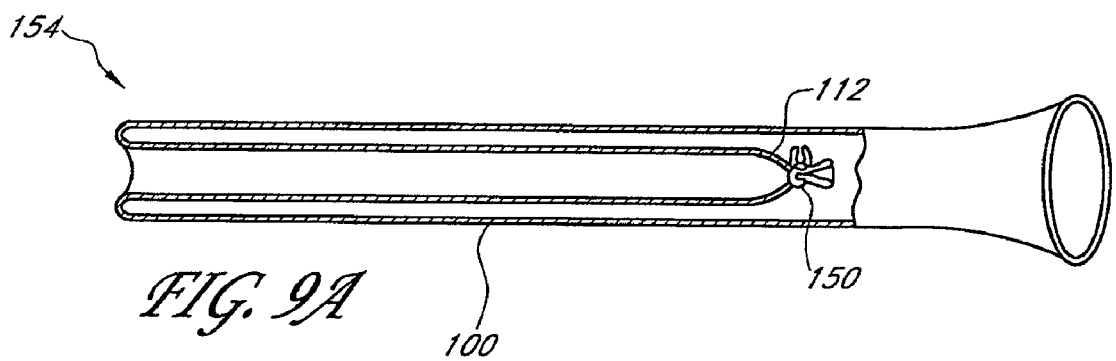
FIG. 9A is a partial cross sectional view of a sleeve having a single invertion.
Figure 9B:
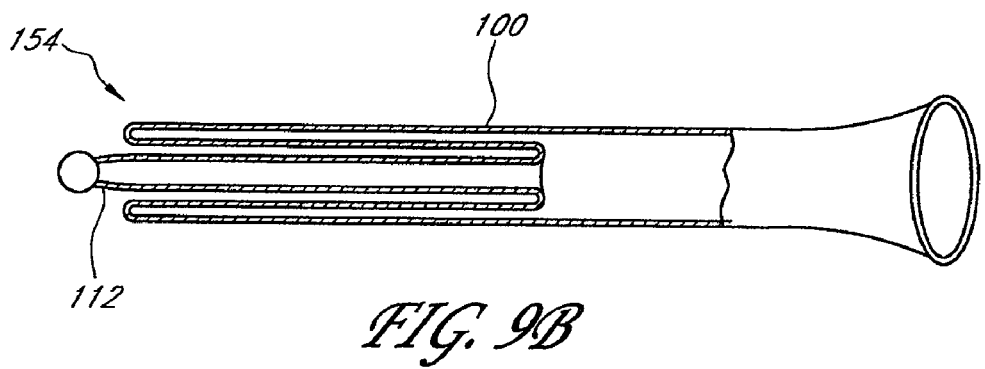
FIG. 9B is a partial cross sectional view of a sleeve having a double invertion.

FIG. 9A shows a gastrointestinal sleeve 100 loaded in an inverted configuration. FIG. 9B shows a gastrointestinal sleeve 100 loaded in a double-inverted configuration. A full single inversion will reduce the length of the sleeve 100 by about 50%, while a full double inversion will reduce the length of the sleeve 100 to about 33% of its original length. The sleeve can be inverted up to 100% with a single inversion by pulling the distal end 112 proximally of the proximal end of the sleeve, if there is a means to control the distal end 112 of the sleeve as it will be extending out of the proximal end. Deployment of the sleeve will thus still require a first step of positioning the distal end 154 of the inverted sleeve 100 at a first position within the GI tract, and then second everting the sleeve to position the everted distal end at a second position within the GI tract, downstream from the first position. The second position will normally be at least about 50 cm and often at least about 75 cm or 100 cm or more distally of the Pyloris. The first position where the distal end 154 of the inverted sleeve is placed may be at about the Pyloris, within about 20 cm of the Pyloris, or within about 50 cm of the pyloris, depending upon the device design and desired deployment procedure.

Inverting the sleeve simplifies the delivery and deployment of the device, but it adds some additional constraints to the configuration of the device. The inverting segments can have very thin walls and inverting interfaces can be highly lubricious for easy and reliable deployment. For example blow molded 90A durometer polyurethane of a wall thickness on the order of 0.005" or less, most preferably about 0.002", with a lubricious coating will work in this manner. Eversion within the intestine may be accompanied by introduction of an irrigating or lubricating fluid on the outside of the sleeve 100, and/or provision of a lubricant in between contacting surfaces of the inverted sleeve. Additional details are disclosed in copending application Ser. No. 10/698,148, filed Oct. 31, 2003, entitled Apparatus and Methods for Treatment of Morbid Obesity, the disclosure of which is incorporated in its entirety herein by reference.

Toposcopic Delivery

Figure 16A:
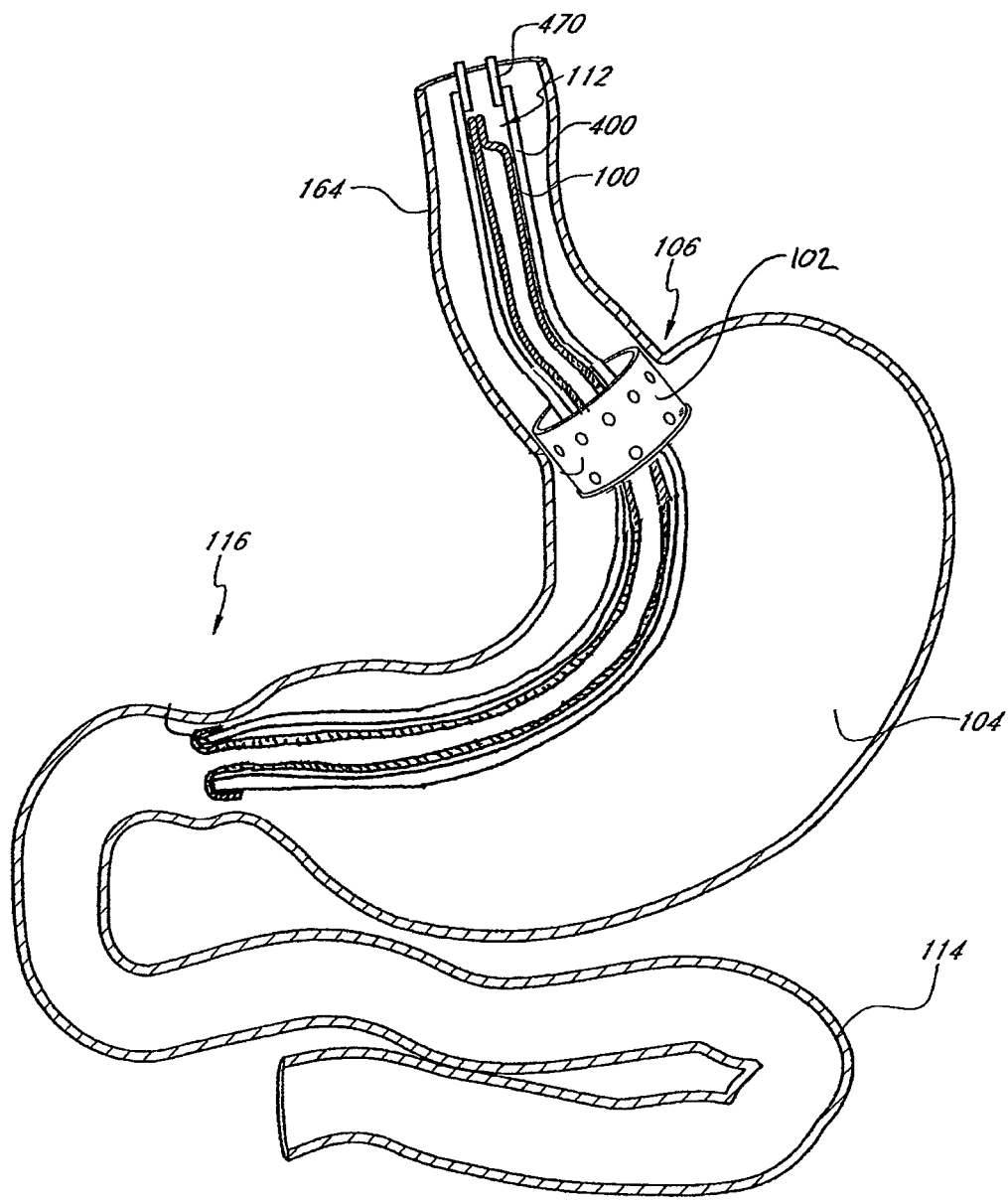
FIG. 16A is a schematic illustration of a bypass sleeve configured for toposcopic delivery.
Figure 16B:
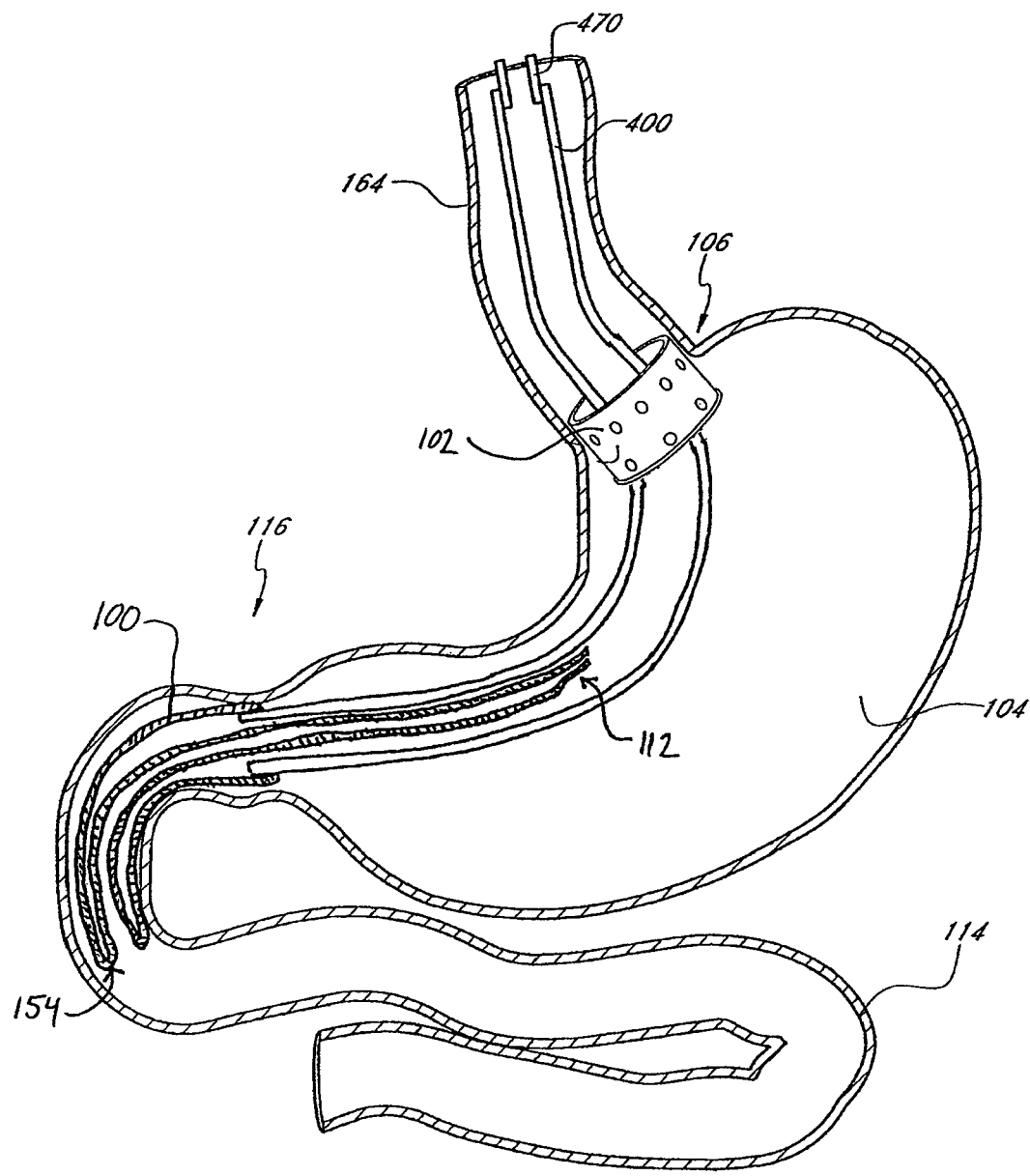
FIG. 16B is a schematic illustration as in FIG. 16A, with the bypass sleeve partially toposcopically deployed.
Figure 16C:
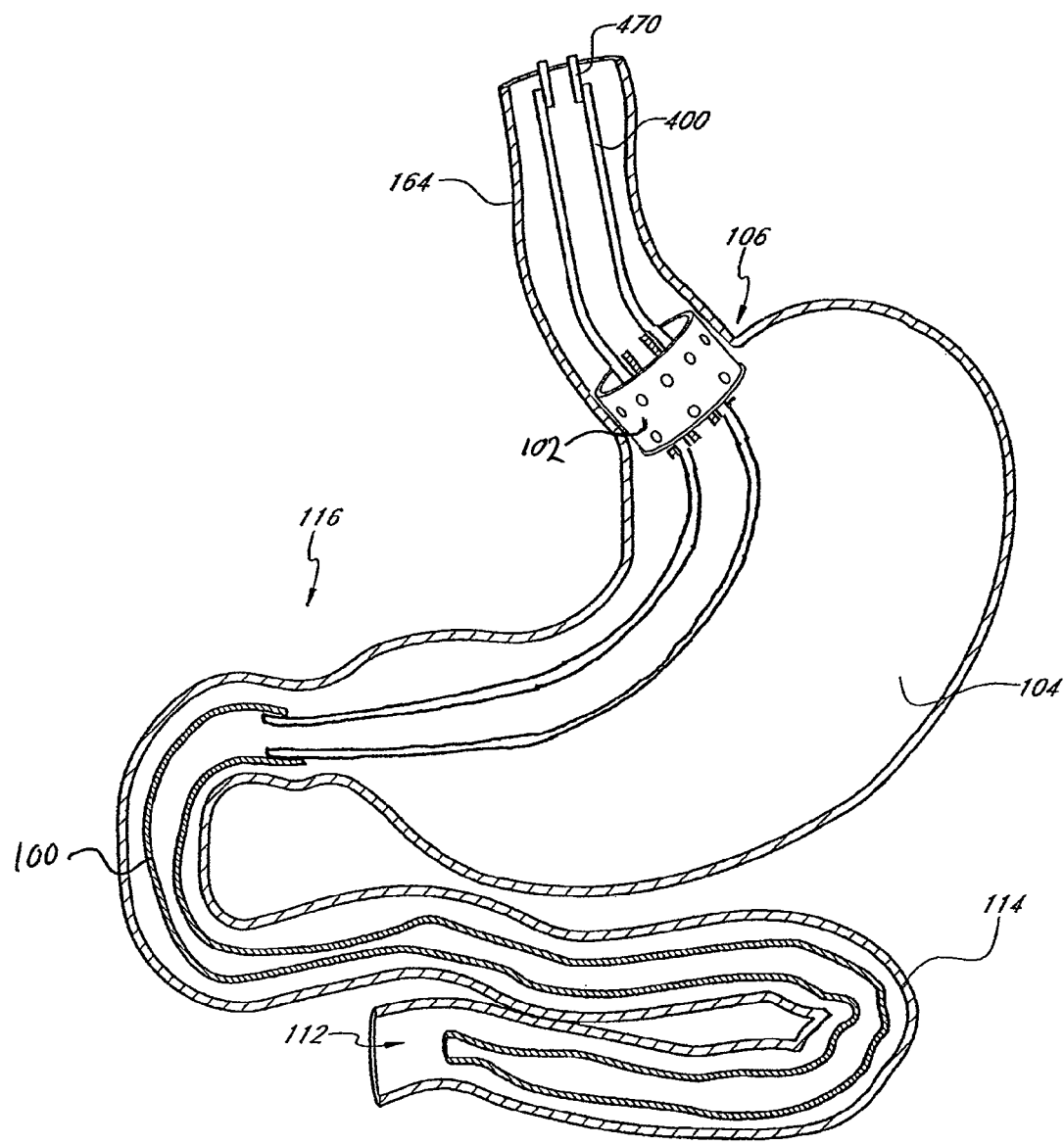
FIG. 16C is a schematic illustration as in FIG. 16B, with the bypass sleeve fully toposcopically deployed.

In some embodiments of the present invention, as shown in FIGS. 16A-16C, toposcopic delivery of sleeve 100 is achieved by performing the following steps:

Attach cuff 102, as discussed above. For simplicity, the attachment anchors for attaching cuff 102 to tissue in the vicinity of GEJ 106 are not shown.

Figure 17:
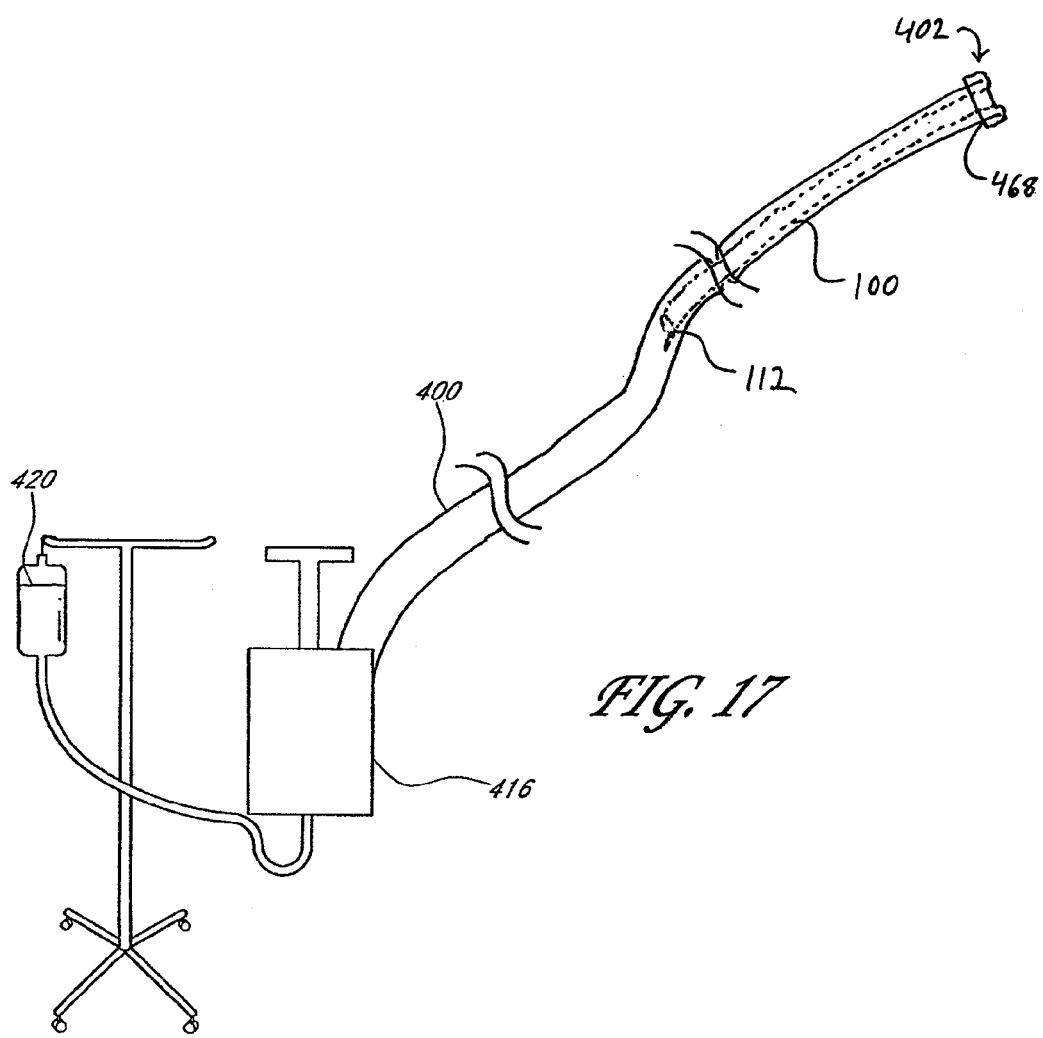
FIG. 17 is a schematic illustration of a system for pressurizing a toposcopically deliverable sleeve.

Place a filling catheter 400 in fluid communication with a flushing device 416 (FIG. 17).

Attach sleeve 100 to filling catheter 400, invert sleeve 100 within the filling catheter, and create a fluid-tight seal 468 between the sleeve 100 and filling catheter 400, if these steps have not been previously done.

Use a sleeve grasper or advance filling catheter 400 to position distal sleeve end 154 of the undeployed sleeve 100 at or into the pylorus 116.

Flush filling catheter 400 with fluid to deploy sleeve 100 into intestine 114.

Confirm full placement using back pressure measurements or fluoroscopy or x-ray to detect radiopaque markers (not shown) on sleeve 100.

Attach cuff 102 to sleeve 100.

FIG. 16A shows cuff 102 deployed in the vicinity of GEJ 106 and the proximal end of sleeve 100 and the distal end of filling catheter 400 deployed in stomach 104 with distal end 112 of sleeve 100 retracted proximally within the filling catheter 400 at least as far as the esophagus 164. FIG. 16B shows sleeve 100 partially unraveled or otherwise deployed such that distal end 112 has advanced past GEJ 106. FIG. 16C shows sleeve 100 fully deployed down intestine 114.

Sleeve 100 can be inverted one or more times to create multiple layers of sleeve that unravel during toposcopic delivery. FIG. 9B shows a sleeve 100 with two inversions. In preferred embodiments, sleeve 100 is inverted once.

As shown in FIG. 17, filling catheter 400 is placed in fluid communication with a device 416 that flushes filling catheter 400 with inflation media such as a fluid. Device 416 can comprise, for example, an electronic or hand-actuated piston or plunger, hand pump, impeller pump, or peristaltic pump. In some embodiments, an endoscope can flush filling catheter 400 with fluid. Device 416 can in turn be placed in fluid communication with a fluid source 420. For example, device 416 can be in fluid communication with a container 420 that holds fluid. Container 420 can hold volumes of fluid ranging from 0.25 liters to 15 liters. In preferred embodiments, container 420 holds between one and five liters. Device 420 can flush fluid through filling catheter 400 at a rate ranging from 5 cc to 100 cc per stroke or actuation of device 420. In preferred embodiments, device 420 flushes fluid through filling catheter 400 at a rate of 30 cc to 300 cc per stroke. Optionally, the filling catheter 400 or the device 416 can have a pressure or volume measurement device to measure the pressure or delivered volume of fluid that is used to evert the sleeve 100. This can be used as an alternative way to determine when the sleeve is fully deployed. The volume measurement can be used to determine when enough fluid has been delivered to fully deploy the sleeve 100. The pressure measurement can be used to detect the pressure drop once the sleeve is fully deployed and the distal end 112 of the sleeve opens up to allow the fluid to pass through with less back pressure.

Figure 18:
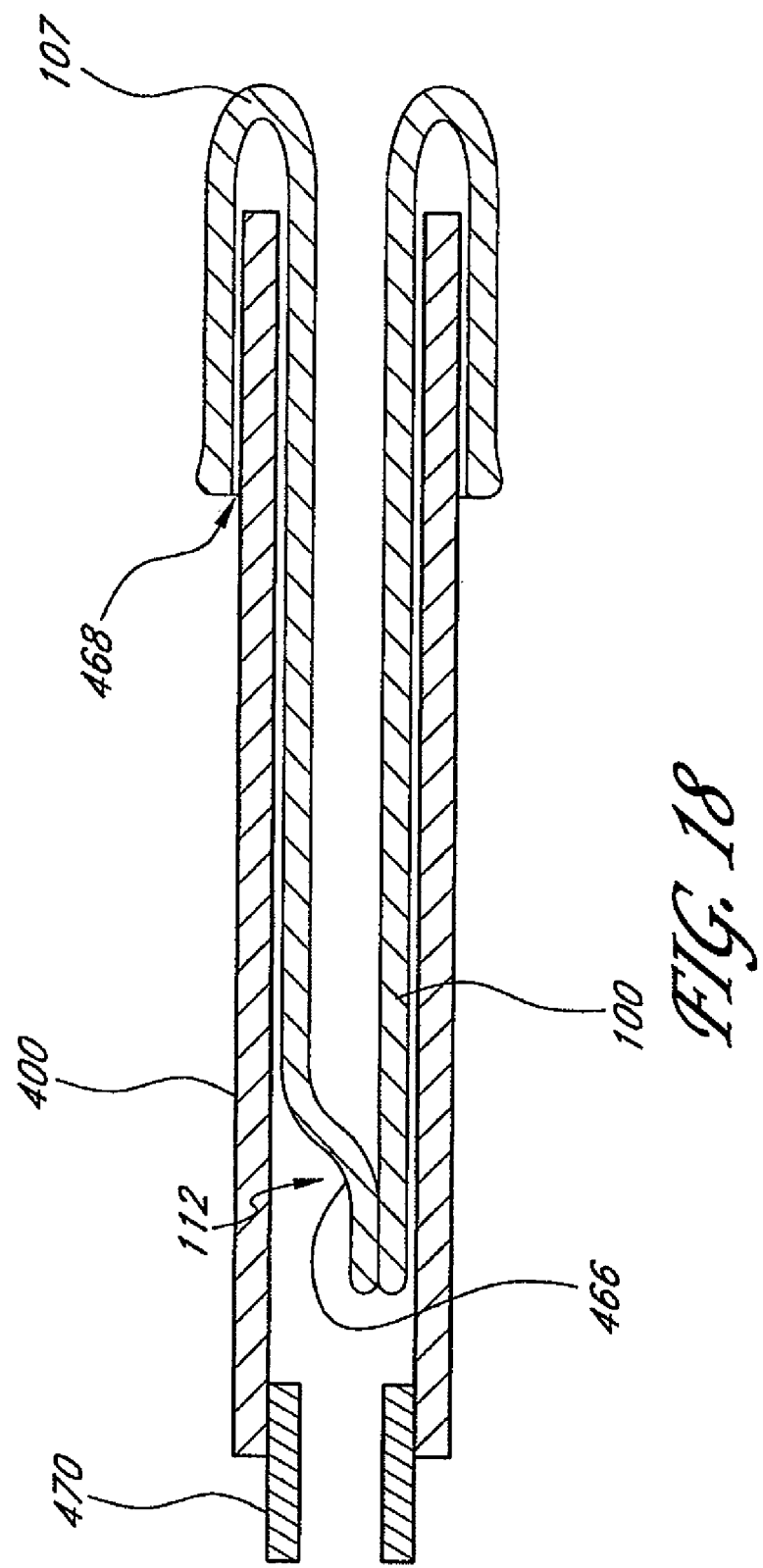
FIG. 18 is a schematic view of a filling catheter for placing a toposcopically deliverable sleeve in communication with a fluid source.

In one embodiment, filling catheter 400 passes into the lumen of sleeve 100 and a fluid-tight seal 468 is created between the proximal end of sleeve 100 and filling catheter 400, as shown in FIG. 17. In an alternate embodiment, the distal end 112 of sleeve 100 passes proximally into the lumen of filling catheter 400, the proximal end of sleeve is concentrically positioned over the distal end of filling catheter 400, and a fluid-tight seal 468 is created between the proximal, inverted, outer surface of sleeve 100 and the distal end of filling catheter 400, as shown in FIG. 18. Tubing 470 can be utilized to provide a passageway between filling catheter 400 and device 416. In this embodiment, a temporary barrier 466 can be created at distal end 112 of sleeve 100. In preferred embodiments, temporary barrier 466 is created by collapse of distal end 112 caused by the influx of fluid through filling catheter 400. In other embodiments, distal end 112 can be blocked with an absorbable or degradable plug comprising cellulose, sugar-based substances, PLA, and any other materials as would be contemplated by those skilled in the art. Any of the techniques discussed above can also be used to create temporary barrier 466.

Figure 19A:
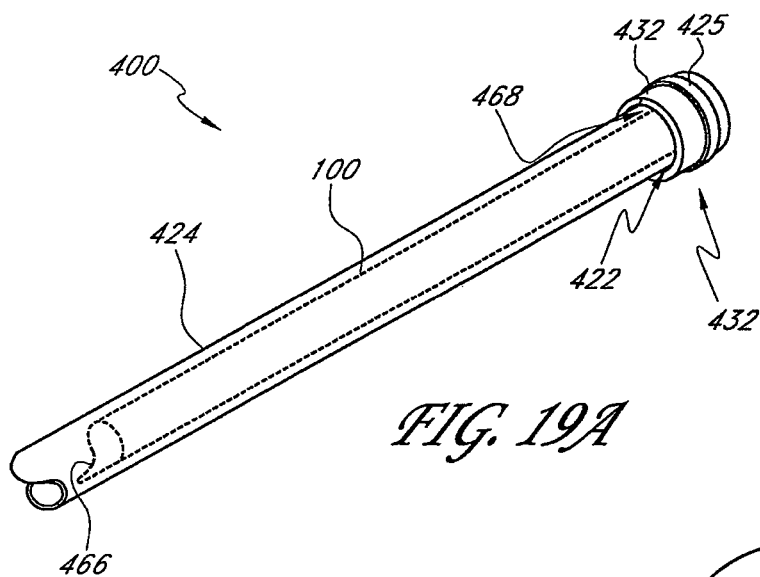
FIGS. 19A-19C show various configurations of filling catheters and toposcopic sleeves.
Figure 19B:
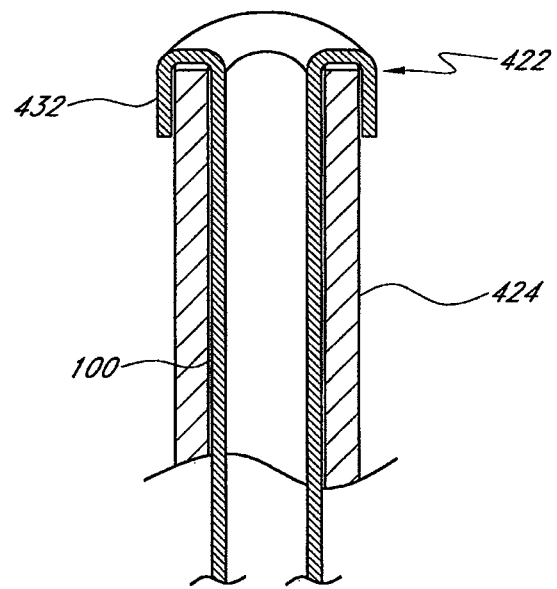
Figure 19C:
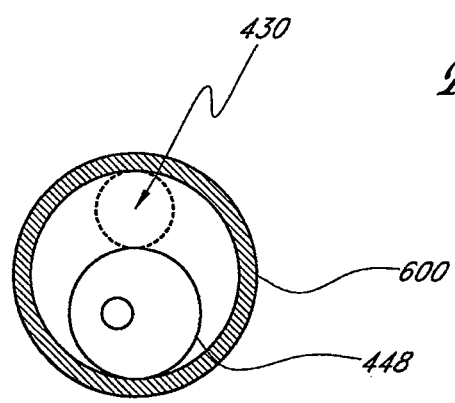

Various embodiments of filling catheter 400 are contemplated by the present invention. In one embodiment, as shown in FIG. 19A, filling catheter 400 is a pushable tube 424 with a releasable clamp 425. Clamp 425 may be released in any of a variety of ways, such as by pulling a pull wire which extends proximally through the overtube. In this embodiment sleeve 100 extends proximally through the lumen of pushable tube 424 and sleeve rim 432, or the proximal end of sleeve 100 is inverted over and releasable secured to the distal end 422 of tube 424. A fluid-tight and releasable seal 468 is created between sleeve rim 432 and the distal end of tube 424 using the releasable clamp 425, as shown in FIG. 19A. FIG. 19B is a longitudinal cross-sectional view of pushable tube 424 showing distal end 422 of tube 424 over which sleeve rim 432 is inverted. FIG. 19C is a transverse cross sectional view of overtube 600 showing the available working volume 430 remaining within the lumen of overtube 600 for filling catheter 400 when endoscope 448 is within the lumen.

In another embodiment, shown in FIGS. 20A-20D, filling catheter 400 is a balloon catheter 436. Balloon catheter 436 comprises an annular balloon 440 at its distal end. In this embodiment, as shown in FIG. 20A, sleeve 100 passes through the lumen on balloon catheter 436 and the proximal end or rim 432 of sleeve 100 is inverted over the collapsed balloon 440 of balloon catheter 436. Balloon 440 is then inflated, as shown in FIG. 20B, creating a fluid-tight seal 468 between balloon 440 and rim 432. FIG. 20C and FIG. 20D show the lumen 442 of the balloon catheter 436 before and after balloon 440 has been inflated. Lumen 442 needs to have a diameter large enough to enable sleeve 100 to fit through. The diameter of lumen 442 can range, for example, from at least about 4 mm to about 10 mm or more.

Balloon 440 may be placed in communication with a source of inflation media by way of one or two or more inflation lumen (not illustrated). The inflation lumen may extend proximally from the balloon 440 to the proximal end of the device within the wall of the balloon catheter 436 in manners well understood in the catheter body extrusion arts. Alternatively, a tubular inflation lumen may be provided by attaching a tubular element to either the outside surface or inside surface of the balloon catheter 436, for providing fluid communication between a proximal source of inflation media and the balloon 440.

In another embodiment, filling catheter 400 is a collapsible lay-flat tube 444 as shown in FIGS. 21A-21D. Tube 444 is comprised of materials, such as PEEK, PE, PU, PVC, PFA, or PTFE, and has a relatively low wall thickness that render it highly flexible and thus allow it to assume a collapsed configuration as shown in FIGS. 21A-21D and as would be understood by those skilled in the art. Because of its lay-flat configuration, tube 444 can have an inner diameter large enough to fit sleeve 100 inside but when collapsed it can fit within overtube 600 along with endoscope 448 so that it can be inserted. Tube 444 expands to fill gaps between overtube 600 and endoscope 448 when subjected to fluid pressure. Thus, tube 444 can have an uncollapsed diameter much closer to the diameter of sleeve 100 than a rigid tube and still fit through the available volume in an overtube with an endoscope in place.

Figure 21A:
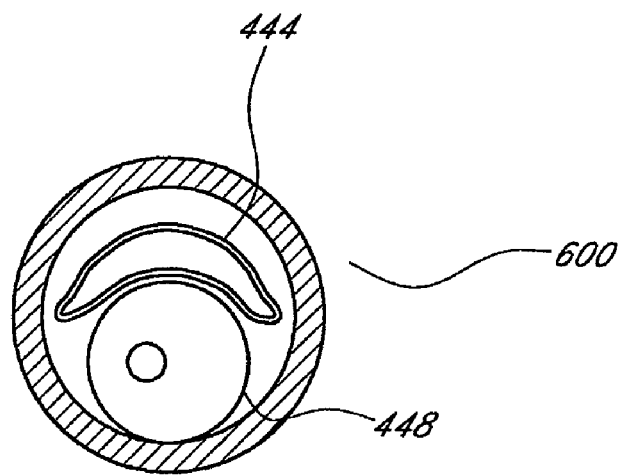
FIGS. 21A-21C illustrate an endoscopic deployment system having a collapsible lumen.
Figure 21B:
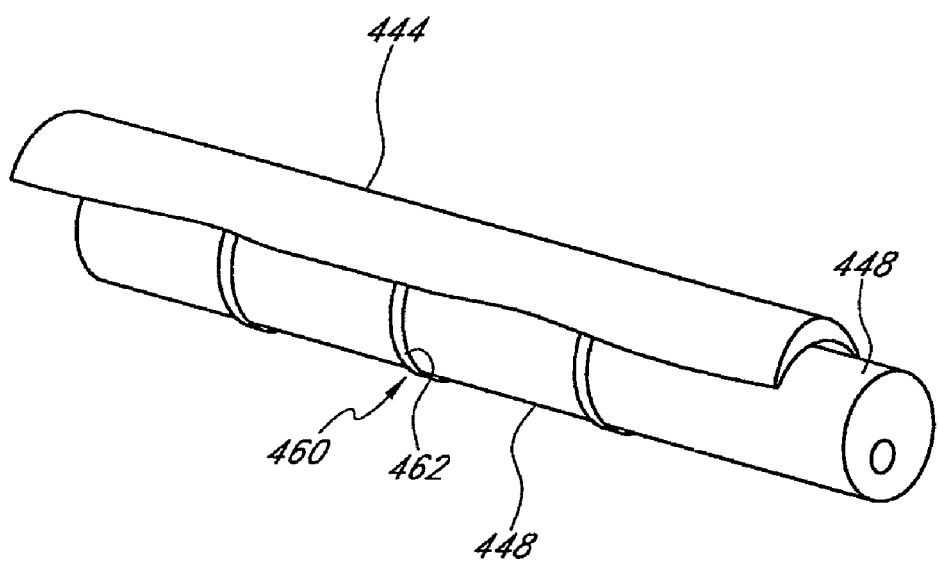

FIG. 21A is a transverse cross section of endoscope 448 and lay-flat tube 444 within overtube 600 with tube 444 lying on top of endoscope 448. Lay-flat tube 444 may be attached with means 460 to the outside of endoscope 448 as shown in FIG. 21B to aid in its insertion because the floppiness of tube 444 renders advancement on its own difficult. Alternatively, the lay flat tube can be grasped near the connection with the proximal end of the sleeve 100 and advanced with an endoscope and advanced to the desired location without any direct connection between the lay flat tube and the body of the endoscope.

Figure 21C:
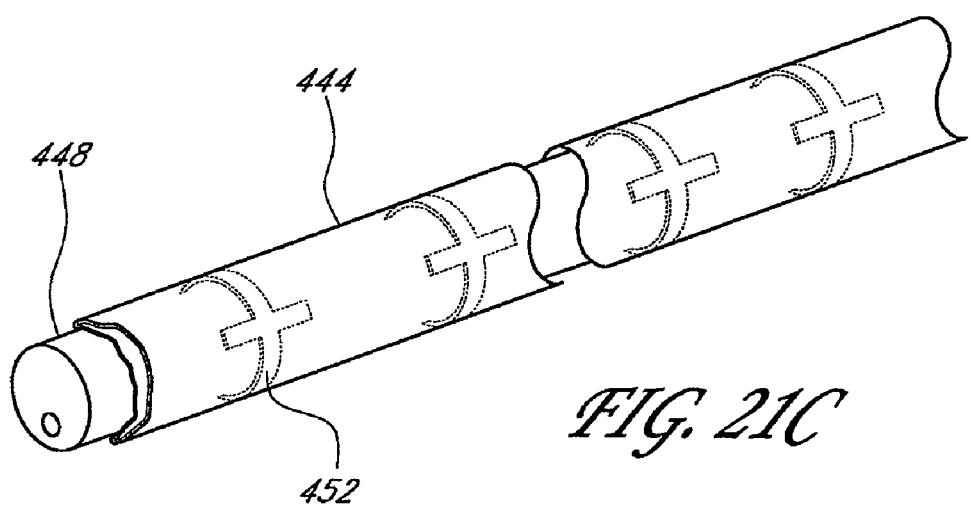

FIG. 21B depicts tube 444 lying on top of endoscope 448 and means 460 comprising bands 462 wrapped around endoscope 448 and attached to or formed as a part of the tube 444 to attach tube 444 to endoscope 448. Means 460 for attachment can also comprise attachment strips 452, as shown in FIG. 21C, that wrap around the circumference of endoscope 448 and are attached on one side of the lay flat tube 444. Tube 444 is placed on top of endoscope 448 and strips 452 are attached to endoscope 448 by virtue of the adhesive properties of the outward facing surface of strips 452 or by a spring force of the strips 452 that lock onto the housing of the endoscope. Other means 460 for attachment can be used to secure tube 444 to endoscope 448 such as a direct adhesive bond between tube 444 and endoscope 448, or others as would be understood by those skilled in the art. The means 460 for attachment should allow tube 444 to expand during filling or flushing with fluid.

Figure 22:
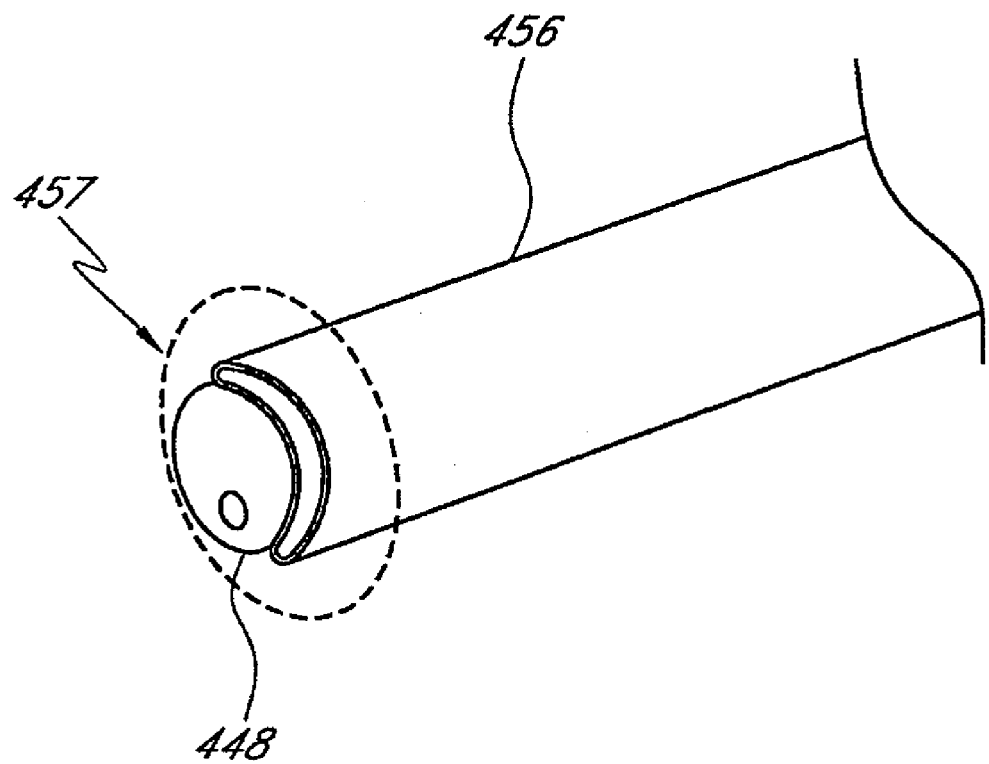
FIG. 22 illustrates an endoscopic deployment system having an external crescent shaped deployment lumen.

In other embodiments, filling catheter 400 comprises a semi-rigid (fixed cross sectional configuration) catheter 456 which lies adjacent endoscope 448. Semi-rigid catheter 456 can have a crescent or banana-shaped cross-sectional configuration as shown in FIG. 22. Banana-shaped semi-rigid catheter 456, like lay-flat tube 444 (when in the expanded configuration), has a central lumen with a cross sectional area sufficient to receive sleeve 100. Also shown in FIG. 22 is the dimension of the inner diameter 457 of overtube 600 within which endoscope 448 and catheter 456 would reside. In some embodiments, endoscope 448 has an outer diameter of about 12 mm and inner diameter 457 is about 16 mm, leaving a working volume with a transverse dimension of about 4 mm for catheter 456.

In both the lay flat tube 444 configuration and the semi-rigid catheter 456 these devices are alternative devices to the filling catheter 400. Thus, the sleeve 100 (not shown) would be inverted with the distal end 112 retracted proximally into the tube 444 or 456 and the proximal end folded over the distal end of the lay flat tube 444 or semi-rigid catheter 456.

Figure 23:
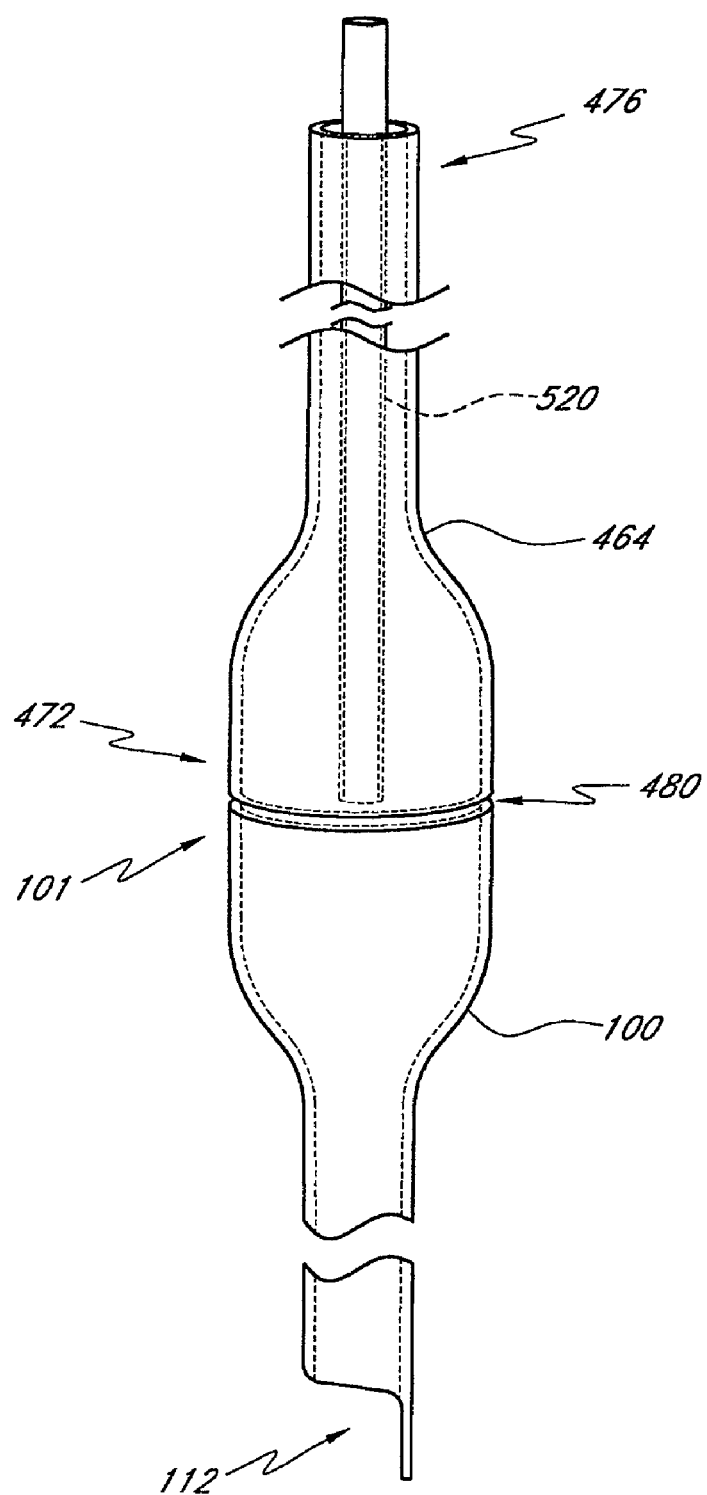
FIG. 23 is a schematic illustration of the connection between a deployment system and a toposcopically deliverable sleeve.

In the embodiment shown in FIG. 23, delivery device 464 is configured to deploy sleeve 100. In this embodiment, fluid-tight seal 468 is in the form of a releasable joint 480 created between the distal end 472 of delivery device 464 and the proximal end 101 of sleeve 100. Sleeve 100 is schematically illustrated as fully distally deployed.

An endoscope sheath 520 can be attached to or carried within delivery device 464 to house endoscope 448. The proximal end 476 of delivery device is connected to a filling tube such as tube 400 as described above or to a pump or syringe directly or via tubing. Releasable joint 480 can be a tear-away, perforated, cinched, stitched or tethered joint, or any other releasable joint that has sufficient integrity to withstand the pressure necessary to evert the sleeve 100, and that can be released from the proximal end of the device following full deployment of sleeve 100.

Figure 24:
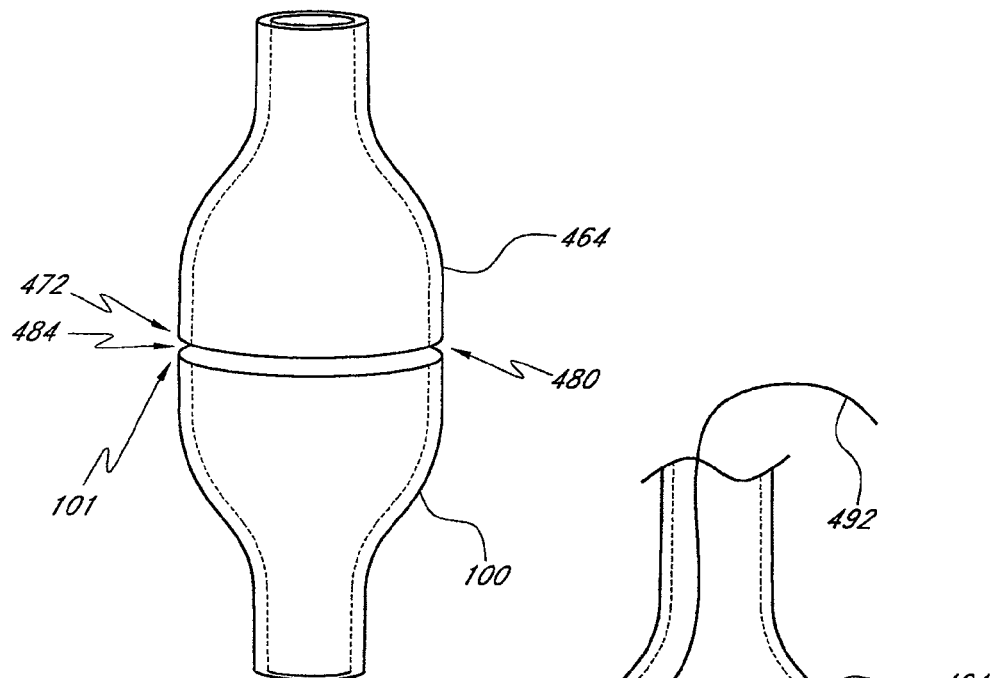
FIG. 24 is a detail view of the connection illustrated in FIG. 23.
Figure 25:
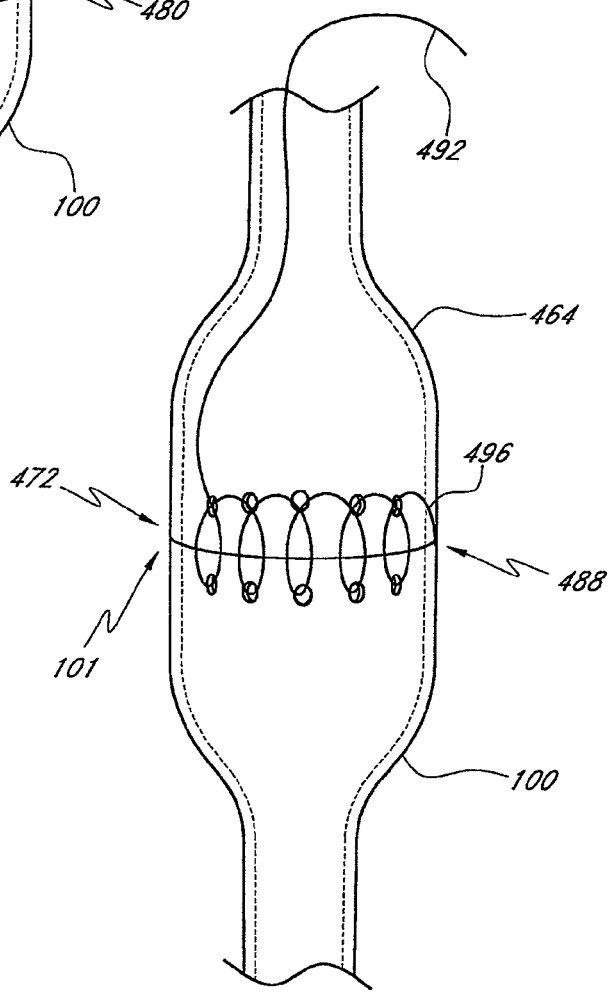
FIG. 25 is a schematic illustration of a releasable connection between the deployment system and the toposcopic sleeve.

FIG. 24 shows releasable joint 480 as a heat-bonded joint 484 that acts as a stress-concentrator for a tear-away connection. FIG. 25 shows releasable joint 480 as a running stitch attachment 488 with stitches 496 that hold delivery device 464 and sleeve 100 together with one or two or more tether lines 492 extending proximally from stitches 496 and out of the proximal end of the device. Tether lines 492 can be cut or pulled out by the clinician to release delivery device 464 from sleeve 100.

FIG. 26 shows releasable joint 480 as a curtain-rod style attachment 504. Distal end 472 of delivery device 464 and proximal end 101 of sleeve 100 each comprise a set of holes 508 which fit within each other and line up so that a retaining element such as a wire or thread 516 can be passed through all the holes 508. When wire 516 has been passed through holes 508, a compliant attachment is formed between delivery device 464 and sleeve 100. Delivery device 464 and sleeve 100 are easily separated by removing wire 516. An alternate embodiment, a loop-wire style attachment 514, is depicted in FIG. 27. Distal end 472 of delivery device 464 and proximal end 101 of sleeve 100 each comprise a set of complementary structures such as a first set and a second set of loops 512 which cooperate with each other and line up so that a wire or thread 516 can be passed through all the loops 512, forming a compliant attachment between delivery device 464 and sleeve 100.

In any of the foregoing embodiments, the complementary attachment structures may be positioned on either the sleeve 100 or the delivery device 464 spaced apart from the corresponding end, so that the sleeve 100 extends for an overlap distance concentrically inside or concentrically outside of the distal end 472 of delivery device 464. As an alternative, or in addition, an annular seal in the form of a tubular skirt may be attached to either the sleeve 100 or delivery device 464, and extend a sufficient axial distance to span the releasable joint 480. In one implementation, a polymeric tubular skirt extends distally from the distal end 472 of delivery device 464, and into the proximal end 101 of sleeve 100 by at least about 1 cm, and, in some embodiments, at least about 2 cm. The skirt may comprise any of a variety of materials, such as silicone, which will allow it to be pressed radially outwardly against the releasable joint 480 under the influence of pressure from the everting fluid. The annular sealing skirt thus cooperates with a proximal portion of the sleeve 100 in the nature of a valve. One or both of the corresponding surfaces may be provided with a pressure sensitive adhesive or other coating, to facilitate the seal, yet be severable by proximal traction on the delivery device 464.

Figures 28A, 28B:
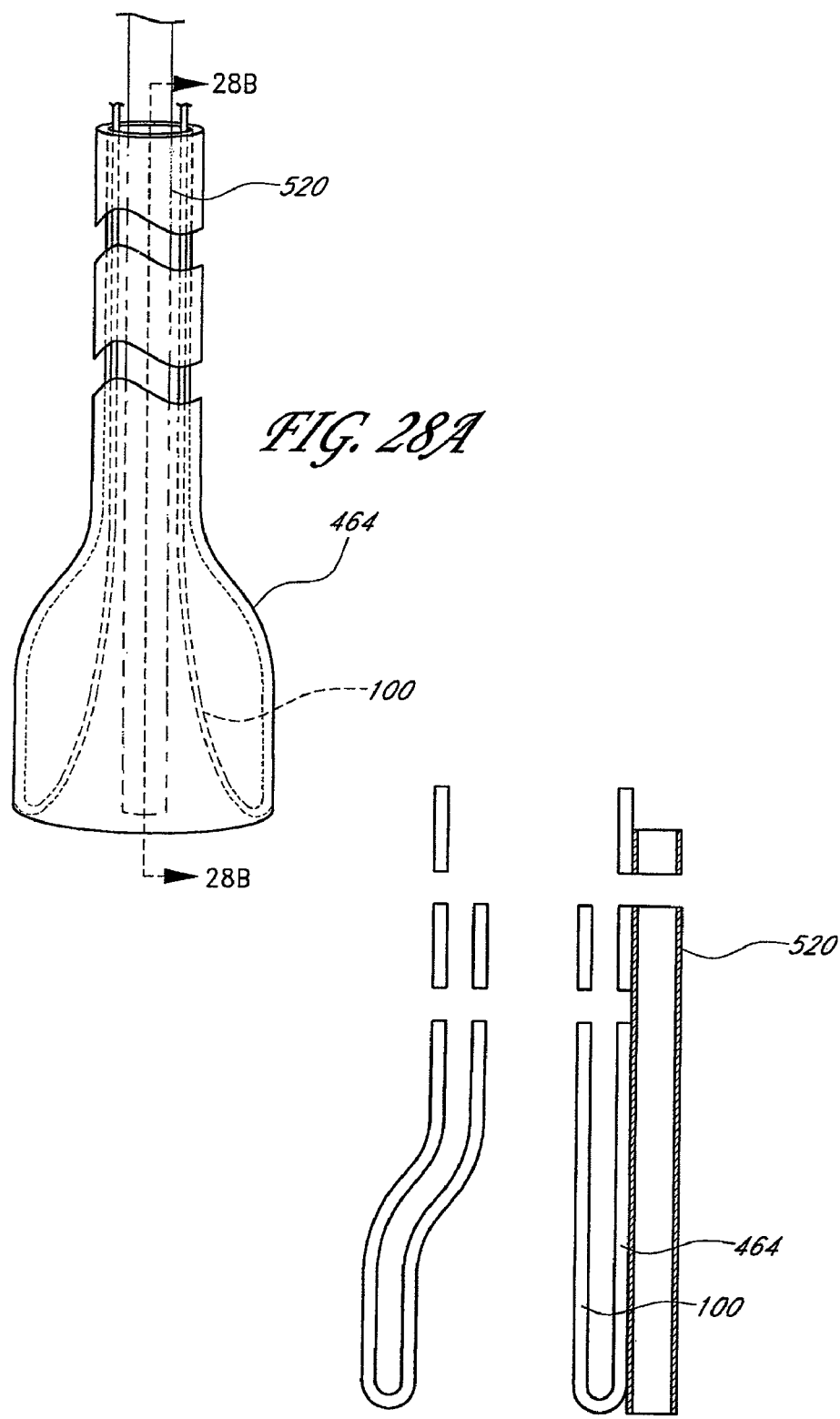
FIG. 28A is a schematic illustration of a deployment device having a toposcopically deliverable sleeve fully retracted proximally through the deployment device.
FIG. 28B is a cross sectional view taken along the line 28B-28B in FIG. 28A.

As shown in FIGS. 28A-28B, the proximal end of sleeve 100 is releasably attached to the distal end of delivery device 464 using any of the releasable joints discussed above and the body of sleeve 100 is inverted within delivery device 464. After delivery device 464 is positioned, sleeve 100 is distally deployed into place and detached from device 464. FIG. 28A is a side view of delivery device 464 with sleeve 100 inverted within and an endoscope sheath 520 attached to the back side of delivery device 464. FIG. 28B is a cross-sectional view of FIG. 28A.

Many advantages are associated with toposcopic delivery of sleeve 100. Toposcopic delivery allows sleeve 100 to be delivered without moving sleeve 100 over and against the endothelium of the esophagus, stomach, and intestines. Sleeve 100 when delivered toposcopically can navigate tortuous anatomy. When sleeve 100 is delivered toposcopically, inverted portions of sleeve 100 deploy an axial elongation without axial sliding against the tissue such that there is no tissue abrasion and no kinks or twists are created in sleeve 100. Toposcopic delivery also requires minimal instrumentation development. The sleeve 100 delivered toposcopically is not limited to being attached to the cuff at the GEJ. The method of delivering an intestinal sleeve with a toposcopic delivery technique as described above can be used to attach a sleeve to the pylorus, the duodenal bulb, the lower portion of the stomach or anywhere else where it is deemed to be clinically beneficial.

Methods of insertion and retrieval of a gastrointestinal sleeve device are also described in the parent application. In addition to the methods described therein, a GI sleeve can be inserted and/or retrieved using a flexible endoscope. A skilled GI endoscopist can "drive" a special endoscope (an enteroscope) through the duodenum and deep into the jejunum. Because of its small size, a pediatric colonoscope can be used to access an area further down the intestine. With proper interfacing structure on a GI sleeve, the sleeve can piggyback on the endoscope as it is driven into the jejunum and then released with its distal end left in the jejunum when the endoscope is retracted and removed from the body. This can be accomplished perorally either before or after attachment of the proximal end of the sleeve to tissue or to a cuff at the GEJ 106 or some other clinically desirable location.

Various structures can be used as an interface between the endoscope and the distal end of the GI sleeve device. If the sleeve device has a solid distal end or other graspable portion, such as a tab or loop near the distal end, a standard or custom endoscopic snare or grasper can be extended through the endoscope working channel to grasp the sleeve device. Alternatively, the distal end of the sleeve device can be configured with a socket or pocket to engage a flexible pusher, which may be configured as a rod, tube or guidewire. As another alternative, the sleeve device can be configured with a distal end that can be cut off to release the device. The distal end of the sleeve device is grasped with a snare or the like extended through the endoscope working channel. Once the sleeve device is delivered far enough distally in the GI tract, the distal end of the sleeve device is cut off to release the device.

In one embodiment, delivery of the sleeve device to an area sufficiently far down the intestine is facilitated by attaching a traction structure, such as a mercury ball or liquid filled balloon, that increases the likelihood that the sleeve will be pulled down the intestine, to the distal end of the sleeve. During peristalsis the intestinal wall grabs hold of the traction structure and pulls it along with the distal end of the sleeve down the intestine.

In one embodiment deployment of the sleeve device and/or T-tags is achieved with the use of a remote controlled robotic endoscope. Generally, a remote controlled robotic endoscope comprises a user interface, a control device, and an operating unit. Commands can be inputted by an operator into the user interface to activate the control device which in turn guides the operating unit in three dimensions. The operating unit, in one embodiment, can be a fastener deployment head carried by a catheter which is positionable within the gastrointestinal tract and capable of attaching various fastener structures such as sutures and T-tags in response to commands received by the user interface. Monitors that display physical data and images of the anatomy to aid in navigation of the operating unit may also be used with a remote controlled robotic endoscope. Such an endoscope could scale the operator's movements such that large movements of the operator would translate into the smaller movements that may be required to maneuver the endoscope within the gastrointestinal tract. One embodiment of a remote controlled robotic endoscope is described in "Radiocontrolled Movement of a Robot Endoscope in the Human Gastrointestinal Tract," by P. Swain, T. Mills, B. Kelleher, L. Schmitz, S. Mosse, P. Burke, K. Ikeda, and A. Fritscher-Ravens.

Anchor Insertion Safety Devices

Figure 10:
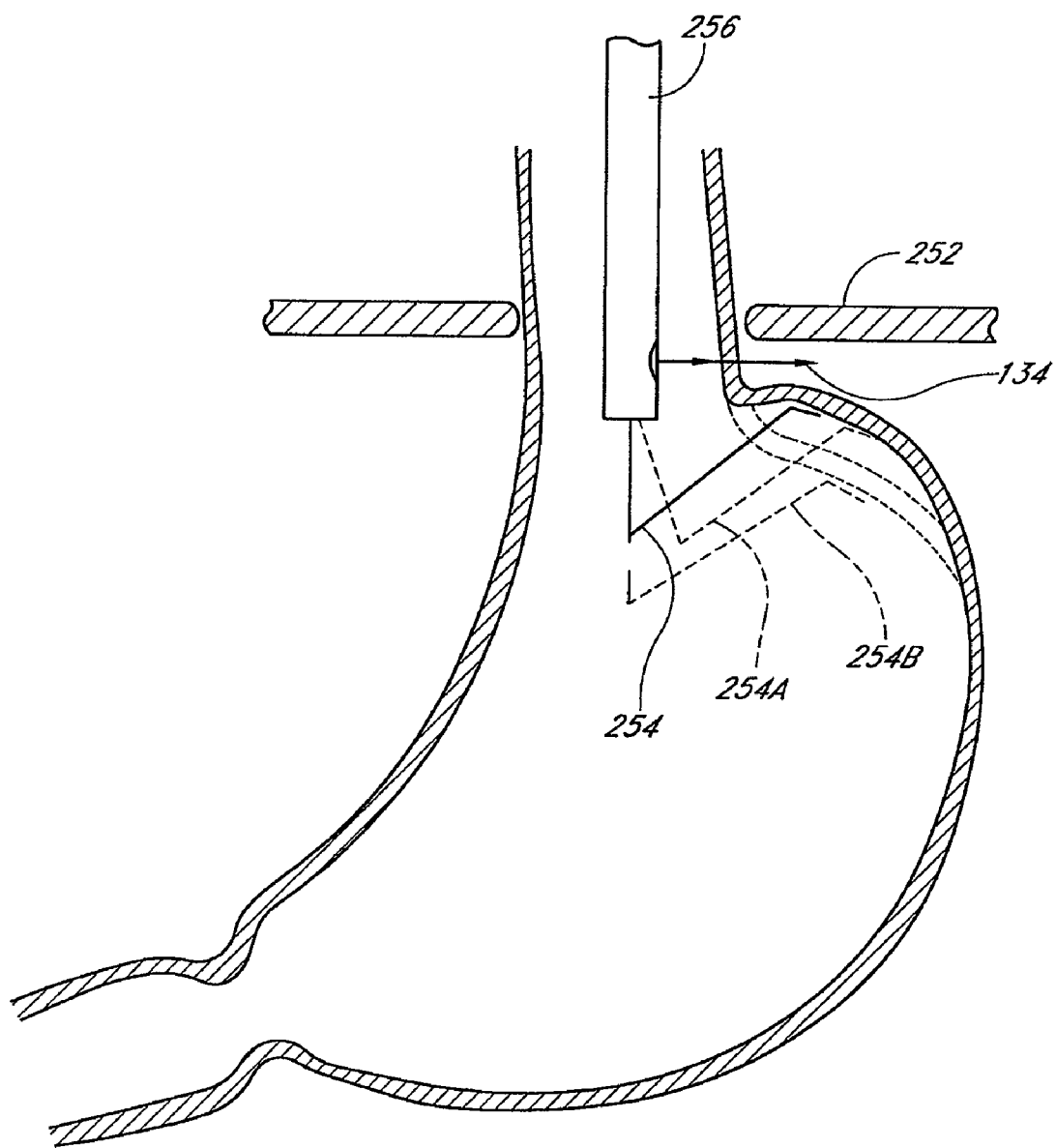
FIG. 10 illustrates a method and apparatus for placing T-tag fasteners at the gastroesophageal junction (GEJ).
Figure 11A:
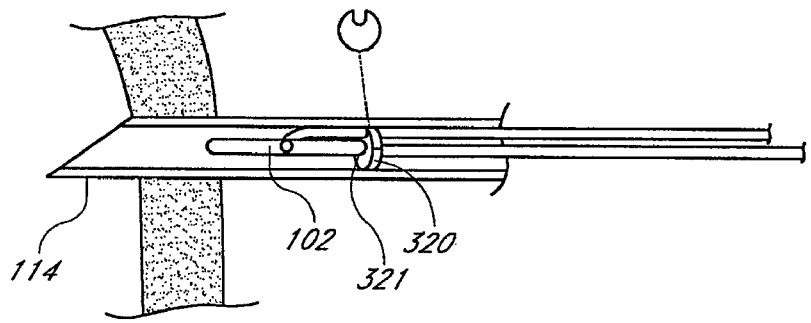
FIGS. 11A-11D show a method of T-tag fastener delivery.
Figure 11B:
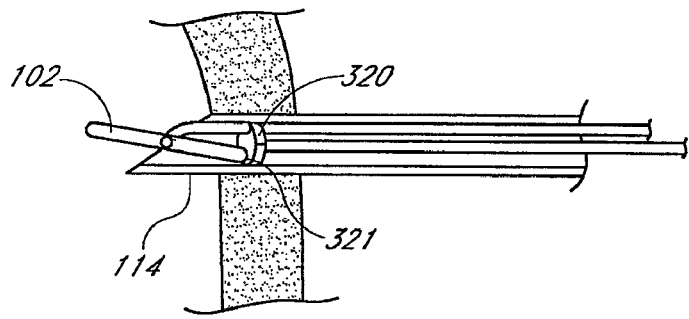
Figure 11C:
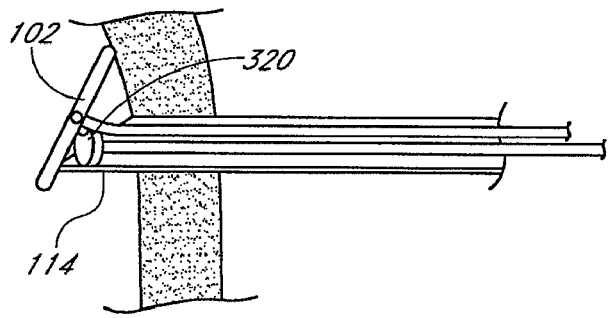
Figure 11D:
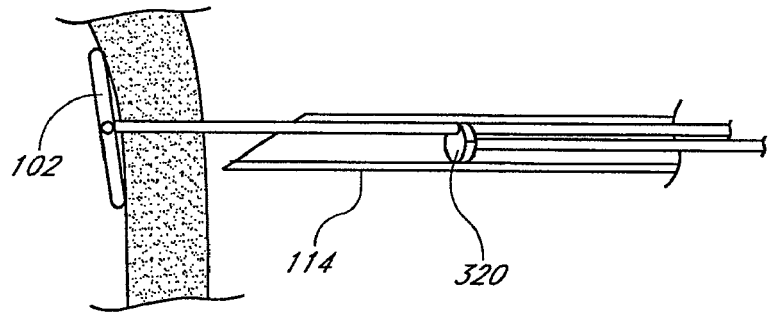

When placing T-tag fasteners or other fasteners in the region of the GEJ 106, it is important to avoid other anatomical structures in the vicinity of the stomach and esophagus. One method for this is to create a safe space behind the GEJ 106 for deploying the fasteners. One method to accomplish this is described in the parent application Ser. No. 10/698,148. Alternatively, one can take advantage of the fact that the proximal stomach generally lies just below the diaphragm when the patient is in a head-up position. Space will be created between the stomach and diaphragm into which transmural fasteners can be safely placed. This safe space can be increased by having the patient inhale deeply while in a head-up position to push the stomach down with the diaphragm, then exhale to lift the diaphragm up off of the stomach. Preferably, the fasteners 134 will be delivered parallel to the diaphragm 252, as shown in FIG. 10, though other orientations are possible. FIG. 10 also shows an optional stomach traction device 254 deployed through the working channel of an endoscope 256 that helps to facilitate safe deployment of the fasteners 134 in the GEJ 106 region. The traction device

254 can be used to retract the gastric wall laterally 254A and/or distally 254B to create a safe place for deployment of the fasteners 134. Due to anatomic variations and pathology, the position of the diaphragm relative to the stomach and GEJ 106 should be confirmed prior to using this technique.

Figure 56A:
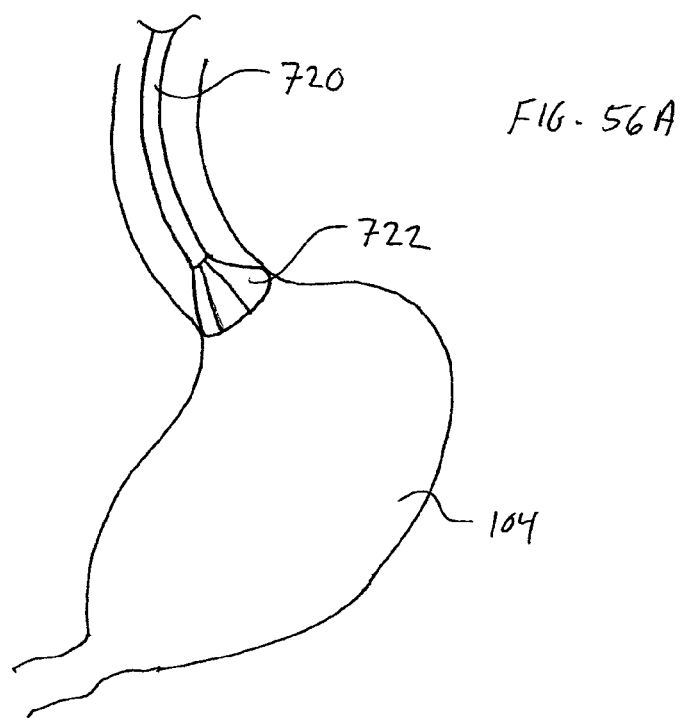
FIG. 56A is a schematic illustration of an internal tissue retractor positioned in the vicinity of the GEJ.

Alternatively or in addition, pneumoperitoneum can be used to create a safe space around the stomach and esophagus. Pneumoperitoneal pressure will tend to collapse the stomach away from other surrounding organs and would be balanced by the pressure used to endoscopically insufflate the stomach for improved visualization and access. Because the use of pneumoperitoneum will tend to reduce the working space as the lumen collapses, there are devices which can be used like a internal retractor to keep the target tissue in a position where it can be easily visualized and the anchors reproducible placed. An example of one such device is in FIGS. 56A and 56B. An overtube 720 with a distal expandable flange 722 that can form a funnel with the large end of the funnel on the distal end. When pneumoperitoneal pressure is applied the tissue will tend to collapse around the distal wide end of the funnel. This will present the tissue in a plane more perpendicular to the end of the endoscope to facilitate driving the anchors.

Any of a variety of radially largeable structures may be utilized to generate the radially expandable flange 722. For example, a plurality of distally extending fingers or petals may be pivotably or moveably attached at their proximal end to the overtube 720. The distal end of the petals may be radially enlarged such as by proximal traction on one or more pull wires extending axially through the overtube 720. Alternatively, as schematically illustrated in FIG. 56C, an inflatable balloon may be positioned within the expandable flange 722 to advance it from the reduced configuration to the enlarged configuration.

Figure 56B:
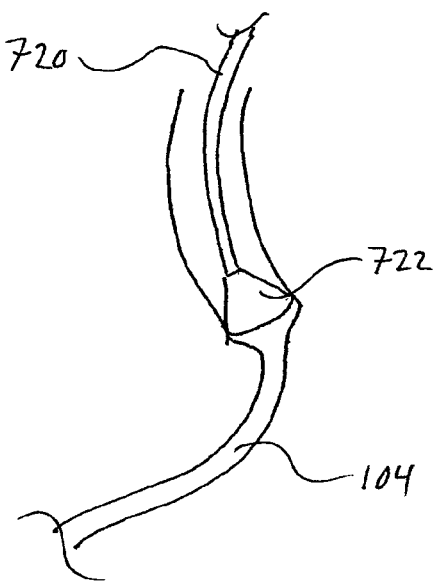
FIG. 56B is a schematic illustration as in FIG. 56A, following increase in the pneumoperitoneal pressure, to collapse the stomach.
Figure 56D:
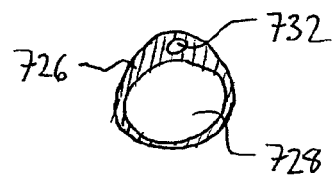
FIG. 56D is a cross sectional view taken along the line 56D-56D in FIG. 56C.
Figure 56C:
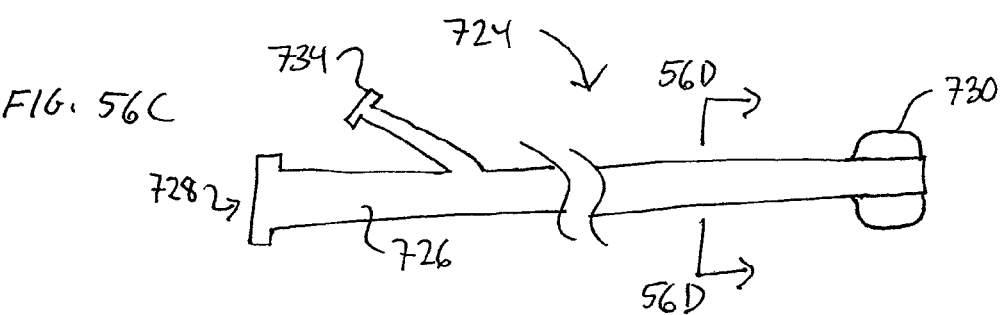
FIG. 56C is a schematic view of a balloon catheter for manipulating the internal tissue retractor.

Referring to FIG. 56C, an expander catheter 724 is disclosed. Expander catheter 724 comprises an elongate flexible tubular body, such as for distal advance through the central lumen of an overtube 720. A central lumen 728 extends throughout the length of the tubular body 726, such as for enabling the passage of tissue anchor deployment catheters or other devices. The tubular body 726 is additionally provided with a distal annular inflatable balloon 730. The inflatable balloon 730 is configured for positioning within the expandable flange 722, and inflation to radially outwardly enlarge the flange 722. Inflatable balloon 730 is in communication with a balloon inflation port 734 by way of an inflation lumen 732.

The balloon 730 may be radially expanded within the expandable flange 722, to resist collapse of the local anatomy, as schematically illustrated in FIG. 56B. Elevated pneumoperitoneal pressure will tend to collapse the stomach 104, presenting a tissue target zone at the distal end of the expanded radially flange 722. Following deployment of tissue anchors or other tissue manipulation, the balloon 730 may be deflated, the expandable flange 722 permitted to collapse, and the overtube 720 and associated devices may be proximally withdrawn from the patient.

Other tactics to avoid other anatomical structures in the vicinity of the stomach and esophagus include the use of imaging techniques such as fluoroscopy, esophageal ultrasound imaging, external ultrasound imaging and/or Doppler imaging when placing fasteners. Alternatively or in addition an "endoscopic compass" can be used to provide a reference for orienting the endoscope when using fastening devices. A small magnetized needle (i.e. a compass needle) is placed near the distal end of the endoscope where it can be viewed by the operator through the endoscope. A magnet is placed on the patient to provide a reference point for the compass, for example the reference magnet can be placed on the patient's back directly over the spine. The compass needle will point toward the reference magnet on the spine. Using the compass needle as a reference, the operator will be able to avoid inadvertently puncturing the aorta, which lies directly posterior to the esophagus.

The concept of the Veress needle can be adapted for avoiding puncturing other anatomical structures in the vicinity of the stomach and esophagus during endoscopic attachment of devices near the GEJ 106. A Veress needle is a needle equipped with a spring-loaded obturator that is often used for insufflation of the abdomen in laparoscopic surgery. A long, flexible device with a needle at the distal end and a spring-loaded obturator within the needle would be used to safely puncture the gastric or esophageal wall. Once the needle has passed through the wall, the spring-loaded obturator advances automatically to avoid damage to any surrounding tissues. A delivery cannula can be advanced over the needle and the needle can be exchanged with a fastener delivery device. Alternatively, this concept can be adapted directly into the fastener delivery device. A T-tag fastener or the like would be spring-loaded into the lumen of a delivery cannula so that it would be ejected out of the lumen immediately after the cannula has traversed the gastric or esophageal wall. Similar safety needles may be configured as the needle tip of the anchor inserter or as a separate needle. Safety needle designs can comprise a spring-loaded tip that either retracts the needle tip or deploys a cover over the needle tip when the tissue is pierced completely through. Retraction of the needle tip or deployment of the cover can be triggered by the change of pressure experienced by the needle tip as it emerges from the outer surface of the tissue. Deployment of the cover can also be mechanically triggered such that when the cover moves through the tissue with the needle tip it is held back by the tissue until it emerges from the outer surface of the tissue and is then free to slide over the needle tip.

Another method for avoiding deploying fasteners into the aorta would involve a small diameter needle with a flow detector (e.g. a Doppler flow sensor) or pressure detector for detecting blood flow or blood pressure. Alternatively, a flow detector or pressure detector can be mounted on a separate guidewire inserted through the needle. The flow detector can be used to detect blood flow before the wall of the aorta is punctured. Alternatively, if backflow of blood or blood pressure is detected, indicating that the needle has punctured the aorta, the needle will be withdrawn and a fastener will not be delivered at that site. The small diameter puncture in the aorta should heal without complications.

In other embodiments, a guidewire can be used to pierce the tissue wall prior to introduction of anchor inserter and thereby determine if there are structures near the outer surface of the tissue that can be damaged, such as the aorta. Guidewire is sufficiently small such that no serious bleeding or other complications would be incurred even if a structure were punctured. In some embodiments, guidewire utilizes monopolar or bipolar RF current as an aid in penetrating the tissue. Guidewire can be used to pierce various locations of the tissue wall to find an area near the outer surface of the tissue that is free of structures that could potentially be damaged by anchor inserter. After such an area is found, anchor inserter is advanced using any known advancement methods, including those incorporating over-the-wire or monorail type configurations. In some embodiments, anchor inserter comprises a tapered sheath that can be advanced into the puncture in the tissue wall to gradually dilate the puncture until it attains a desired outer diameter prior to deployment of an anchor. The anchor can be cannulated and placed over guidewire so as to minimize the outer diameter of the puncture required for anchor deployment. A needle with a large diameter can also be used to dilate the puncture. In another embodiment, the puncture is enlarged by expanding an expandable device, such as a balloon, mounted on guidewire. This embodiment may be associated with faster healing and less risk to surrounding structures or tissue.

In some embodiments, a needle comprising a pressure sensing element is used to pierce the tissue wall. In one embodiment, the pressure sensing element can sense the pressure on needle as it is advanced and signal to the user when the pressure drops off as the needle penetrates the serosa. In an alternate embodiment, the needle can sense the ambient pressure surrounding the tip of the needle when it is in the tissue and signal to the user when this pressure changes as the tip emerges from the tissue. In some embodiments, pressure sensing element can be a piezo-electric crystal in the body of the needle and can be monitored electronically.

In other embodiments, the needle can comprise an electrode that measures the impedance of a charge delivered into the tissue as the needle penetrates the tissue and alerts the user when contact with the tissue is broken as the needle emerges from the tissue.

In embodiments comprising needles with a pressure sensing element or an electrode, any of the needle tip retractor elements or protective sheaths described herein can also be triggered when the needle has penetrated the tissue.

Alternatively or in addition, the organs and other anatomical structures in the vicinity of the stomach and esophagus can be protected during endoscopic attachment techniques by using a depth stop on the needle or delivery cannula to prevent it from penetrating farther than necessary to traverse the gastric or esophageal wall. Examples of fastener delivery devices with a depth stop to protect nearby organs and structures are described in U.S. provisional patent application 60/569,442.

In other embodiments, the needle comprises a spring loaded tip that limits the distance that the needle can travel. The spring loaded tip can comprise a spring that controls the speed or force with which the needle is advanced. For example, the spring can be an air spring with a release port near the distal end of the throw such that all force is released near the end of needle travel. There can be a hard stop to prevent penetration deeper than desired. Thus, if the needle hits any structure(s) after emerging from the serosal surface, the tip would rebound without any resistance.

Various embodiments for distal protection or protection of the inner or mucosal surface of the tissue are also disclosed per aspects of the present invention.

In one embodiment, a device is advanced through the tissue in a small or collapsed configuration as the needle advances through the tissue. When the needle penetrates the tissue at the serosal surface, the device is expanded, for example like an umbrella, covering an area of the serosal surface of the tissue. In its expanded configuration, the device is atraumatic to surrounding structures and also acts as a barrier to prevent needles and other objects that are advanced through the same or a proximate path through the tissue from damaging surrounding tissue or structures. The umbrella device can be cannulated to allow placement over a wire or a pressure sensing needle as described elsewhere.

Figure 51A:
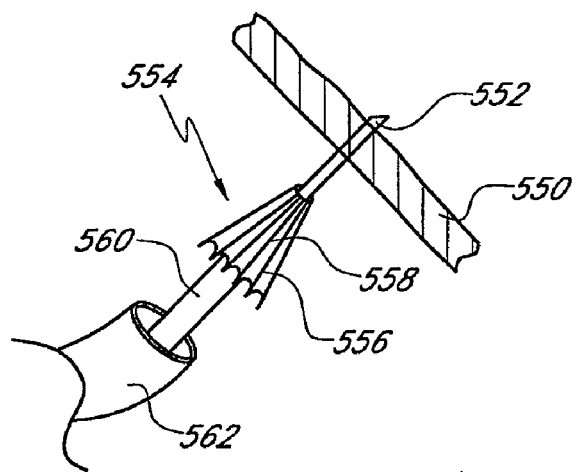
FIGS. 51A-51C illustrate deployment of a distal protection device through the esophageal wall.
Figure 51B:
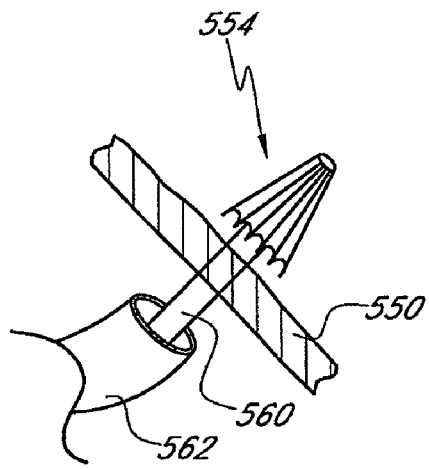
Figure 51C:
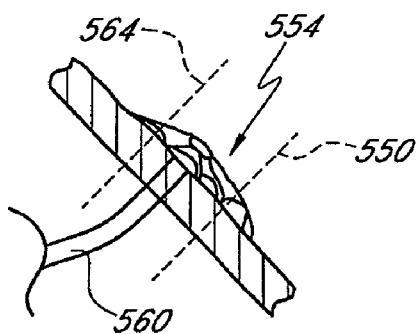

One example of an enlargable barrier is illustrated in FIGS. 51A through 51C. Referring to FIG. 51A, a tissue wall 550 may represent a portion of the wall of the stomach, the esophagus, the intestine, or other tissue plane in the body. An advance needle 552 is advanced through the tissue wall 550. Advance needle 552 may comprise a hollow hypotube needle, a solid core sharpened wire, or other structure capable of penetrating the tissue wall 550.

An enlargeable barrier 554 is illustrated as concentrically carried over the advance needle 552. In the illustrated embodiment, the barrier 554 comprises a plurality of struts 556 which are pivotable or hingeably connected at one end, such as the distal end as illustrated, having a free proximal end. The struts may be moveable between a first configuration as illustrated in FIG. 51A, in which the struts are aligned with the longitudinal axis of the advance needle 552, and a second position illustrated in FIG. 51C, in which the struts are inclined radially outwardly to enlarge the transverse area of the barrier 554. The struts 556 may be connected by an impenetrable membrane 558. The membrane 558 may comprise any of a variety of structures, such as a polymeric or metal film, or woven filaments or other fabric configurations. The membrane 558 is preferably relatively impenetrable by the distal end of the tissue anchor or tissue anchor implantation device. Rather, the impenetrable membrane 558 is preferably configured to either stop distal progress of an anchor deployment device, or to be pushed distally away from the tissue wall 550 by an anchor deployment device which is advanced through the tissue wall 550. In this manner, distal advance of the anchor deployment device pushes the barrier 554 distally, thereby pushing delicate anatomical structures distally and preventing puncture by the anchor deployment device.

As illustrated in FIGS. 51B and 51C, the barrier 554 is preferably advanced through the tissue wall 550 while in the first, reduced cross sectional configuration. The barrier 554 is thereafter converted to the second, enlarged cross sectional configuration to create a protective barrier. Once in position as illustrated in FIG. 51C, the barrier can be utilized to protect adjacent structures from needle punctures advanced along one or more axes 564 which are within the footprint of the enlarged device. Following anchor deployment, the barrier 554 may be collapsed back to its first configuration, and withdrawn from the tissue wall 550.

An outer tubular sleeve 562 may be provided for coaxially receiving the barrier 554. The sleeve 562 may be advanced through the tissue wall 550 prior to deployment of the barrier 554. Any of a variety of pull wires, spring biasing configurations or other structures may be utilized to move the barrier 554 between the first, reduced configuration and the second, enlarged configuration.

The barrier 554 may alternatively be provided on the proximally facing surface of an inflatable balloon (not illustrated). In this implementation, the balloon is inflated on the distal (serosal) surface of tissue wall 550. The introduction axis 564 of a tissue anchor may be directed at the surface of the balloon, in which case the surface of a balloon is reinforced sufficiently that it resists puncture and instead advances distally to push sensitive structures out of the way. Alternatively, the balloon can be configured such that the axis of introduction 564 of a tissue anchor advances along side but not intersecting with the balloon. This configuration takes advantage of the free space created surrounding the balloon, between the serosal surface of tissue wall 550 and anatomical structures pushed out of the way by the inflated balloon.

In another embodiment, a device creates a space around the serosal location by manipulating the mucosal surface where the needle is inserted. For example, the device can grab the tissue around this location and manipulate it to create folds comprising a space on the serosal side. The tissue can be grabbed using a variety of mechanisms as would be understood by those skilled in the art, including vacuum-assisted grabbing and corkscrewing into the tissue and then pulling to make a plication or fold so there is a safe space on the serosal side of the fold.

In yet another embodiment, the needle is curved preferably so that it takes at least between a 60° and 120° bend, such that the radius of the curve is approximately equal to the thickness of the tissue wall. Thus, when the tip of the needle pierces the serosal surface of the tissue, the needle will follow an arcuate path back through the esophageal wall and emerge from the mucosal surface.

Structures surrounding the location near the mucosal surface that the needle penetrates can also be visualized using, for example, TEE or Endoscopic Ultrasound. Any other means as would be understood by those skilled in the art can be used to determine when the needle has penetrated the serosal surface and when structures and tissue surrounding either the location of serosal or mucosal penetration must be protected.

Measuring Stomach and/or Esophageal Wall Thickness

Measurements of the thickness of the wall of tissue in the target region of anchor 604 deployment can be used to determine, for example, optimum lengths for anchor tensioning devices so that excessive pressure, resulting in the potential for necrosis, is not applied to tissue. Measurements of tissue thickness can also help in determining when anchor inserter 652 has successfully pierced the desired layers of tissue, including the serosa. Furthermore, measurements of tissue thickness can help identify areas in which anchors 604 should not be placed. In some embodiments, tissue thickness measurements are taken by devices that pierce the tissue. In other embodiments, tissue thickness measurements are taken by devices that do not pierce the tissue.

Piercing measurement devices measure the thickness of the tissue by piercing the tissue and taking measurements from the outside surface to the inside surface. One embodiment of a piercing device is an L-shaped wire. A small puncture in the tissue wall can be made with the tip of the L-shaped wire or with a separate needle. A first leg of the L-shaped wire can then be advanced through the puncture and then laid flat against the outer (serosal) surface of the tissue so that the second leg of the L-shaped wire, which comprises markers around its circumference, traverses the tissue thickness. Because the wire is placed such that the area at which the first leg meets the second leg corresponds to the outer surface of the tissue, the markers, which span at least a portion of the length of the second leg, can indicate the thickness of the tissue by marking the point at which the second leg emerges from the inside surface of the tissue. The markers on the second leg can comprise grooves, painted-on marks, or any other indicators of distance traversed, as would be contemplated by those skilled in the art.

In another embodiment, the piercing device has a T-shaped configuration when expanded. T-shaped device is deployed in a collapsed position, with the two arms that form the top horizontal portion of the T of the device lying against the vertical portion of the T of the device or extending distally in parallel to each other. Once deployed from the inner surface to the outer surface of the tissue, the arms are expanded so that they form the horizontal portion of the T and lie against the outer surface of the tissue. The vertical portion of the T comprises markers around its circumference, similar to the markers described above in connection with the L-shaped wire. Thus, because the area at which the vertical portion meets the horizontal portion corresponds to the outer surface of the tissue, the markers can indicate the thickness of the tissue by marking the point at which the vertical portion emerges from the inside surface of the tissue. The arms of the T-shaped device can then be collapsed so that the device can be removed.

Thickness measurement indicium can be incorporated into any device as described above which crosses the tissue layer before deploying the anchors, for example the umbrella like distal protection device as described above could have marks along the shaft of the device so after the umbrella is deployed it can be moved proximally to come into contact with the serosa and then a measurement can be taken. In addition, as with all the devices as described above the markers for measuring thickness could be gauged on the proximal end of the device outside the body. One example of this design would be to have a linearly movable gauging element on the mucosal side of the tissue thickness measuring device that is a fixed distance away from the serosal contact point of the measuring device, for example it could be 15 mm away from the bend of the "L" shaped device. The gauging element is controlled from the proximal end of the device by the operator. When the proximal end of the gauging element is advanced a marker on the proximal end is revealed which indicates the distance advanced. Using this method, once the gauging element comes into contact with the mucosal tissue the operator could read how far it was advanced and determine the thickness of the tissue without having to remove the device or try to read a marker inside the patients GI tract.

Non-piercing measurement devices include, for example, mechanical devices and energy-based devices. One example of a mechanical non-piercing device is a caliper-like device that takes a plication-like bite of tissue. The wall thickness would equal half the measured distance through the plication because the bite of tissue would include two thicknesses of tissue. Some examples of energy-based non-piercing devices for measuring tissue thickness are imaging devices such as transesophageal ultrasound (TEE) or endoscopic ultrasound (EUS) devices that can be placed at various areas around the esophagus or stomach. A probe with an electrode can be placed against the tissue wall of the stomach, and a second probe can be placed at another location in the target region for anchor 604 deployment or near the GEJ 106. The impedance can then be measured between the two probes. This process can repeated for various positions of the two probes. Based on the measurements obtained, the tissue wall thickness can be determined. In some embodiments, more than two probes are used to obtain thickness measurements.

FIGS. 11A-11D illustrate a simplified view of delivery of a T-tag fastener showing the serosal anchor and tension element (suture) of a T-tag fastener and the delivery cannula with a pusher therein. In actual application, the entire delivery assembly would include an endoscopic delivery device (not shown), with the delivery cannula carried piggyback by the endoscope or deployed through the working channel of the endoscopic delivery channel. Also, in actual application the T-tag fastener could attach an attachment device such as a cuff to a gastrointestinal sleeve device through a grommet or hole in the cuff and/or sleeve device.

All or a portion of the fastener can be coated and/or made with a material that will encourage tissue ingrowth to create a seal and to promote a strong and durable attachment, although tissue ingrowth in the vicinity of the GEJ 106 is not expected to be robust. All or a portion of the fastener can be coated and/or made with a swellable material to create a seal and/or to spread out the force of attachment over a greater surface area, thereby reducing the pressure on the tissue. All or a portion of the fastener can be coated and/or made with a material that is biodegradable or bioresorbable. Examples of such coatings materials are described in the parent application Ser. No. 10/698,148.

One method for placing an implantable device within a patient's body has been described as a "parachuting" technique. In this technique, multiple elongated sutures extend from a plurality of implanted serosal anchors where the device is to be implanted with the ends of the sutures extending out of the patient's body. The ends of the sutures are passed through a sewing ring or similar structure on the device while the device is still outside of the patient's body, then the cuff is parachuted or slid into place along the sutures. The cuff is typically secured in place by knotting the elongated sutures with the help of a knot pusher or similar device and then the sutures are cut off close to the knots. U.S. provisional patent application 60/534,056 describes a variation of this method for implanting a device within a patient's digestive tract using T-tag fasteners. Alternatively, suture locks such as those described in U.S. Pat. No. 4,235,238, the disclosure of which is hereby incorporated in its entirety by reference herein, or those used in the BARD Endocinch system can be used to secure the suture prior to cutting.

When parachuted into place along the sutures, the cuff may be folded or compressed to pass through the esophagus or through a delivery tube placed in the esophagus. When using this parachuting technique it is desirable to minimize the friction between the device and the sutures. This can be done by using a low friction material or a low friction coating on the sutures and/or the device. This is also done by dimensioning and/or orienting structures, e.g. holes, to guide the parachuted device to reduce friction.

Figure 12:
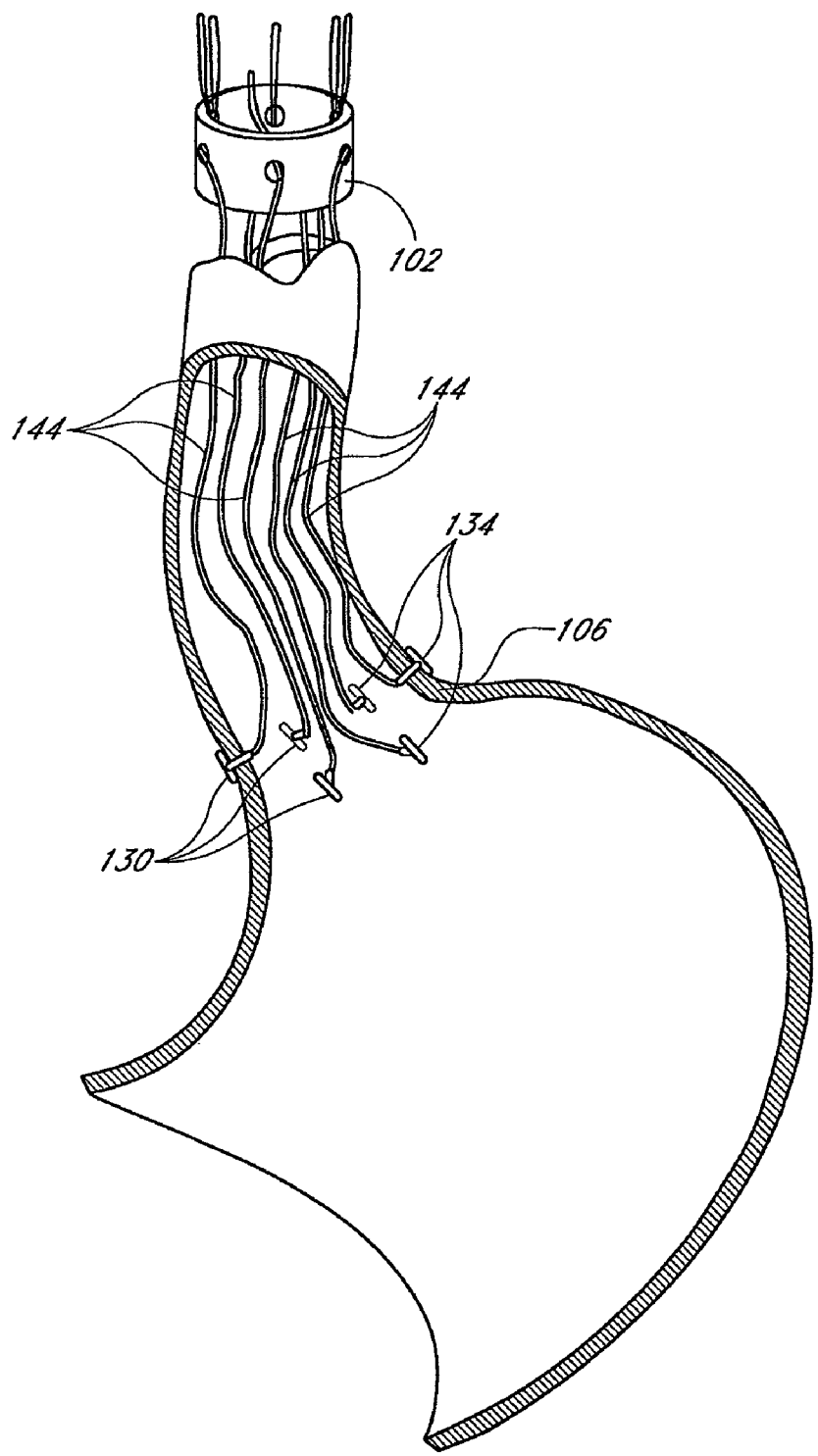
FIG. 12 shows a cuff being parachuted into place along a plurality of suture tails.

FIG. 12 shows an implantable device 102 being implanted at the GEJ 106 using a parachuting technique. One method of using a fastener delivery device for placement of an implantable device 102 by the parachuting technique is disclosed in U.S. utility patent application Ser. No. 11/025,364, previously incorporated by reference herein.

Alternatively, the device 102 may be partially parachuted into place, meaning that 2-4 parachute sutures are used to slide the device 102 into position with the proper orientation. Then additional fasteners, for example T-tag fasteners, are delivered endoscopically to complete the attachment of the device 120 to the tissue.

If suture tails are delivered through a closed lumen (e.g. in or attached to an endoscope), the lumen must be removed from around the suture tails before a device can be parachuted over the sutures if the device is too large to pass through the lumen. This can present a challenge related to maintaining the organization of the suture tails and preventing confusion, crossing, winding and/or tangling of the suture tails. If T-tag fasteners and their suture tails are passed externally e.g. through an external lumen with a longitudinal slot or in a non-enclosed rail type system, the suture tails can be managed external to the lumen used to place the T-tag fasteners and external to the scope. This facilitates manipulation of the scope, simplifies scope exchanges and simplifies suture tail management.

Suture tail management external to the scope or an enclosed lumen can be combined with suture holders external to the patient, similar to those used for parachuting replacement heart valves into place. Snugging the sutures as described above is simpler when the suture tails are external to the scope, as is avoidance of crossing, winding and/or tangling of the suture tails. Suture holders, such as slots, clamps or clips, can be combined with a mouth guard for organizing the sutures during a peroral parachuting procedure.

One aspect of suture tail management is that it must happen from one end of the system to the other. Therefore, the method and apparatus must address this issue. For example, after placement of a T-tag fastener, a slight tension on the suture tail can hold the suture against the wall of the lumen or in a straight position where it is less likely to tangle. Apparatus can include means to maintain tension while allowing scope movement and manipulation, e.g. tension from a long soft spring, an elastic band or a spring-loaded reel.

Sometimes, when performing an endoscopic procedure, an overtube is used to line the esophagus and protect it from damage due to insertion and manipulation of the endoscope and related tools and devices. Other practitioners prefer to avoid the use of an overtube. In either case, it may be desirable to secure an implant being parachuted down the esophagus in a collapsed, folded or otherwise reduced configuration. A major issue when parachuting a device into place is friction between the device and the sutures, and collapsing or folding the device may exacerbate the problems with friction.

Overtube

Overtubes are currently used in endoscopic procedures to protect the esophagus during the procedure. For example, overtubes can be used in the delivery of the cuffs and gastrointestinal sleeves described herein. One example of an overtube 600 disclosed in aspects of the present invention is shown in FIGS. 29A-29B. FIG. 29A shows an end view of overtube 600, and FIG. 29B shows a side view of overtube 600. It is generally clinically desirable for overtube 600 to have certain properties.

Overtube 600 is designed to be atraumatic such that it can be placed into the esophagus without damaging the walls of the esophagus. In particular the distal rim of the tube should be designed with a rounded rim so there are no sharp edges that can catch on any structure. The distal end of the tip could also have a portion that is softer than the rest of the tube and could be of a different material, like a foam or soft rubber. The internal surface of the overtube should have as low a coefficient of friction vis-à-vis the devices that will be passed through the tube as practical. This can be optimized through various coatings as would be understood by those skilled in the art. Likewise, the outside diameter should have a low coefficient of friction vis-à-vis the tissue surface it will appose. The desired coefficient of friction can be obtained with the appropriate surface coatings or by selection of appropriate materials for forming the overtube, as would be understood by those skilled in the art. A variety of materials could be used for the main overtube body, including but not limited to PVC, PTFE, PFA, TPE, polyethylene, silicone, polyurethane, nylon, carbothane, and other elastomeric or thermoplastic materials. In preferred embodiments overtubes are clear so that physicians can visualize the anatomical structures external to the overtube.

Overtube 600 should also have sufficient structural integrity to resist kinking or collapsing of their lumens or excessive movement that could damage their lumens. Structural reinforcement could be provided by integrating a spiral metal or plastic element along the length of overtube 600. Linear, flat, or round metal or plastic elements could also be integrated along the length of an overtube depending on the desired clinical outcome. These elements can also provide flexibility which allows the overtube to follow the natural curvature of the mouth and esophagus. Any combination of these elements that provide the desired stiffness could be used as well.

Distal Cuff Mounting

In some embodiments, cuff 102 is held at distal end 626 of overtube 600 such that cuff 102 does not need to be parachuted down the length of overtube 600 after anchors 604 are placed. See, e.g., FIG. 31B. In these embodiments, suture 608 can be threaded through grommets 640 on cuff 102 in different ways. For example, suture 608 can be pre-threaded through cuff 102 before deployment of overtube 600, or anchors 604 can be deployed through grommets 640 and the tissue of the GEJ 106 at approximately the same time, or anchors 604 can be deployed at the GEJ 106 and then a suture capture device (not shown) can be placed through each grommet 640 to capture a portion of suture 608 and pull it through grommet 640 from the outside diameter to the inside diameter of cuff 102.

In some embodiments in which cuff 102 is pre-threaded and held at distal end 626 of overtube 600, it may be desirable to incorporate certain features that will minimize any friction between cuff 102 and sutures 608 running from grommets 640 proximally along the length of overtube 600 and any risk of interference between cuff 102 and devices in lumen 624 of overtube 600 For example, a recess can be formed in wall of overtube 600 where cuff 102 can be placed such that the outer surface of cuff 102 will be continuous with the outer surface of overtube 600. Or, a recess can be formed within wall 636 of overtube 600 for cuff 102 placement in this location. The recess can be formed by extrusion, by forming wall 636 of overtube 600 by laminating layers of material together and leaving some layers out from the area forming the recess, or by any other method as would be contemplated by those skilled in the art.

In some embodiments, cuff 102 is held in place during overtube 600 placement with cuff holding elements 928. These elements can engage cuff 102 at its proximal rim, at its distal rim, at any location between the proximal rim and the distal rim, or at any combination of these locations. These elements can comprise hooks, sutures, adhesives, or any other means of holding cuff 102 in place on overtube 600 as would be contemplated by those of skill in the art. The elements can be released from cuff 102 using various means as would be understood by those skilled in the art. For example, manual manipulation can be used to pull out sutures or straighten or retract hooks. In another example, adhesive elements can be flushed with a solution or liquid that weakens the adhesive bond between the elements and cuff 102.

Atraumatic Delivery of Overtube

In some embodiments, to reduce the risk of perforating the esophagus when deploying overtube 600 into the esophagus, an atraumatic dilator 800, as shown in FIGS. 49A-49B may be used. The proximal end 804 of dilator 800 is placed into lumen 624 at the distal end 626 of overtube 600. The distal portion 808 of dilator 800 is tapered to ease insertion of overtube 600, decreasing in circumference from a location 812 distal to the proximal end 804 until distal tip 816. At its proximal end of the tapered distal tip 816, dilator 800 can have an outer diameter 2 to 4 mm smaller, for example, than the inner diameter of overtube 600. The nosecone, the tapered part of the dilator 800, can also include a super-flexible skirt (not shown) attached to nosecone extending proximally and gradually increasing in diameter to a diameter greater than the outer diameter of overtube 600. When dilator 800 extends proximally past the distal end 626 of overtube 600, the skirt resides over distal end 626 of overtube 600 and cuff 102 to protect the esophagus and cuff 102 upon insertion of overtube 600. After overtube 600 has been deployed, dilator 800 is removed through lumen 624 of overtube 600; the gap between the outer diameter of dilator 800 and the inner diameter of overtube 600 is sufficiently large to allow dilator 800 with the skirt to be pulled back through overtube 600. Deployment of dilator 800 down the esophagus can be aided by cannulating dilator 800 over a guidewire 912. FIG. 49A is a side view of dilator 800. FIG. 49B is a front view of dilator 800.

In some embodiments, to reduce the risk of perforating the esophagus when deploying overtube 600 into the esophagus, endoscope 448 instead of dilator 800 can be used as an inserter. For example, distal end 626 of overtube 600 can incorporate a flexible shroud (not shown) that minimizes gaps between the outer diameter of endoscope 448 and the inner diameter of overtube 600 to prevent tissue entrapment and perforation. The shroud may be a separate component or attached to overtube 600 or endoscope 448 and can comprise elastomeric or flexible materials. The shroud may also comprise a rounded tip at the distal end of endoscope 448 with an inner diameter close to the outer diameter of endoscope 448.

Other devices for achieving atraumatic delivery of overtube 600 into the esophagus are contemplated per aspects of the present invention. For example, distal elements or tips (not shown) can be placed at distal end 626 of overtube 600. After deployment of overtube 600, the tips can be removed through lumen 624 or, if the tips comprise easily digestable materials, they can be detached from overtube 600 and allowed to drop into the stomach. The tips can have outer diameters approximately equal to, slightly larger than, or slightly smaller than the outer diameter of overtube 600. The tip and overtube 600 are advanced together. For example, the tip can be advanced by pushing on overtube 600. Or, the tip can be pushed by a pusher rod (not shown) thereby pulling overtube 600 into place because the tip is attached to distal end 626 of overtube 600. Less column stiffness is required for overtube 600 in the latter embodiment than in the former embodiment in which the tip is advanced by pushing overtube 600. In various embodiments, the tip can be configured as desired to achieve particular clinical outcomes including atraumatic delivery of overtube 600. For example, the tip can be conical, hemispherical, or hemi-elliptical. Ideally, the tip is configured such that it comprises no sharp projections or other elements on its surface that could catch or damage any internal tissue as overtube 600 is deployed. The tip can also be pre-coated with a lubricious substance or coated with a lubricious substance immediately prior to overtube 600 deployment. Examples of lubricious substances include K-Y jelly or any of a variety of hydrophilic gels known in the art. The patient can also ingest a substance that either coats the esophagus or stimulates production of mucus which will prevent drying out of the esophagus, to aid in deployment of overtube 600. Cuff Deployment and Suture Management In some embodiments, as shown in FIGS. 30A-30B, anchors 604 for mounting the cuff 102 are threaded onto sutures 604 which traverse at least part of the length of overtube 600. For example, sutures 608 can comprise a tail end 612 and an anchor end 616. In some embodiments, tail end 612 and anchor end 616 can be accessed at the proximal end 620 of overtube 600 and are mobile in the directions approximately parallel to the longitudinal axis of overtube 600 such that additional suture can be taken up by pulling on either tail end 612 or anchor end 616 if desired. While mounting cuff 102, portions of sutures 608 including tail ends 612 and anchor ends 616 may be in close proximity within the lumen 624 of overtube 600 or extend past proximal end 620. Without adequate suture control, sutures 608 could knot or interfere with each other or with the devices, such as an endoscope, that are placed through lumen 624 of overtube 600. Thus, in preferred embodiments, overtube 600 incorporates one or more features that facilitate suture management. These features are incorporated along at least part of the length of overtube 600.

In some preferred embodiments, overtube 600 includes two channels 628 and 632 within its wall 636 per suture 608 and per anchor 604. In one preferred embodiment, as shown in FIGS. 29A-29B, there are twenty-four suture management channels total, twelve channels 628 and twelve channels 632, for deploying twelve anchors 604 at the GEJ 106. Channels 628 and 632 pass from the proximal end 620 to the distal end 626 of overtube 600. Tail end 612 passes through channel 628 and anchor end 616 passes through channel 632 such that both ends extend from proximal end 620 of overtube 600 and can be manipulated by an operator. The length of suture 608 between tail end 612 and anchor end 616 at the distal end 626 of overtube 600 can be pre-threaded through a distal mounted cuff 102 or make a direct bend between channels 628 and 632.

In one embodiment shown in FIGS. 31-40, in which suture 608 is pre-threaded through cuff 102, suture 608, starting from tail end 612, is passed through channel 628 from proximal end 620 of overtube 600 to distal end 626 of overtube 600. At distal end 626 of overtube 600, suture 608 emerges from channel 628, passes through grommet 640 on cuff 102 from the inner surface to the outer surface of cuff 102, passes along the outer surface of cuff 102 and to distal end 626 of overtube 600 and then enters channel 632 from which anchor end 616 exits at proximal end 620 of overtube 600. Anchor 604 is then threaded onto anchor end 616. In this embodiment, tail end 612 and anchor 616 are both releasable from channels 628 and 632, respectively, when sufficient force is applied to suture 608.

As shown in FIGS. 31A-31E, overtube assembly 900, comprising overtube 600, cuff 102, sutures 608, anchors 604, cuff tethers 928, and biteblock 904, is deployed down the esophagus towards the GEJ 106 over a guidewire 912, using a dilator 800 inserted at the distal end 626 of overtube 600. Cuff tethers 928 attach cuff 102 to overtube 600. FIG. 31A is a side view of overtube assembly 900. FIG. 31B is a front perspective view of overtube assembly 900, and FIG. 31C is a front perspective view of overtube assembly 900 showing the distal end of assembly 900 in greater detail. FIG. 31D is a back view of overtube assembly 900 in which biteblock 904, sutures 608, and anchors 604 are visible. FIG. 31E is a front view of overtube assembly 900 in which biteblock 904, dilator 800, overtube 600, sutures 608, and cuff 102 are visible.

After overtube assembly 900 is deployed down the esophagus to the GEJ 106, dilator 800 is removed as shown in FIGS. 32A-32C. FIG. 32A is a side view of overtube assembly 900 after dilator 800 and guidewire 912 are removed. FIG. 32B is a front perspective view of overtube assembly 900 after dilator 800 and guidewire 912 are removed, and FIG. 32C is an enlarged view of the distal end of overtube assembly 900 after removal of dilator 800 and guidewire 912.

FIGS. 33A-33C show the insertion of endoscope 448 through overtube 600 after dilator 800 and guidewire 912 have been removed. Insertion of endoscope 448 enables overtube assembly 900 to be deployed at a desired location near the GEJ 106. FIG. 33A shows a front perspective view of endoscope 448 passing through the lumen of overtube 600 from its proximal end and emerging from the distal end of overtube 600. FIG. 33B is an enlarged view of the distal end of overtube assembly 900 with endoscope 448 emerging from the distal end of overtube 600. In some embodiments, as shown in FIG. 33C, hooks 920, rather than tethers 928, are placed around the circumference of the distal end of cuff 102 and engage the distal end of overtube 600 such that cuff 102 is retained at the distal end of overtube 600. Hooks 920 can also be used to mount sleeve 100 (not shown).

After overtube assembly 900 has been deployed, endoscope 448 is removed from overtube 600, anchor inserter 652 is passed through the lumen of endoscope 448, and anchor 604 on anchor end 616 is loaded into an anchor inserter 652, as shown in FIGS. 34A-34D. Sutures 608 should be sufficiently long to prevent tail ends 612 from being pulled into channels 628 during the procedure such that they are not emerging from channel 628. FIG. 34A shows anchor inserter 652 passed through the lumen of endoscope 448 at the proximal end of overtube assembly 900 with an anchor 604 loaded. FIG. 34B is an enlarged view of the distal end of overtube assembly, including cuff 102 and sutures 608. FIG. 34C is an enlarged view of the proximal end of overtube assembly 900 and the distal end of anchor inserter 652 within the lumen of endoscope 448 with anchor 604 loaded. FIG. 34D is a perspective back view of the distal end of anchor inserter 652 within endoscope 448 and with anchor 604 loaded and the proximal end of overtube assembly 900.

As shown in FIGS. 35A-35B, anchor inserter 652 within endoscope 448 is then advanced through lumen 624 of overtube 600 and the portion of suture 608 in channel 632 is released simultaneously by virtue of the advancing movement. As the portion of suture 608 is released from channel 632, its movement can be controlled by adjusting the tension on tail end 612. Anchor inserter 652 and endoscope 448 are then advanced to the GEJ 106 so that anchor 604 can be deployed. Endoscope 448 enables the operator to position anchor inserter 652 as desired. Additional suture 608 can be pulled out of channel 628 as anchor inserter 652 is advanced past distal end 626 of overtube 600. FIG. 35A is a front perspective view of overtube assembly 900 with endoscope 448 and anchor inserter 652 passed through overtube 600. FIG. 35B is a front perspective view of the distal end of overtube assembly 900 showing anchor inserter 652, cuff 102, sutures 608, and endoscope 448 in greater detail.

After anchor 604 is deployed at the GEJ 106, another anchor 604 is loaded into anchor inserter 652 and deployed following the same process. This process is repeated until all twelve anchors 604 are deployed at the GEJ 106, as shown in FIGS. 36A-36D. FIG. 36A shows overtube assembly 900 with anchor inserter 652 within endoscope 448 advanced to the GEJ 106 and twelve anchors 604 deployed. FIG. 36B is an enlarged view of the distal end of overtube assembly 900 with endoscope 448 and anchor inserter 652 passing through overtube 600 and twelve anchors 604 deployed at GEJ 106. FIG. 36C shows overtube assembly 900 and GEJ 106 with anchors 604 deployed through the inner surface to the outer surface of the GEJ 106. FIG. 36D is an enlarged view of the distal end of FIG. 36C showing GEJ 106 with anchors 604 deployed. Although the above process is discussed for the deployment of twelve anchors 604, it can be used to deploy different numbers of anchors 604, as desired to achieve a particular clinical outcome.

As shown in FIGS. 37A-37B, cuff tethers 928 are released after anchors 604 have been deployed such that cuff 102 is free to move along sutures 608. Tail ends 612 attached to each anchor 604 still reside in channels 628 and can be manipulated by the operator at the proximal end of overtube assembly 900. FIG. 37A is a front perspective view of overtube assembly 900 after cuff tethers 928 have been removed, and FIG. 37B is an enlarged view showing cuff 102 at the distal end of overtube 600 after cuff tethers 928 have been removed.

As shown in FIGS. 38A-38B, after cuff tethers 928 are released, anchor inserter 652 is removed and cuff 102 is parachuted down tail ends 612 of suture 608 towards GEJ 106 and placed such that deployed anchors 604 are aligned with grommets 640. FIG. 38A shows overtube assembly 900 with cuff 102 parachuted down to the GEJ 106 where anchors 604 are deployed. FIG. 38B is an enlarged view showing cuff 102 parachuted down to GEJ 106.

Figure 39F:
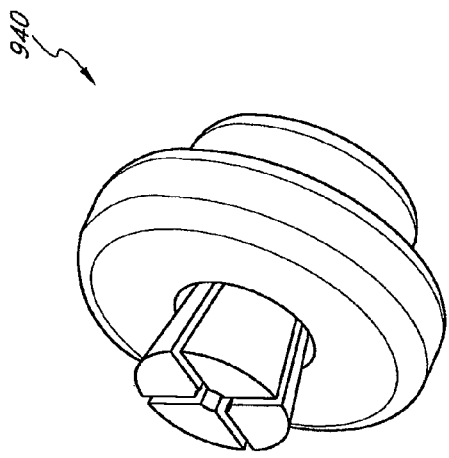
FIGS. 39D-39F show views of a suture lock.
Figure 39E:
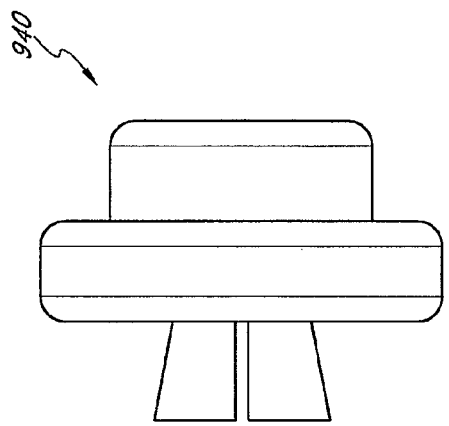
Figure 39D:
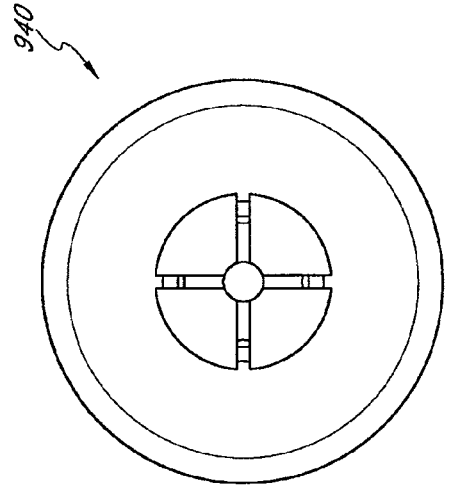
Figure 39G:
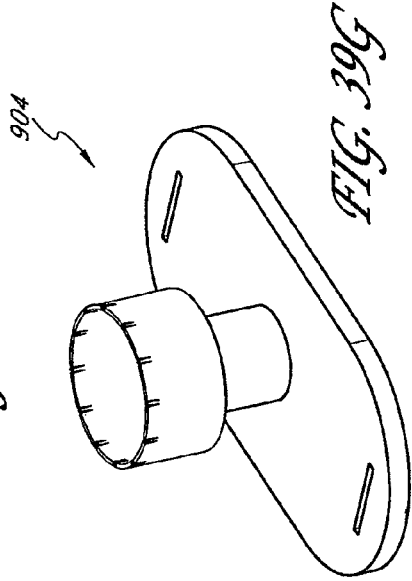
FIG. 39G shows a bite lock.

Cuff 102 is then locked into place, as shown in FIGS. 39A-39C. In some embodiments, suture lock devices 932 are threaded over each suture 608, passed distally towards grommets 640, and then used to lock each anchor 604 in place at the inner surface of cuff 102 at each grommet 640. As suture lock devices 932 are passed over sutures 608 towards grommets 640, sutures 608 are stripped out of channels 628. FIG. 39A is a front perspective view of overtube assembly 900 with one suture lock device 932 passed over a suture 608 approaching a grommet 640. FIG. 39B is an enlarged view showing the distal end of overtube 600 with sutures 608 extending distally out of channels 628, anchors 604 at anchor ends 616 of each suture 608, and a suture lock device 932 on one suture 608. FIG. 39C is a front view of overtube assembly 900 showing one suture lock device 932 on one suture 608 which has been stripped out of channel 628. FIGS. 39D-39F show a collet lock 940, discussed below. FIG. 39G shows biteblock 904.

Figure 40E:
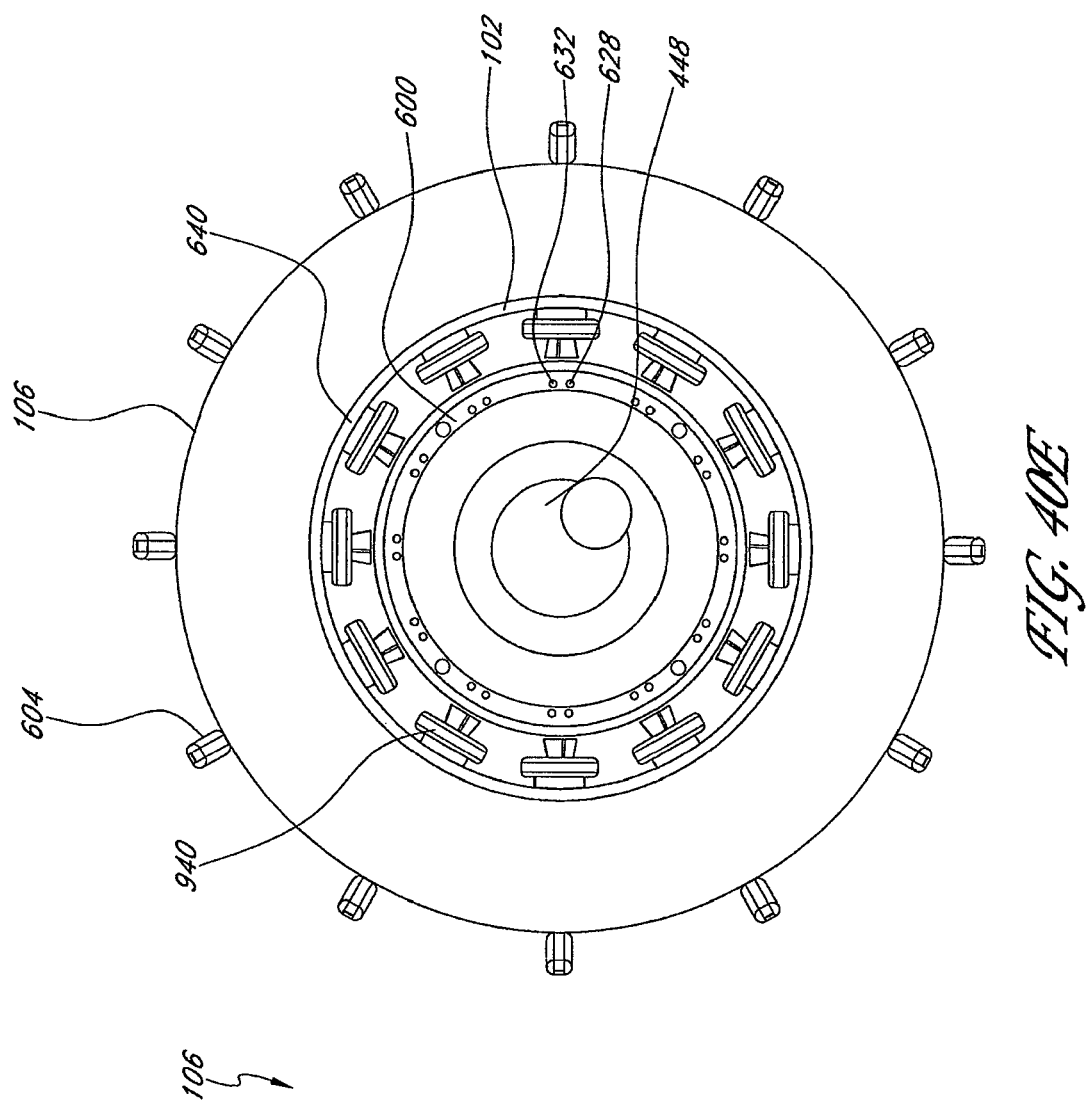
FIG. 40E is a front end view of an overtube assembly showing anchors deployed at the GEJ.

FIGS. 40A-40E show cuff 102 attached at the GEJ 106 after each anchor 604 has been locked into place. FIG. 40A is a front perspective view of overtube assembly 900 with anchors 604 and cuff 102 deployed at the GEJ 106 and locked into place with locks 940. FIG. 40B is an enlarged view showing anchors 604 and cuff 102 deployed at the GEJ 106 and collet locks 940 at grommets 640 holding anchors 604 in place. FIG. 40C is a front perspective view of overtube assembly 900 and the GEJ 106 with cuff 102 and anchors 604 deployed. FIG. 40D is an enlarged view showing locks 940 against the inner surface of cuff 102 at grommets 640 holding anchors 604 in place. FIG. 40E is a front view of overtube assembly 900 showing anchors 604 deployed at the GEJ 106 through grommets 640 in cuff 102 and locked into place with locks 940.

When cuff 102 is pre-threaded it can reside anywhere along the length of overtube 600. Cuff 102 can also reside outside the patient and proximal to overtube 600 where it is threaded and parachuted down overtube 600 to the GEJ 106.

Overtube Channels

Figure 43:
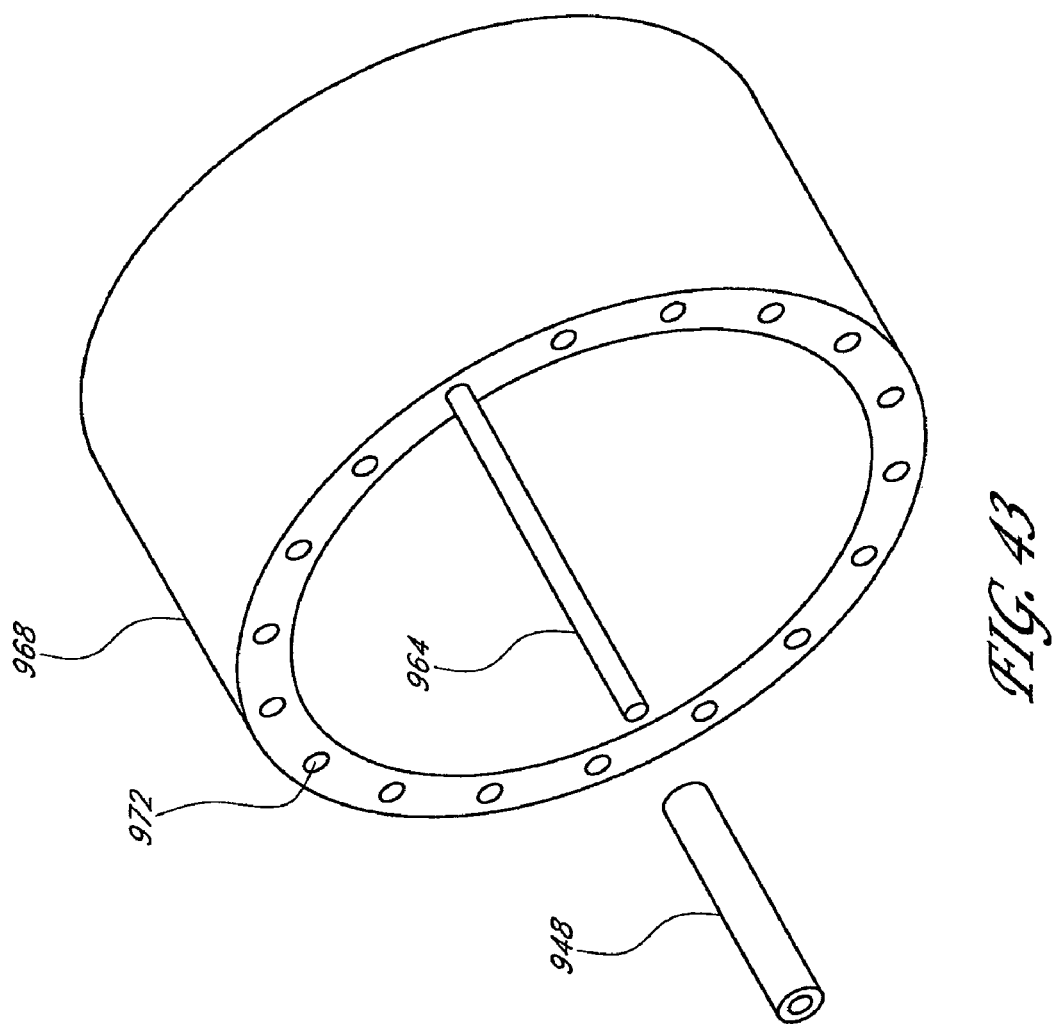
FIG. 43 is a perspective view of an end mandrel for positioning a plurality of tubes.

Various embodiments of channels 628 and 632 are disclosed per aspects of the present invention that allow tail end 612 and anchor end 616 to be releasable from the channels when sufficient force is applied to suture 608. In some embodiments, channels 628 and 632 comprise thin-walled capillary tubes 948, as shown in FIGS. 42A-42D, that are attached between the inner surface 952 and outer surface 956 of overtube 600. In these embodiments, wires 960 can be attached between capillary tubes 948 forming channels 628 and 632 from the proximal to distal end of overtube 600 to reinforce overtube 600 and prevent kinking. Wires 960 can comprise stainless steel and/or any other reinforcing materials as would be understood by those skilled in the art. FIG. 42A is an enlarged view of the distal end of FIG. 42B showing capillary tubes 948 and wires 960. FIG. 42B is a front perspective view of overtube 600 with capillary tubes 948 and wires 960 between inner surface 952 and outer surface 956 and end mandrel 968 at the proximal end 620 of overtube. FIG. 42C is a front view of overtube 600 with capillary tubes 948 forming channels 628 and 632 between inner surface 952 and outer surface 956 and wires 960 between channels 628 and 632. Capillary tubes 948 can be formed of PTFE or polyimide or any other materials that would be contemplated by those skilled in the art. FIG. 42D shows a capillary tube 948 comprising 28gauge PTFE. Tubes 948 are held straight while they are attached between the inner surface 952 and outer surface 956 of overtube 600 by a variety of means including adhesives, sutures, tape, end mandrels (as described below) or clamps. In some embodiments, inner surface 952 and outer surface 956 of overtube 600 can be formed by heatshrinking materials such as polyethylene. Inner surface 952 can be formed by heatshrinking material over an inner mandrel. As shown in FIG. 43, an end mandrel 968 comprising wire holders 972 can be placed around and at one end of inner surface 952. Wires 964 are then inserted into wire holders 972 and tubes 948 are placed over wires 964. Tubes 948 can then be bonded to inner surface 952 using adhesive, heat, and/or any other means as would be contemplated by those skilled in the art. Wires 960 for reinforcement can then be inserted between channels 628 and 632 formed by tubes 948. Outer surface 956 can then be formed by heatshrinking material over the assembly of inner surface 952, tubes 948, and wires 960. Tubes 948 can be slit as desired for facilitating releasability of sutures 608.

Figure 45:
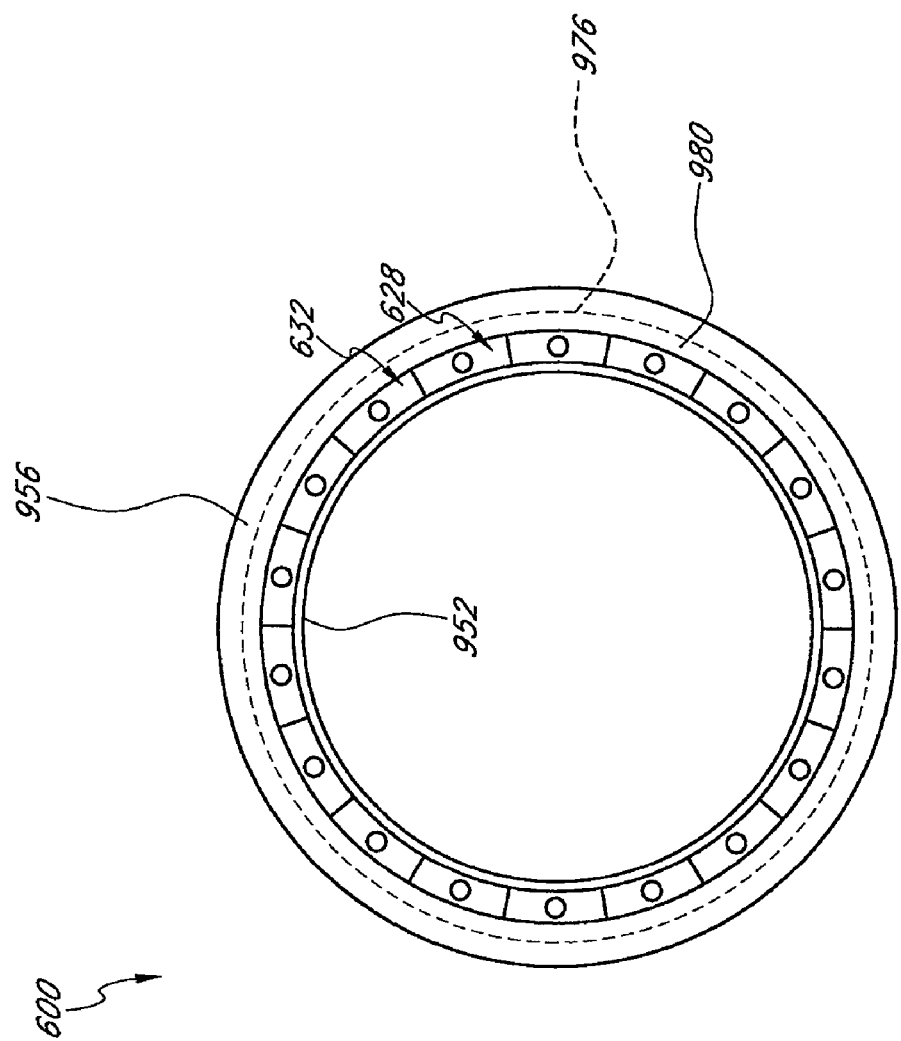
FIG. 45 is an end view of one embodiment of an overtube.
Figure 46A:
FIGS. 46A-46F schematically illustrate channel configurations for releasably retaining sutures.
Figure 46B:
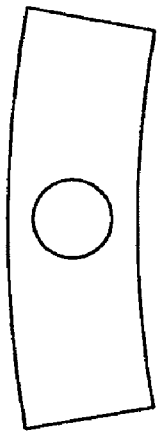
Figure 46C:
Figure 46D:
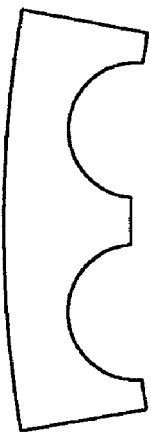
Figure 46E:
Figure 46F:
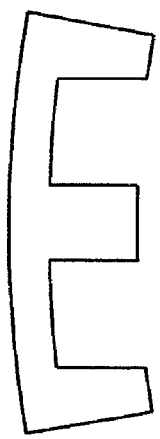

In other embodiments, channels 628 and 632 can be extruded and assembled together with inner surface 952, coil or braid reinforcement 976, middle tubing 980, and outer surface 956 to form overtube 600, as shown in FIG. 45. In one example, as shown in FIG. 44A, inner surface 952 can be formed as tubing by heatshrinking material over a mandrel. One embodiment of an extruded channel 628 or 632 is shown in FIG. 44B. FIG. 44C shows coil reinforcement 976, and FIG. 44D shows outer surface 956. Outer surface 956 can also be formed as tubing by heatshrinking material over the underlying assembly comprising inner surface 952, channels 628 and 632, middle tubing 980, and reinforcement 976. Inner surface 952 and outer surface 956 can also be formed as sheaths or coatings or by any other means as would be understood by those skilled in the art. FIG. 45 shows one embodiment of an assembled overtube 600. Inner surface 952 is formed as tubing by heatshrinking over a mandrel. Extruded channels 628 and 632 can then be held around the outer circumference of inner surface 952 by a thermal bond, adhesive, and/or any other means as would understood by those skilled in the art. Then middle tubing 980 can be heatshrunk over channels 628 and 632 thereby setting them in place. Coil reinforcement 976 is then assembled over middle tubing 980, and outer surface 956 is formed as tubing by heatshrinking or dip-coating material over coil 976.

Extruded channels 628 and 632 can be shaped like tubes running from proximal end 620 to distal end 626 of overtube 600, as shown in FIG. 44B. Other configurations of extruded channels 628 and 632 are shown in FIGS. 46A-46F. Slits can be formed in channels 628 and 632 with each slit facing lumen 624 of overtube 600 and running in a direction parallel to the longitudinal axis of overtube 600 from proximal end 620 to distal end 626 of overtube 600. Suture 608 is releasable through the slits when sufficient tension is applied. Alternatively, channels 628 and 632 can be formed of a material that will rip to allow release of suture 608 when sufficient tension is applied when the channel is designed close enough to the lumen 624.

In other embodiments, channels 628 and 632 can comprise a variety of configurations that will releasably trap suture 608. For example, channels 628 and 632 can comprise S-shaped locking slots 984 or L-shaped locking slots 988 formed in wall 636 of overtube 600 as shown in FIGS. 47A-47B. Suture 608 will be held at the end 982 of an S-shaped slot 984 closer to outer surface 956 of overtube 600 until it is pulled around both curves of the S-shaped slot 984 to the end 985 opening into lumen 624 of overtube 600. Suture 608 will also be held in the leg 983 of an L-shaped slot 988 closer to outer surface 956 of overtube 600 until it is pulled to the corner where the other leg 987 starts so that it can be released into lumen 624.

In another embodiment, slots or ribs 992 are formed in the wall 636 of overtube 600 that are non-releasably sealed off from outer surface 956 of overtube 600 but open to the inner surface 952 of overtube 600, as shown in FIG. 48. Another tube 996 is placed within overtube 600. Tube 996 has one slot 998 that traverses the wall of tube 996 such that it is open to ribs 992 and to lumen 624. Tube 996 can be rotated within overtube 600 such that slot 998 is aligned with one rib 992 in overtube 600 at a time such that suture 608 within the rib 992 is released.

In these embodiments, wall 636 of overtube 600 must have sufficient thickness to accommodate channels 628 and 632 and ribs 992 that will house suture 608.

In another embodiment, laminated sheets can be formed with separated channels 628 and 632 as part of overtube 600 or as a tube within overtube 600. This form of construction is very similar to corrugated cardboard with two essentially flat sheets on either side of a corrugated center. Once constructed the sheet can be rolled into a tube to form a lumen. To get the suture to release from the channel, any of the above methods could be used.

In yet another embodiment, laces that can be pulled out can be used to hold suture 608 against the inner surface 952 of wall 636 of overtube 600. In some embodiments, suture 608 can be taped, glued, or attached with some other adhesive or coating material, including painted-on glue or film such as Latex, to inner surface 952 of wall 636 of overtube 600. In these embodiments, suture 608 can be released when tensioned by pulling through or overcoming the strength of the adhesive or coating material.

In embodiments in which anchors 604 start out loaded at the distal end 626 of overtube 600 or there are multiple anchors 604 pre-loaded into a multi-fire device, only one portion of suture 608 with a length approximately equal to the length of overtube 600 may need to be controlled by manipulating tail end 612. See, e.g., FIGS. 30A-30B. Any of the suture management methods discussed herein can be used with these embodiments. Cuff 102 could be pre-threaded or anchors 604 could be placed through grommets 640 on cuff 102 at the same time that anchors 604 are deployed at the GEJ 106.

Proximal Cuff Holder

A proximal cuff holder (not shown) can also be employed to hold cuff 102 at proximal end 620 of overtube 600. The cuff holder can be integrated with collar of the biteblock 904 to hold cuff 102 and sutures 608 simultaneously.

Bite Block

A bite block 904 as shown in FIG. 39G may engage overtube 600 at its proximal end and thereby hold overtube 600 in place.

Proximal Suture Docking Collar

In some embodiments, a proximal suture docking means such as a collar may be used on proximal end 620 of overtube 600 to hold sutures 608 out of lumen 624 of overtube 600 and enable an operator to manage them when desired. The collar can comprise slits to hold sutures 608 or posts around which sutures 608 can be wrapped. The collar can also comprise any other means of holding each suture 608 as would be understood by those skilled in the art. The collar can be numbered, labeled, or coded at or around these means to distinguish each suture 608.

Cuff Deployment Devices

In some embodiments, cuff 102 is deployed at GEJ 106 before anchors 604 are deployed through grommets 640 on cuff 102. Deployment devices of various configurations can be used in these embodiments to deploy cuff 102 so that at least a portion of its outer surface is held in close proximity to or in contact with tissue at the GEJ 106. Deployment devices can, for example, be retractor-type devices that apply pressure to at least a portion of cuff 102 or expandable devices that can hold at least one point of cuff 102 against or near the tissue at the GEJ 106. Deployment devices can be integrated with or attached to overtube 600, attached to endoscope 448 or separate from overtube 600 or endoscope 448 such that they are placed through lumen 624. In some embodiments, deployment devices are stand-alone devices that are not used in conjunction with a deployed overtube 600.

In some embodiments, cuff 102 is deployed using a balloon expandable device (not shown). A collapsed cuff 102 is mounted on a collapsed balloon of the device and advanced through lumen 624 of overtube 600 until it reaches the GEJ 106. The balloon is then inflated to push cuff 102 against the tissue of the GEJ 106. The outer surface of cuff 102 can comprise an adhesive, for example, fibrin glue, PMMA, or others known in the art that can hold cuff 102 in place for a period of time at least sufficient to allow the balloon to be deflated and removed and anchors 604 to be deployed. Other means of holding cuff 102 in place against the GEJ 106 for a sufficient amount of time can be used, as would be contemplated by those skilled in the art including, for example, tiny barbs approximately the size of a hair that penetrate no further than the mucosal surface of the GEJ 106. The barbs can be formed of bioabsorbable materials such as PLLA or PLGA so that they will be rapidly absorbed by the tissue of the GEJ 106 after cuff 102 is anchored. The mucosal surface of the GEJ 106 sloughs off with its normal replacement cycle such that no lasting damage to the tissue will be incurred. While the cuff is temporarily held in place, anchors can be placed through the grommet holes of the cuff for a more lasting attachment. Alternatively, the balloon holds cuff 102 at the distal end only so that grommets 640 are still accessible when the balloon is inflated. It may be desirable for the balloon to comprise a hardened surface on the proximal curvature of its surface to minimize the risk of accidental deflation of the balloon by contact with anchor inserter 652. A double balloon can also be used with one balloon that inflates at the distal end of cuff 102 and another balloon that inflates at the proximal end of cuff 102 such that a center portion of the lumen of cuff 102 is unobstructed. In preferred embodiments, one or both balloons of the double balloon is shaped like a "life saver" with a lumen through its center through which anchor devices such as anchors 604 can be placed.

In some embodiments, cuff 102 is deployed using a mesh expandable device (not shown). Mesh expandable device can, for example, be self-expanding or expanded by inflation of a balloon placed within the lumen of the mesh device. Mesh expandable devices that are self-expanding may comprise, stainless steel wire or a super-elastic material such as nitinol. Mesh expandable devices can have a double balloon-type configuration as discussed above with an unobstructed central lumen through which anchor devices such as anchors 604 can be placed. Mesh expandable devices can be formed, for example, by wrapping and heat setting wires around a mandrel or by laser cutting cylindrical surfaces.

Figure 54:
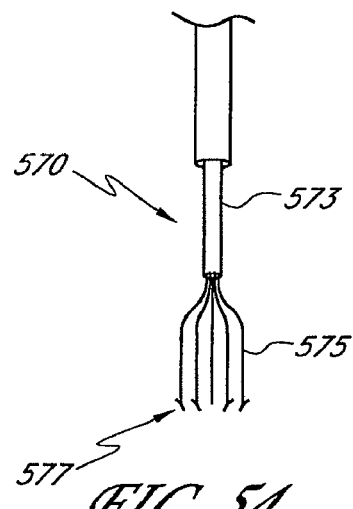
FIGS. 54-55D illustrate tools for holding a cuff in position at the GEJ during anchor deployment.

In some embodiments, wire basket deployment devices can be used to expand and hold cuff 102 in place during anchor 604 deployment. Referring to FIG. 54, there is illustrated a distal end of a cuff positioning tool 570. The tool comprises an elongate flexible body 573 having a proximal end and a distal end. The distal end of the flexible body 573 is provided with a plurality of preformed biasing elements 575 such as stainless steel or Nitinol wires, for positioning within cuff 102 and holding the cuff open against the adjacent tissue. At least three or four, and, preferably, at least eight or ten biasing elements 575 are provided. At least two and preferably all of the biasing elements 575 may be provided with a connector 577 for connection to the cuff 102. Connector 577 may comprise a barb, hook, clip, or other structure for engaging the cuff 102. The cuff positioning tool 570 may be delivered through a central lumen of a tubular sheath, to maintain the biasing elements 575 in a reduced cross sectional configuration for delivery and withdrawal from the patient. The connectors 577 may be detached from the cuff 102 in any of a variety of ways, depending upon the connector construction. For example, barbs or hooks may be mechanically forced apart from the cuff 102 by an endoscopically manipulated grasper or leverage tool. Alternatively, connectors 577 may be actively disengaged, such as by axially proximally or distally advancing a disengagement wire which extends axially through the flexible body 573 and manipulates the connector 577. Alternatively, a tubular sleeve may be concentrically carried by a flexible body 573 such that distal advance of the tubular sleeve forces the biasing elements 575 radially inwardly into a reduced cross sectional configuration, thereby separating connectors 577 from the cuff 102.

Figure 55A:
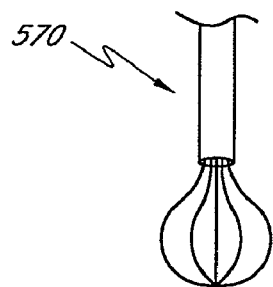
Figure 55B:
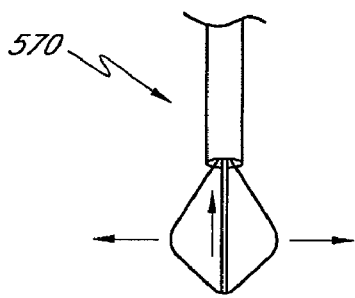

Cuff 102 can also be held in place with mechanically actuated expandable ribs or framing devices. These embodiments generally comprise rigid elements hinged at points such that when activated they expand outwards. One example of a framing device is a Malecot-type device that expands when a tensile force is applied to the tip of the device. Cuff 102 can be placed relative to the expandable ribs such that the ribs will not interfere with anchor 604 deployment through grommets 640. See, e.g., FIGS. 55A and 55B.

Figure 55C:
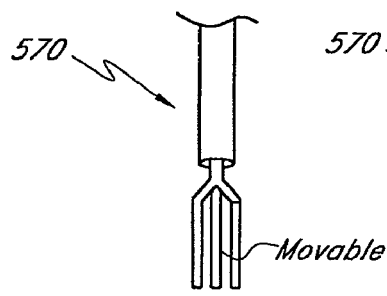
Figure 55D:
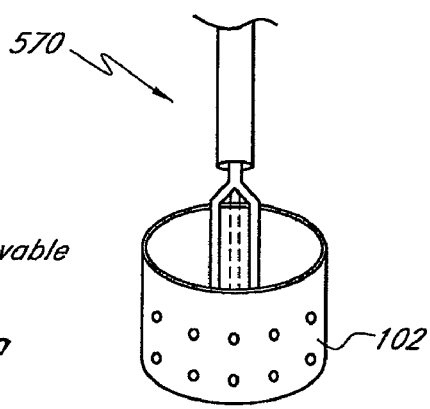

In yet another embodiment, cuff 102 can be held in place with a retractor-type device that is biased in an outward direction such that it can hold at least one portion of cuff 102 against or in close proximity to the tissue of the GEJ 106. The retractor-type device comprises a tong-type grasper that holds the inner and outer surfaces of a portion of cuff 102 simultaneously. Retractor-type device can hold one portion of cuff 102 during deployment of the first anchor 604. The device can then be loosened and slid around the circumference of cuff 102 to hold another portion of cuff 102 to deploy the next anchor 604. This process is repeated until all anchors 604 are deployed. See, e.g., FIGS. 55C and 55D.

Figure 52:
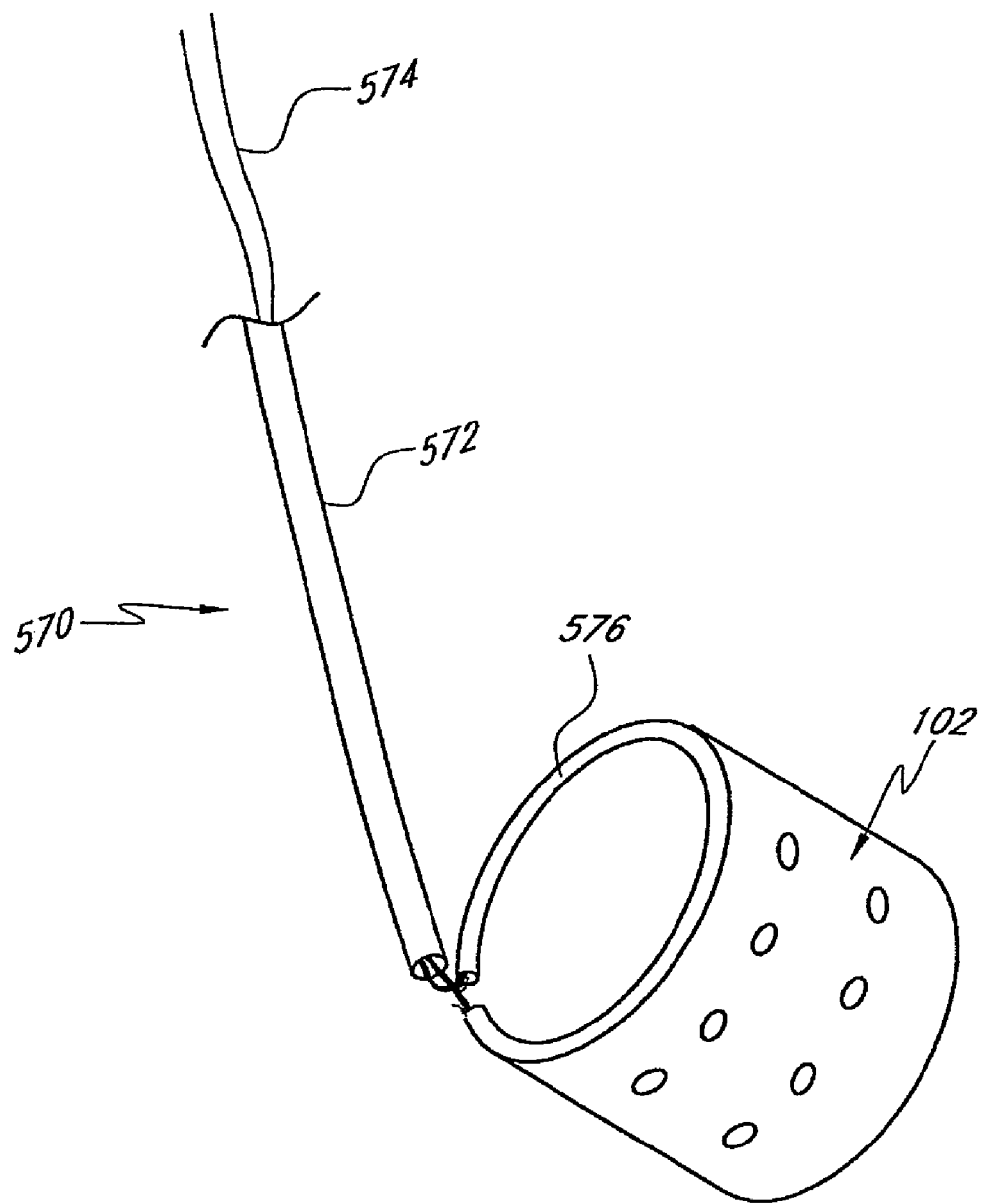
FIG. 52 illustrates a cuff management tool for manipulating the cuff during anchor installation.

In yet another embodiment, cuff 102 can be held in place with an expandable hoop ring, much like a snare, that has radial force. Referring to FIG. 52, there is schematically illustrated a cuff positioning tool 570 in association with a cuff 102. Although illustrated in connection with management of a cuff 102, the positioning tool 570 may alternatively be utilized to position the proximal end of a sleeve as will be apparent in view of the disclosure herein.

The cuff positioning tool 570 comprises an elongate flexible tubular body 572 having at least one central lumen extending axially therethrough. The central lumen axially movably receives at least one wire 574. The wire 574 extends through the tubular body 572 and through a path 576 within or attached to the cuff 102. For example, a proximal end of the cuff 102 may be rolled over onto itself to provide a lumen which extends circumferentially around the cuff. The wire 574 extends through the annular path 576 and is biased in a manner that holds the cuff 102 in an open configuration. The position of the cuff 102 may be manipulated by proximal or distal axial movement of the tool 570. Additional control may be achieved by providing a second tubular body 572 and corresponding second wire loop, such as spaced 180° apart from the first tool 570, to give additional control over cuff position.

As the snare's hoop is enlarged by the distal advancement of one end of the wire the proximal rim of the cuff 102 is expanded. Once expanded to the point where there is adequate contact with the desired area of the tissue wall, anchors 604 can be placed through the grommet holes of the cuff. After the anchors are deployed, one end of the snare wire can be released and by retracting the other end the snare can be pulled out of the proximal rim of the cuff leaving only the attached cuff 102 and anchors 604 in place. If more than one snare is used, a second or third snare can be prethreaded at other locations of the cuff to provide added assistance in opening up the cuff 102, spaced axially apart along the cuff much like hoops for a barrel. For example, another snare could be prethreaded through the distal rim of the cuff as well so there would be two mechanisms help bias the cuff into an open configuration for placement of anchors and to add more ability to advance and retract the cuff along the GI tract.

Cuff Design

In preferred embodiments, cuff 102 is configured as a compliant mesh cylinder with grommets 640 as mentioned above that reinforce anchor 604 attachments and prevent slippage of cuff 102 off of each anchor 604. Cuff 102 can comprise compliant and stretchable materials, for example, woven polyester velour material which is extremely compliant and stretches to a length approximately 200% of its unstretched length. Other compliant and stretchable materials for forming cuff 102 include Dacron, silicone, polyurethane, and other materials depending on the desired clinical outcome as would be contemplated by those skilled in the art. In preferred embodiments, cuff 102 is comprised of materials that are non-porous to undesired bacteria, sufficiently soft to minimize tissue irritation, biocompatible, corrosion-resistant to prevent degradation in a gastric environment, sufficiently strong to prevent detachment from anchors 604, and flexible and compliant.

A compliant cuff 102 accommodates typical motions of the esophagus and stomach such that any interaction between the tissue of the esophagus and the stomach and cuff 102 will not cause cuff 102 to be dislodged whereas interaction of the tissue with a rigid cuff might cause dislodging.

Grommets 640 have an inner diameter such that anchor inserter 652 or anchor 604 when in its collapsed configuration can pass through. The mucosal side attachment portions of anchors 604 have outer diameters sufficiently large to prevent them from passing through grommets 640.

Attachment locations of cuff 102 surrounding grommets 640 can be reinforced to prevent anchors 604 from ripping through grommets 640. Reinforcement means are oriented so as to allow cuff 102 to stretch.

In embodiments in which cuff 102 is deployed at the GEJ 106 before anchors 604 are deployed, cuff 102 may incorporate design features that facilitate deployment of anchors 604. For example, cuff 102 can comprise transparent or semi-transparent material that will facilitate visualization of the tissue near the target location. Grommets 640 can be configured as slots or as plus sign-shaped apertures to allow anchors 604 to be deployed at more than one orientation. Grommets 640 can also outnumber anchors 604 to facilitate deployment by providing multiple targets per anchor 604. Grommets 640 can also have an inner diameter larger the outer diameter of the tip of anchor inserter 652 so that there is more area within which the tip can move during deployment of anchors 604. Correspondingly larger suture locks, mucosal washers and/or serosal anchors 604 can be used so that they do not pass through the grommets 640 with larger inner diameters.

Figure 57:
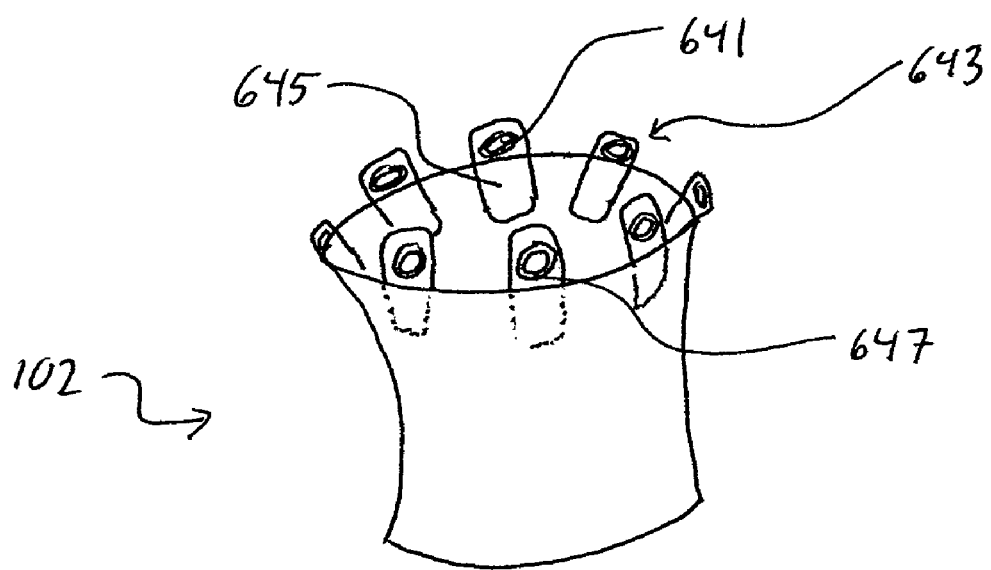
FIG. 57 is a schematic perspective view of a cuff in accordance with the present invention, having clear loops for improving visualization.

One example of an endoscopic cuff which has been modified to improve visualization of the attachment points and improve manipulation during deployment is illustrated in FIG. 57. Referring to FIG. 57, the cuff 102 includes a plurality of apertures 641 for receiving tissue anchors, as has been discussed. In the illustrated embodiment, each of the apertures 641 is displaced proximally from the cuff 102. Each aperture 641 is formed in a tab 643. The tab 643 additionally comprises an attachment zone, for attaching to the cuff 102. The attachment may be accomplished in any of a variety of ways, such as by stitching to the fabric of the cuff 102, adhesives, thermal bonding, or other techniques known in the art.

Each tab 643 comprises a material which is transparent to visible light, to facilitate endoscopic visualization therethrough. In one embodiment, the tab 643 comprises a transparent polyethylene terephthalate loop. In addition, the aperture 641 may be visually highlighted such as by outlining in a high contrast marking to enhance visualization.

Securing the Cuff

Cuff 102 can be secured against anchors 604 deployed near the GEJ 106 using suture locks instead of knots. The locks can be stand alone devices, part of the Washers described below, or part of cuff 102. The locks can be placed on cuff 102 after cuff 102 has been deployed near the GEJ 106. Alternatively, the locks can be used to help push cuff 102 down sutures 608 to deploy cuff 102 near the GEJ 106. In some embodiments, the locks can be delivered by a device that actuates the locks and cuts tail ends 612 of sutures 608 at the same time or separately.

In some embodiments, suture locks comprise sliding locks that are pushed down suture 608 like a knot and then activated. Sliding locks can be self-locking or may require the user to manually actuate the locking mechanism. In one example, the sliding locks are collett locks 940 as shown in FIGS. 39D-39F that have an interference fit with collars. Collett locks 940 are then slit and can be placed either on bites of suture 608 or slid over the ends of sutures 608. Collett locks 940 and collars fit together with a Morse taper. The collars are advanced to cuff 102. Then the collett locks 940 are advanced until they contact the collar and then collett locks 940 secure collars against cuff 102 before locking on suture 608. Tension is applied until the collett lock 940 compresses gripping suture 608. In another example, suture locks comprise side biting locks that do not need to be advanced over suture 608. The locks can, for example, use the following methods to hold suture 608: crimping of one deformable piece, interference fit between two pieces, heat or energy welding of two pieces, heat or energy welding of the lock to suture 608, and adhesives. Any other methods as would be understood by those skilled in the art can be used to aid the locks in holding suture 608.

In some embodiments, washers are placed between a suture lock or knot and cuff 102. This allows a smaller lock to be used because washer will prevent it from migrating through grommet 640 into cuff 102. Because washers are larger in diameter than the locks or knots, they can help to distribute any pressure from the locks or knots over a larger area thus reducing the risk of incurring pressure necrosis. Washers can also be configured so as to aid in tension control. Washers that aid in tension control can comprise spring or dampening elements. These washers can be configured as, for example, plunger-shaped washers, split ring spring washers, or double leaf spring shaped washers with an almond-shaped profile. Other configurations of washers may also aid in tension control as would be understood by those skilled in the art.

Figure 53A:
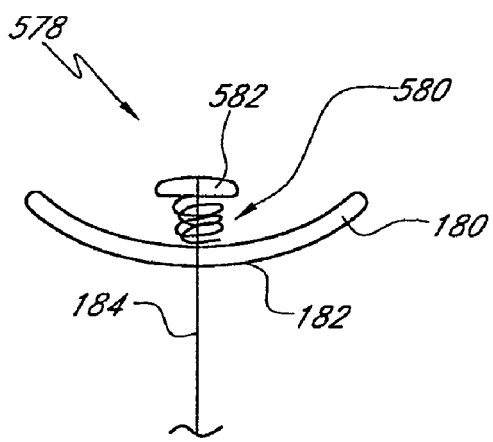
FIGS. 53A-53D show different tension management systems for tensioning suture anchors.

A variety of dampening or tension control systems is illustrated in FIGS. 53A through 53D. Referring to FIG. 53A, a tension control system 578 comprises a retention element 180 having a retention surface 182 for positioning against the serosal surface. A retention element 180 may be in the form of a T-tag, disc, or any of a variety of tissue anchors previously disclosed herein. A tension element 184, such a suture, is attached to the retention element 180 using a biasing element 580. The biasing element 580 enables the tension element 184 to be pulled away from the retention element 180, and, following removal of transient pulling forces, retract the tension element 184 back to its original resting configuration. In the illustrated embodiment, biasing element 580 is in the form of a spring such as a coil spring. A first end of the coil spring is in contact with the retention element 180, and a second end of the spring is linked to the tension element 184 such as through the use of a disc or button 582. The desirability of a separate disc or button 582 will depend upon the construction materials and other design criteria for the tension control system 578, and may not be necessary for all designs.

Figure 53B:
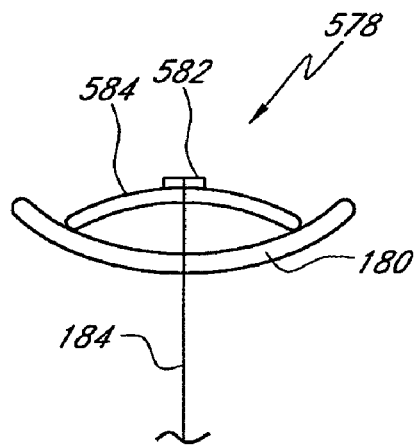

Referring to FIG. 53B, the tension control system 578 comprises a concave leaf spring like element 584. Traction on tension element 184 will decrease the distance along the axis of the tension element 184 between element 584 and the retention element 180. The resilience of the construction materials for the tension control system 578 urges the tension element back to its resting configuration.

Figure 53C:
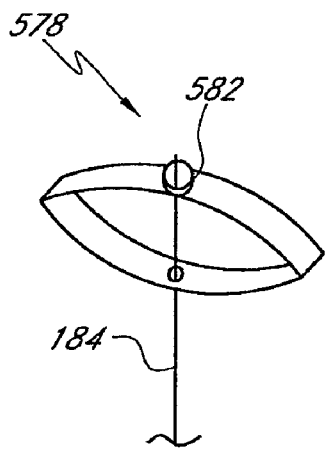

A further leaf spring type tension control system 578 is illustrated in FIG. 53C. A first and a second leaf springs, each formed in a concave configuration and positioned with the concavities facing each other may be compressed by tension on tension element 184 and expanded under the resilience of the leaf springs as will be understood by those of skill in the art.

Figure 53D:
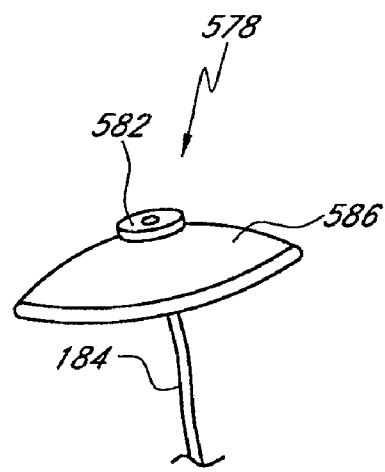

A further implementation of a tension control system 578 is illustrated in FIG. 53D. In this implementation, a flexible disc such as silicone or other biocompatible resilient material 586 is configured to have a concave surface positioned adjacent the serosal tissue. Tension on the tension element 184 pulls the center of the disc 586 towards the serosal surface, and the resilience of the disc 586 urges the tension element 184 back to its original configuration. Concave washer or disc configurations such as illustrated in FIG. 53D, if made from materials such as silicone, may require the use of a force distributing feature such as disc 582 as will be understood in the art.

Detecting Detachment or Failure of the Sleeve/Cuff System

Various methods are contemplated for detecting detachment and/or other failures of the sleeve/cuff system. In some embodiments, an external sensor can be used intermittently or worn at all times on a patient to monitor the position of magnet(s) positioned at the proximal and/or distal ends of sleeve 100 and/or cuff 102. Thus, if the sleeve 100 or cuff 102 moves to a location which would indicate that the system is in failure, the magnet(s) would move with the system which can be detected by the patient and/or physician. Magnet(s) can also be positioned on the distal end of sleeve 100 to monitor its position. If, for example, the distal end of sleeve 100 travels back up into the stomach area or in some other undesirable way, sensors could detect this movement and alert the patient and/or physician. In some embodiments, magnets can be positioned along the entire length of sleeve 100 and cuff 102 such that sensors can monitor all these positions. In an alternative embodiment, the magnet markers could just be markers with a magnetic signature, e.g any ferrous metal, and the magnets could be in the external sensor and would detect the movement of the markers with a magnetic signature. In some embodiments, radiopaque markers can be used to detect the positions of sleeve 100, cuff 102, and any other parts of the deployed system, using imaging or sensing techniques. In another embodiment, a capsule is tethered between sleeve 100 and cuff 102 when sleeve 100 and cuff 102 are attached. When the distance between sleeve 100 and cuff 102 exceeds a particular distance the capsule is actuated to alert patients. For example, the capsule can snap and release dye or some other indicator that manifests itself in patients' stool or urine.

The following method is intended to reduce the problems with friction between the device and the sutures when parachuting a device through the esophagus. The method allows the device to be parachuted through the esophagus in a folded configuration, while it also allows the sutures to pass through the device while it is in an unfolded position. In addition, the method allows the sutures to be pulled through the device one at a time, which further reduces the problems with friction. This method can be used, for example, with the t-tag and/or t-tag delivery systems described herein.

1) Place fasteners (e.g. 6-10) in or through gastric wall with suture tails extending out through the patient's mouth; the sutures should have a length that is about 100-140 cm longer than required to exit the mouth;

2) thread suture tails through the device to be parachuted into place, e.g. an implant mounting ring or cuff;

3) slide the cuff down the sutures until it is just outside of the patient's mouth, with 100-140 cm of suture extending beyond the device;

4) fold or collapse the cuff and secure it in the collapsed position, e.g. with a removable sack or tied with a suture;

5) slide the cuff through the esophagus or the scope overtube (the cuff is not slid down the sutures, but instead the sutures are allowed to move with the cuff into the esophagus with the ends of the sutures remaining outside the patient);

6) once the cuff is through the esophagus and at the deployment site, the cuff is released from its collapsed position, and any restraining device that was used is removed perorally;

7) while controlling the cuff (e.g. with a grasper), and preferably under direct vision, pull each suture through the cuff until all the slack is removed and the cuff is at or near its intended position in the stomach;

8) position and secure the cuff in its intended position in the stomach.

In some clinical situations it may be beneficial to pre-strengthen the tissue prior to implantation of a device such as a gastrointestinal sleeve device. For example, energy can be delivered in the form of RF, ultrasound or other known method to induce an inflammatory, coagulative or necrotic tissue strengthening reaction. Alternatively, placement of material in the serosal tissue of the stomach wall could generate a foreign body reaction that would progress from inflammation, to granulation of tissue and then to fibrosis. The tissue may initially weaken due to the inflammatory response, but the resulting fibrotic growth will strengthen the tissue. This effect could be enhanced by the choice of material an/or coatings, e.g. sclerosing agent, an acidic material or coating. The materials could be delivered endoscopically with a needle device through the biopsy channel of an endoscope. The needle delivery device could optionally also deliver an ink, dye or other marking means to facilitate location of the prestrengthened areas. Tissue reaction could take place in days, with 7-14 days being an approximate delay between prestrengthening and attachment procedures.

Material injectable to prestrengthen tissue could be: 1) liquid where natural processes would remove/break down or otherwise dispose of the liquid when it has completed its function; 2) biodegradable or dissolvable where natural processes would remove the material when it has completed its function; or 3) permanent where the material might be incorporated into the tissue to provide increased strength. All of the prestrengthening strategies described could be used at the time of the attachment procedure to enhance strength of the attachment.

The methods and apparatus described for tissue strengthening would be expected to result in some degree of tissue thickening as new collagen and fibrotic material will be deposited and/or generated at the location of the foreign body reaction. The duration of exposure can be controlled by use of timed release chemical stimulants and stimulants with known and potentially controllable half lives. Tissue thickening and tissue strength may be related and may facilitate durable attachment, however tissue thickening may be an inherently desirable result in some clinical situations.

Currently, tissue bulking agents are injected at or near the GEJ 106 to treat GERD. Injection of non-bulking materials that initiate tissue thickening could accomplish the same end result. If the thickened tissue was, by itself or in conjunction with a supporting structure, to form a restrictive stoma, there could be specific advantages relative to a mechanical stoma.

Other approaches to induce tissue prestrengthening and/or thickening include: Circumferential ablation (RF, microwave, ultrasound, laser etc); Over-dilation; Circumferential abrasion; and, Circumferential exposure to agent. An advantage of a continuous or segmented circumferential area of tissue strengthening is that it only needs to be located along a vertical axis for subsequent attachment procedures.

Alternately or in addition to the above pre-strengthening of tissue, tissue can be treated to reduce its ability to move or stretch. This can be advantageous in that tissue that has limited stretch or motion may have less impediments to attachment. Tissue that has limited stretch or motion may impose fewer forces on an attached device and therefore impose less force or pressure that may lead to attachment failure. Furthermore, tissue that has limited stretch or motion may allow attachment of less compliant devices which can provide for advantages for example simplified sealing.

Techniques described above to strengthen tissue can also help to limited GI tissue stretch and motion. Other methods that could be applied to reducing stretch and motion, and also for pre-strengthening, include the application of energy for example, by RF, ultrasound or laser. Means that include time release elements as well known in the art of drug eluting vascular stents and birth control devices can be used to provide and/or maintain a long lasting effect (reducing motion and stretch). Such time release means can optionally be combined with fasteners, permanent or replaceable attachment cuffs or proximal sleeve interfaces. Such time release means can optionally be combined with permanently implanted pre-strengthening materials where the material might be incorporated into the tissue to provide increased strength.

In some clinical situations when using a transmural attachment, the wall of tissue may thicken after placement of the attaching device. In some cases this can progress to encapsulation. This thickening can result in increased tissue strength due to collagen deposition and/or fibrosis.

In some clinical situations it can be advantageous to maintain the attachment on the surface of the tissue to take advantage of the added strength of the thickened wall. This may be accomplished by permitting controlled suture lengthening to compensate for tissue thickening. One manner in which this could be accomplished would be by using a suture connecting the attachments on either side of the tissue wall that would stretch as the tissue thickens.

One configuration of material that could have advantageous performance would: 1) not stretch for an initial period, for example 24-48 hours; 2) stretch at a relatively low force for the next period, for example 7-14 days; then 3) not stretch after the second period. This performance would be based upon a clinical situation where tissue proliferation (wall thickening) occurs between days 2 and 14. Alternatively, the material could: 1) not stretch for the initial period, for example 24-48 hours; 2) allow lengthening to 2× length at any time after the initial period, for example 48 hours; then 3) not stretch beyond 2× length.

The length of the suture or other tension element which extends through the wall from the serosal surface to the mucosal surface, particularly when the tension element has a substantially fixed length under normal use conditions may also be important. The present inventors believe that the length of the tension element is in certain applications at least about 75%, often at least about 100%, and preferably at least about 120% and possibly at least about 130% of the thickness of the wall of the stomach through which the tension element is to be placed. Thus, for a patient having a wall thickness in the vicinity of the gastroesophageal junction of approximately 10-15 mm, suture lengths between the mucosal contacting surface of the implant and the serosal contacting surface of the retention element of at least about 10 mm, and often at least about 15 mm are contemplated.

The stomach appears to have unusual abilities to isolate foreign objects. Evidence of this is the lap band which can migrate from the serosal surface of the stomach into the lumen of the stomach without any immediate catastrophic event such as a leak of stomach contents into the body cavity which could be life threatening. The cause of such erosion is unclear but one theory suggests it is at least in part due to pressure.

The stomach is also a very active organ with an ability to stretch, compress, churn and move laterally relative to itself. This activity is normal in eating and digestion and can also function to isolate foreign objects.

These anatomical aspects make attachment of medical devices to the stomach quite challenging. A recent study at the Cleveland Clinic which sutured a prosthetic cuff to the GEJ 106 showed that by 7 days 80% of the cuffs had become primarily detached. In one animal that was survived for two months, the device remained attached at 4 weeks but was only 25% attached by 60 days.

The present inventors have conducted a series of studies to explore the parameters of a successful attachment. Initial designs utilizing rigid rings lost attachment at a majority of points within four weeks. Short term success at two weeks with a flexible cuff, with elastic ability, was achieved by using t-tags and placing them in the non-glandular tissue region of the GEJ 106. However this same technique at five weeks did not maintain 100% attachment. One-Third of the attachment points migrated through the stomach, leaving no identified histological evidence of their path. The t-tags did not appear to be deformed.

The inventors then undertook a series of experiments at five weeks controlling for the amount of tension on the tension element, by placing serosal surface attachment devices having tension elements with a predetermined length relative to the thickness of the tissue wall. The thickness of the porcine stomach at the target site was measured, and the average of four tissue thickness measurements at the 3-6-9-12 o'clock positions was used as the nominal thickness. The absolute thickness was somewhat surprising at around 1 cm. This was perceived to be much thicker than what was thought. The reasons for this could be increased thickness in the area of interest of the GEJ 106, but it could also be due to the highly compressible nature of stomach tissue in that when it is held between the thumb and index finger it does feel 1 cm thick.

In three experiments conducted there was a clear trend that the looser the attachment (i.e., the longer the length of the tension element compared to the local wall thickness) the more attachment points held at five weeks. Results ranged from 10/12 migrations for the sutures sized at 50% of nominal thickness to 2/12 migrations for sutures sized at 100% of nominal thickness.

Another variable which was explored in the porcine model was the effect of changes in the surface area of the retention element. Silicone buttons having a 1 cm diameter were used instead of the t-tags. In one experiment conducted to date at a suture length of 75% of nominal thickness, 4/12 silicone buttons migrated through.

What seemed different about the silicone buttons is with two-thirds of the attachments in place it appeared upon gross inspection to be very strongly functionally attached, with high weight bearing abilities, perceptually greater than the t-tags.

From the experiments to date it appears that tension control is as important (if not more so) as the geometry of the serosal attachment device.

As discussed elsewhere herein, tension control could be addressed by using suture with limited elastic properties or other structural mechanism that would stretch or elongate and then return to their nominal length. Another way is to use an assumed thickness, based upon an average of actual measurements in humans, and preset the length of the tension element at a predetermined length (e.g., at least 115%, at least 130%) compared to the length of the average. The chances of success for this approach would likely be enhanced if the patient to patient variation is relatively small. A further approach would be to measure the thickness of the target tissue in each patient, and customize the length of the tension element at the clinical site, or provide kits with a cuff and an array of anchor assemblies with tension elements of different predetermined lengths from which the clinician can make a selection. Measurement could be accomplished, for example, with endoscopic ultrasound, like a device available from Boston Scientific.

Once the measurement is taken a variety of devices could be used to attach with a controlled length. Many of these devices have been previously described and include t-tags, inflatable silicone discs, molly type devices, radial spoke "umbrella" structures and others. They can be attached to suture with a fixed cuff to retention element length (or other means) or a strut member made of polymer or metal with a nub to fix the length. All of these devices are preferably configured to permit endoscopic delivery through a single fire device, or a multiple fire or rapid reloadable device could be used, to minimize the number of times the delivery device needs to removed from the endoscope to be reloaded.

Another application of the present invention involves the placement of a mounting ring, aperture, hook, connector or other attachment device within the gastrointestinal system utilizing the serosal attachment disclosed herein and attaching any of a variety of devices or components to the attachment device. Applications for treating GERD, MO and other disorders of the gastrointestinal tract include placing/attaching a nonrestrictive mounting ring at or near the GEJ 106 and attaching/removing/replacing various therapeutic or diagnostic devices to the mounting ring, such as a valve to prevent reflux, a restriction to food intake, a sleeve, a telemetry or imaging capsule, transmitters for transmitting pH or other data, receivers for receiving therapeutic signals initiated by an external control, etc.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A method of treating a patient, comprising the steps of:
advancing a bypass sleeve deployment device transesophageally at least as far as the stomach;
advancing a distal end of a bypass sleeve from the bypass sleeve deployment device distally into the intestine;
attaching an attachment cuff in the vicinity of the gastroesophageal junction; and
attaching a proximal end of the bypass sleeve to the attachment cuff.

2. A method as in claim 1, wherein the advancing a bypass sleeve step comprises everting the bypass sleeve under pressure.

3. A method as in claim 1, wherein the attaching an attachment cuff step comprises advancing at least one tissue anchor through tissue in the area of the gastroesophageal junction.

4. A method as in claim 3, wherein the attaching an attachment cuff step comprises advancing at least eight tissue anchors through tissue in the area of the gastroesophageal junction.

5. A method as in claim 1, wherein the attaching the bypass sleeve step comprises reversibly attaching the bypass sleeve to the attachment cuff.

6. A method as in claim 1, wherein advancing the bypass sleeve deployment device transesophageally step comprises advancing the bypass sleeve deployment device transesophageally to about the pylorus.

7. A method as in claim 1, wherein attaching the attachment cuff step comprises attaching the attachment cuff at the gastroesophageal junction.

8. A method as in claim 1, wherein attaching the attachment cuff step comprises attaching the attachment cuff no more than about 2 cm below the squamocolumnar junction.

9. A method as in claim 1, wherein attaching the attachment cuff step comprises attaching the attachment cuff no more than about 1 cm below the squamocolumnar junction.

10. A method as in claim 1, wherein attaching the attachment cuff step comprises attaching the attachment cuff transmurally in the vicinity of the gastroesophageal junction.

11. A method as in claim 1, wherein advancing a bypass sleeve from the bypass sleeve deployment device distally into the intestine step comprises advancing the distal end of the bypass sleeve from the bypass sleeve deployment device distally into the duodenum.

12. A method as in claim 1, wherein advancing a bypass sleeve from the bypass sleeve deployment device distally into the intestine step comprises advancing the distal end of the bypass sleeve from the bypass sleeve deployment device distally into the jejunum.

13. A method as in claim 1, wherein advancing a bypass sleeve from the bypass sleeve deployment device distally into the intestine step comprises advancing the distal end of the bypass sleeve from the bypass sleeve deployment device distally into the ileum.

14. A method as in claim 1, wherein the method is accomplished endoscopically.

15. A method as in claim 1, wherein the bypass sleeve deployment device comprises a filling catheter.

* * * * *